(12) United States Patent
Hall et al.

(10) Patent No.: US 8,785,140 B2
(45) Date of Patent: Jul. 22, 2014

US008785140B2

(54) CD4+ CD25+ T-CELLS ACTIVATED TO A SPECIFIC ANTIGEN

(75) Inventors: Bruce M. Hall, Strathfield (AU); Suzanne J. Hodgkinson, Strathfield (AU)

(73) Assignee: New South Innovations Pty Limited, Syndey, New South Wales (AU)

( * ) Notice: Subject to any disclaimer, the term of this patent is extended or adjusted under 35 U.S.C. 154(b) by 1129 days.

(21) Appl. No.: 11/815,420

(22) PCT Filed: Feb. 2, 2006

(86) PCT No.: PCT/AU2006/000133
§ 371 (c)(1),
(2), (4) Date: Mar. 27, 2008

(87) PCT Pub. No.: WO2006/081620
PCT Pub. Date: Aug. 10, 2006

(65) Prior Publication Data
US 2008/0279813 A1    Nov. 13, 2008

(30) Foreign Application Priority Data

Feb. 2, 2005  (AU) ............................... 2005900442
Feb. 2, 2005  (AU) ............................... 2005900446

(51) Int. Cl.
*G01N 33/50*    (2006.01)
(52) U.S. Cl.
USPC ........................................................ 435/7.24
(58) Field of Classification Search
None
See application file for complete search history.

(56) References Cited

U.S. PATENT DOCUMENTS

| | | | |
|---|---|---|---|
| 4,520,110 A | 5/1985 | Stryer et al. | |
| 4,845,653 A | 7/1989 | Conrad et al. | |
| 4,876,190 A | 10/1989 | Recktenwald | |
| 5,342,774 A | 8/1994 | Boon et al. | |
| 5,622,853 A | 4/1997 | Terstappen et al. | |
| 5,731,160 A | 3/1998 | Melief et al. | |
| 6,312,692 B1 | 11/2001 | Noelle et al. | |
| 6,787,154 B2 | 9/2004 | Albani | |
| 6,828,150 B2 | 12/2004 | Cai et al. | |
| 2002/0031787 A1 | 3/2002 | Maclaren et al. | |
| 2003/0049696 A1 | 3/2003 | Norment et al. | |
| 2004/0173778 A1 | 9/2004 | Roncarolo et al. | |
| 2006/0121029 A1 | 6/2006 | Shiku | |

FOREIGN PATENT DOCUMENTS

| | | |
|---|---|---|
| CA | 2441213 A1 | 9/2002 |
| DE | 10234200 A1 | 2/2004 |
| EP | 1557172 A1 | 7/2005 |
| EP | 1997884 A1 | 12/2008 |
| JP | 2004-529631 | 9/2004 |
| WO | WO 00/20445 A2 | 4/2000 |
| WO | WO 01/37860 A1 | 5/2001 |
| WO | WO02/072799 A1 | 9/2002 |
| WO | WO 02/072799 A1 | 9/2002 |
| WO | WO 02/072832 A2 | 9/2002 |
| WO | WO2004/024174 A1 | 3/2004 |
| WO | WO 2004/024174 A1 | 3/2004 |
| WO | WO 2004/067554 A2 | 8/2004 |
| WO | WO2004/067554 A2 | 8/2004 |
| WO | WO2006/081620 A1 | 8/2006 |
| WO | WO2007/023491 A2 | 3/2007 |

OTHER PUBLICATIONS

Baecher-Allan et al., Semin Immunol. Apr. 2004;16(2):89-98.*
Janeway et al., Immunobiology, Garland Press, 2001, p. 520-522.*
Cope et al., Arthritis Res 2002, 4 (suppl 3):S197-S211.*
Graber et al., J Biol Chem. Jun. 30, 1995;270(26):15762-9.*
Plugariu et al., Biochemistry. Dec. 5, 2000;39(48):14939-49.*
Whitty et al., Chem. Biol. Apr. 1999;6(4):R107-18.*
Fawcett et al., The Journal of Cell Biology, vol. 128, 1995.*
Harber et al., Expert Rev Mol Med. Nov. 27, 2000;2(7):1-20.*
Verma et al., Blood, Jan. 8, 2009, vol. 113, No. 2, pp. 479-487.*
The link between error bars and statistical significance, pp. 1-3, obtained from http://www.graphpad.com/articles/errorbars.htm on Nov. 2, 2010.*
Kelchtermans et al., Arthritis Res Ther 2005, 7:R402-R415, 2005.*
Hall et al., Transplant Immunology 18 (2008) 291-301.*
Gately et al., J of Immuno., vol. 147, 874-882, No. 3, Aug. 1, 1991.*
Goldsby et al., Immunology, W.H. Freeman and Company, 5th ed., 2002, pp. 236-238.*
Perussia et al., J of Immuno., vol. 149, 3495-3502, No. 11, Dec. 1, 1992.*
Grundstrom et al. "Superantigen-Induced Regulatory T Cells Display Different Suppressive Functions in the Presence or Absence of Natural CD4+ CD25+ Regulatory T Cells In Vivo", Journal of Immunology 170(1):5008-5017 (2003) e.
McHugh et al. "The role of suppressor T cells in regulation of immune responses", Journal of Allergy and Clinical Immunology 110(5):693-702 (2002).
Mukherjee et al. "CD4+ CD25+ regulatory T cells generated in response to insulin B:9-23 peptide prevent adoptive transfer of diabetes by diabetogenic T cells", Journal of Autoimmunity 21(3):221-237 (2003).

(Continued)

*Primary Examiner* — Zachary Skelding
(74) *Attorney, Agent, or Firm* — Myers Bigel Sibley & Sajovec, P.A.

(57) ABSTRACT

The invention relates to a method of assessing whether a subject comprises CD4+,CD25+ T cells that have been activated to a specific antigen. The method comprises the steps of obtaining from the subject a sample of lymphocytes comprising CD4+,CD25+ T cells, incubating at least one portion of the sample of lymphocytes so as to promote distinction of CD4+,CD25+ T cells that have been activated to the specific antigen from those CD4+,CD25+ T cells that have not been activated to the specific antigen, and thereafter determining whether CD4+,CD25+ T cells activated to the specific antigen are present in the sample. The invention further relates to methods of growing CD4+, CD25+ T cells that have been activated to a specific antigen in vitro and to methods of increasing tolerance in a subject using the CD4+, CD25+ T cells that have been grown in vitro.

11 Claims, 37 Drawing Sheets

(56) References Cited

OTHER PUBLICATIONS

Papiernik et al. "Natural CD4+ CD25+ regulatory T cells. Their role in the control of superantigen responses", Immunological Reviews 182(1):180-189 (2001).
Shevach "CD4+ CD25+ Suppressor T Cells: More Questions Than Answers", Nature Reviews. Immunology 2 (6):389-400 (2002).
Grundstrom, et al., *Superantigen-Induced Regulatory T Cells Display Different Suppressive Functions in the Presence or Absence of Natural CD4+ CD25+ Regulatory T Cells in Vivo*, 2003, pp. 5008-5017, vol. 170, Journal of Immunology.
Levings, et al., *Human CD25+ CD4+ Regulatory Cells Suppress Naïve and Memory T Cell Proliferation and Can Be Expanded In Vitro without Loss of Function*, Jun. 4, 2001 pp. 1295-1301, vol. 193, J. Exp. Med.
Mukherjee, et al., *CD4+ CD25+ regulatory T cells generated in response to insulin 8:9-23 peptide prevent adoptive transfer of diabetes by diabetogenic T cells*, 2003, pp. 221-237, vol. 21, Journal of Autoimmunity.
Written Opinion—PCT/AU2006/000133.
ISR—PCT/AU2006/000133.
Hoffmann et al. "Large-scale in vitro expansion of polyclonal human $CD4^+CD25^{high}$ regulatory T cells", Blood, Am. Soc. of Hematology 104(3)895-903 (2004).
Krajina et al. "MHC class II-independent $CD25^+$ $CD4^+$ $CD8\alpha\beta^+$ $\alpha\beta$ cells attenuate $CD4^+$T cell-induced transfer colitis", Eur. J. Immunology 34(3):705-714 (2004).
Liotta et al. "Functional features of human $CD25^+$ regulatory thymocytes", Microbes and Infection 7:1017-1022 (2005).
Nakamura et al. "IL-2-independent generation of $FOXP3^+CD4^+$ $CD8^+CD25^+$ cytotoxic regulatory T cell lines from human umbilical cord blood", Experimental Hematology 35:287-296 2007.
Suzuki et al. "Suppressive activity mechanisms of novel cytotoxic regulatory T cell lines (HOZOT)", Cell Biology Research Center, Hayashibara Biochemical Laboratories, Inc. 36:225 (2006).
Kostakis et al. "Prolongation of Rat Heart Allograft Survival by Cyclosporin A" IRCS Med. Sci. Libr. Conpend. 5:280 (1977).
Knuth et al. "Cytolytic T-cell clones against an autologous human melanoma: Specificity study and definition of three antigens by immunoselection", Proc. Natl. Acad. Sci. USA 86:2804-2808 (1989).
Van Den Eynde et al. "Presence on a Human Melanoma of Multiple Antigens Recognized by Autologous CTL", Int. J. Cancer 44:634-640 (1989).
Tony et al. "Major Histocompatibility Complex-Restricted, Polyclonal B Cell Responses Resulting from Helper T Cell Recognition of Antiimmunoglobulin Presented by Small B Lymphocytes", J. Exp. Med. 161:223-241 (1985).
Plain et al. "Induction of Specific Tolerance to Allografts in Rats by Therapy with Non-Mitogenic, Non-Depleting Anti-CD3 Monoclonal Antibody", Transplantation 67(4):605-613 (1999).
Pearce et al. "Specific Unresponsiveness in Rats With Prolonged Cardiac Allograft Survival After Treatment With Cyclosporine", Transplantation 55(2):374-380 (1993).
Remington's Pharmaceutical Sciences 15th Ed. *Mack Publishing Company* Chp. 79:1405-1412; Chp. 84:1461-1487 (1975).
The National Formulary XIV, 14th Ed. Am. Pharmaceutical Assoc. (1975).
Goodman's and Gilman's "The Pharmacological Basis of Therapeutics", Macmillan Publishing Company (7th Ed.) (1985).
Langer "New Methods of Drug Delivery", Science (downloaded from www.sciencemag.org, 249:1527-1532 (1990).
Hall et al. "Specific Unresponsiveness in Rats With Prolonged Cardiac Allograft Survival After Treatment with Cyclosporine", J. Exp. Med. 171:141-157 (1990).
Nicolls et al. "Induction of Long-Term Specific Tolerance to Allografts in Rats by Therapy with an Anti-CD3-Like Monoclonal Antibody", Transplantation 55(3):459-468 (1993).
Plain et al. "Induction of Tolerance With Nondepleting Anti-CD4 Monoclonal Antibodies is Associated with Down-Regulation of TH2 Cytokines", Transplantation 64(11):1559-1567 (1997).
Pearce et al. "Specific Unresponsiveness in Rats With Prolonged Cardiac Allograft Survival After Treatment With Cyclosporine", Transplantation 55(2):380-389 (1993).
Hall et al. "Anti-CD4 Monoclonal Antibody-Induced Tolerance to MHC-Incompatible Cardiac Allografts Maintained by CD4+ Suppressor T Cells that are not Dependent upon IL-4", J. Immunol. 161:5146-5156 (1998).
Hall et al. "The Cellular Basis of Allograft Rejection In Vivo", J. Exp. Med. 148:878-889 (1978).
He et al. "Cloning and Expression of Interleukin-5 From Rats", Transplantation Proc. 31:1574-1576 (1999).
He et al. "Interleukin 13 Cloning From DA Rats" Transplantation Proc. 31:1572-1573 (1999).
He et al. "Treatment with Interleukin-4 Prolongs Allogeneic Neonatal Heart Graft Survival by Inducing T Helper 2 Responses", Transplantation 65(9):1145-1152 (1998).
Hodgkinson et al. "Transfer of experimental allergic neuritis by intra neural injection of sensitized lymphocytes", J. Neurol. Sci. 123:162-172 (1994).
Sun-Payer et al. "Differential Cytokine Requirements for Regulation of Autoimmune Gastritis and Colitis by CD4+CD25+ T Cells", J. of Autoimmunity 16:115-123 (2001).
Horwitz et al. "The role of the combination of IL-2 and TGF-β or IL-10 in the generation and function of CD4+ CD25+ and CD8+ regulatory T cell subsets", J. of Leukocyte Biology 74:471-478 (2003).
Bach "Regulatory T Cells Under Scrutiny", Nature Reviews Immunology 3:189-198 (2003).
Graca et al. "Donor-specific transplantation tolerance: The paradoxical behavior of CD4+CD25+ T cells", Proc. Natl. Acad. Sci. 101(27):10122-10126 (2004).
Thompson et al. "Regulatory T cells", Current Opinion in Pharmacology 4:408-414 2004.
Jiang et al. "Regulatory T Cells in the Control of Transplanatation Tolerance and Autoimmunity", Am. J. of Transplantation 3:516-524 (2003).
Nelson "IL-2, Regulatory T Cells, and Tolerance", J. of Immunol. 172:3983-3988 (2004).
Crispin et al. "Immunoregulatory T cells in autoimmunity", Autoimmunity Reviews 3:45-51 (2003).
Malek "The main function of IL-2 is to promote the development of T regulatory cells", J. of Leukocyte Biology 74:961-965 (2003).
Malek et al. "Tolerance Not Immunity, Crucially Depends on IL-2", Nature Reviews Immunol. 4:665-674 (2004).
He et al. "IL-5 Prolongs Allograft Survival by Downregulating IL-2 and IFNγ Cytokines", Transplant Proc. 33:703-704 (2001).
Nishimura et al. "Induction of antigen-specified immunologic tolerance by in vivio and in vitro antigen-specific expansion of naturally arising Foxp3+CD25+CD4+ regulatory T cells", International Immunol. 16(8):1189-1201 (2004).
Jonuleit et al. "Identification and Functional Characterization of Human CD4+CD25+ T Cells with Regulatory Properties Isolated from Peripheral Blood", J. Exp. Med. 193(11):1285-1294 (2001).
Read et al. "CD4+ regulatory T cells", Current Opinion in Immunology 13:644-649 (2001).
Sakaguchi et al. "Immunologic self tolerance maintained by T-cell-mediated control of self-reactive T cells: implications for autoimmunity and tumor immunity", Microbes and Infection 3:911-918 (2001).
Bhardwaj "Processing and presentation of antigens by dendritic cells: implications for vaccines", Trends in Molecular Medicine 7(9):388-394 (2001).
Monfardini et al. "Adoptive protection from experimental myasthenia gravis with T cells from mice treated nasally with acetylcholine receptor epitopes", J. of Neuroimmunology, 123:123-134 (2004.
Wekerle "Transplantation Tolerance Induced by Mixed Chimerism", J. of Heart and Lung Transplantation 20(8), :816-823 (2001).
Goodnow "Pathways for self-tolerance and the treatment of autoimmune disease", The Lancet 357:2115-2121 (2001).
Reid et al. "The control of T cell responses by dendritic cell subsets", Current Opion in Immunol. 12:114-121 (2000).

(56) References Cited

OTHER PUBLICATIONS

Stephens et al. "Phenotypic characterization of regulatory CD4+CD25+ T cells in rats", *International Immunol.* 16(2):365-375 (2004).

Chen et al. "CD4+, CD25+ T cells as Regulators of Alloimmune Responses", *Transplantation Proc.* 33:163-164 (2001).

Grundström et al. "Superantigen-Induced Regulatory T Cells Display Different Suppressive Functions in the Presence or Absence of Natural CD4$^+$ CD25$^+$ Regulatory T Cells In Vivo", *J. Immunology* 170:5008-5017,(2003).

Levings et al. "Human CD25$^+$ CD4$^+$ Regulatory Cells Suppress Naïve and Memory T Cell Proliferation and Can Be Expanded In Vitro without Loss of Function", *J. Exp. Med.* 193(11):1295-1301 (2001).

Mukherjee et al. "CD4$^+$CD25$^+$ regulatory T cells generated in response to insulin B:9-23 peptide prevent adoptive transfer of diabetes by diabetogenic T cells", *J. Autoimmunity* 21:221-237 (2003).

Papiernik "Natural CD4$^+$CD25$^+$ regulatory T cells. Their role in the control of superantigen responses", *Immunological Reviews* 182:180-189(2001).

Ildstad et al. "Preconditioning of NOD mice with anti-CD8 mAb and costimulatory blockade enhances chimerism and tolerance and prevents diabetes, while depletion of $\alpha\beta$-TCR$^+$ and CD4$^+$ cells negates the effect", *Blood* 105(6):2577-2584 (2005).

Taams et al. "Antigen-specific T cell suppression by human CD4$^+$CD25$^+$ regulatory T cells", *Eur. J. Immunol.* 32:1621-1630 (2002).

\* cited by examiner

CD4+ CD25+ T-CELLS ACTIVATED TO A SPECIFIC ANTIGEN

RELATED APPLICATIONS

The present application is a 35 U.S.C. §371 national phase application of PCT International Application No. PCT/AU2006/000133, having an international filing date of Feb. 2, 2006 and claiming priority to Australian Patent Application No. 2005900442, filed Feb. 2, 2005, and Australian Patent Application No. 2005900446, filed Feb. 2, 2005, the disclosures of which are incorporated herein by reference in their entireties. The above PCT International Application was published in the English language and has International Publication No. WO 2006/081620.

FIELD OF THE INVENTION

The invention relates to a method of assessing whether a subject comprises $CD4^+, CD25^+$ T cells that have been activated to a specific antigen, a method for determining whether a subject is tolerant, or capable of becoming tolerant, to an antigen, and to methods for increasing or decreasing tolerance to an antigen in a subject.

BACKGROUND OF THE INVENTION

The immune system provides a mechanism to protect the body against infection by foreign entities such as infectious organisms or foreign antigens. Under normal conditions, the immune system is capable of recognising and eliciting an immune response against foreign entities, while largely ignoring host tissue. The ability of the immune system to ignore the host's tissue is known as immune tolerance. Immune tolerance also refers to a state where the immune system is adapted to ignore antigens such as transplanted foreign tissues, infected tissues, allergens and malignant tissues.

Autoimmune disease occurs when T cells recognise and react to "self" molecules, that is, molecules produced by the cells of the host. This occurs when specific self molecules interact with proteins on the surface of T cells such that the T cells recognise the molecule as foreign and consequently elicit an immune response against the self molecule. In tissue transplantation, non-self major histocompatibility antigen present on the foreign tissue contacts the surface of T cells, resulting in T-cell activation against the foreign antigen. This activation ultimately results in allograft or xenograft rejection by the immune system.

Present methods for preventing allograft rejection, or for treating autoimmune disease, typically cause a general immunosuppression that is not specific for a specific antigen or antigens. As a result, the subject is rendered susceptible to infection from pathogenic and opportunistic organisms, and may be at an increased risk of malignancy. The more specific immunosuppressive drugs such as cyclosporin A, steroids, azathioprine, anti-T-cell antibodies, rapamycin, mycophenolate mofetil, desoxyspergualine and FK506, typically have undesirable side-effects, and typically require that the subject be administered the drugs for life or at least extended periods of time, thereby placing the subject at considerable risk of infection, cancer, and/or other conditions due to long term effects of the treatment. It would therefore be advantageous to provide a method of inducing tolerance to a specific antigen in a subject. Such a method could be used to suppress the immune response to "self" molecules in a subject having an autoimmune disease, or to suppress the immune response to transplant tissue by inducing tolerance to antigens present on the transplant tissue.

Disease conditions may also result from, or be exacerbated by, the development of immune tolerance to a specific antigen. For example, diseases such as cancer and chronic infections may result from, or progress because of, the development of immune tolerance to tumour or other antigens present on the malignant or pre-malignant cells or antigens of infectious agents expressed by infected cells. It would therefore also be desirable to provide a method of reducing or breaking tolerance to a specific antigen in a subject suffering from disease resulting from or exacerbated by the development of immune tolerance to a specific antigen.

It would further be desirable to provide a method for assessing whether a subject is capable of becoming tolerant to a specific antigen. For example, treatment of patients with immunosuppressive drugs such as cyclosporin A can in some cases lead to tolerance or partial tolerance to specific antigens such as self molecules or alloantigens. If the onset of tolerance could be detected in a patient on such immunosuppressive drug therapy, or in other circumstances, an assessment could be made as to whether the patient still required high levels of immunosuppressive drugs, or whether they had developed sufficient tolerance to a specific antigen to permit the dose of immunosuppressive drugs to be reduced or eliminated.

SUMMARY OF THE INVENTION $CD4^+$ T cells are a subset of lymphocytes that are central to inducing an immune response in a human or animal body. $CD4^+, CD25^+$ T cells are a subpopulation of $CD4^+$ T cells which represent approximately 1% to 10% of the total $CD4^+$ T cell population in a human or animal body.

$CD4^+, CD25^+$ T cells activated to an antigen are capable of imparting to cells of the immune system, including $CD4^+, CD25^-$ T cell populations and $CD8^+$ T cells, tolerance to that antigen.

Activated $CD4^+, CD25^+$ T cells are formed when naïve $CD4^+, CD25^+$ T cells contact an antigen in the presence of interleukin-2 (IL-2) and/or interleukin-4 (IL-4). The activated $CD4^+, CD25^+$ T cells initially proliferate following activation. However, the inventors have found that activated $CD4^+, CD25^+$ T cells die, or are not capable of further proliferation after an initial proliferation following activation, unless exposed to specific cytokines.

The inventors have found that naïve $CD4^+, CD25^+$ T cells do not express receptors for IL-5, IL-12 or IFN-γ. However, the inventors have found that when naïve $CD4^+, CD25^+$ T cells are activated by contacting the naïve $CD4^+, CD25^+$ T cells with an antigen and IL-2, the $CD4^+, CD25^+$ T cells express the IFN-γ receptor and the IL-12 β2 receptor. The inventors have found that when naïve $CD4^+, CD25^+$ T cells are activated by contacting the naïve $CD4^+, CD25^+$ T cells with an antigen and IL-4, the $CD4^+, CD25^+$ T cells express the IL-5 a-receptor, and expression of IFN-γ mRNA increases. The inventors have found that the cytokines interleukin-5 (IL-5), interleukin-12 (IL-12), interleukin-23 (IL-23) and interferon-γ (IFN-γ) are capable of prolonging the survival, and supporting proliferation, of activated $CD4^+, CD25^+$ T cells.

Based on their findings, the inventors have developed methods for determining whether a subject comprises $CD4^+, CD25^+$ T cells that have been activated to a specific antigen, methods for determining whether a subject is tolerant, or capable of becoming tolerant, to a specific antigen, methods for growing CD4$^+$,CD25$^+$ T cells activated to a specific antigen, and methods for inducing and reducing tolerance to a specific antigen.

In a first aspect, the invention provides a method of assessing whether a subject comprises CD4$^+$,CD25$^+$ T cells that have been activated to a specific antigen, comprising the steps of:
(a) obtaining from the subject a sample of lymphocytes comprising CD4$^+$,CD25$^+$ T cells;
(b) incubating at least one portion of the sample of lymphocytes so as to promote distinction of CD4$^+$,CD25$^+$ T cells that have been activated to the specific antigen from CD4$^+$,CD25$^+$ T cells that have not been activated to the specific antigen;
(c) thereafter determining whether CD4$^+$,CD25$^+$ T cells that have been activated to the specific antigen are present in the sample.

Typically, step (b) of the method comprises incubating the at least one portion of the sample under conditions that favour the survival and/or proliferation of CD4$^+$,CD25$^+$ T cells that have been activated to the specific antigen in preference to other CD4$^+$,CD25$^+$ T cells, or incubating the at least one portion of the sample under conditions that favour the survival and/or proliferation of CD4$^+$,CD25$^+$ T cells that have not been activated to the specific antigen in preference to CD4$^+$,CD25$^+$ T cells that have been activated to the specific antigen.

In some embodiments, the at least one portion of the sample is incubated in the presence of the specific antigen and one or more cytokines capable of prolonging survival and/or supporting proliferation of activated CD4$^+$,CD25$^+$ T cells. The incubation of the at least one portion of the sample under these conditions favours the survival and/or proliferation of CD4$^+$,CD25$^+$ T cells that have been activated to the specific antigen. The one or more cytokines capable of prolonging survival or supporting proliferation of activated CD4$^+$,CD25$^+$ T cells are typically cytokines selected from the group consisting of IL-5, IL-12, IL-23 and IFN-γ, biologically active fragments thereof, and functionally equivalent molecules thereof. In these embodiments, it can be determined that CD4$^+$,CD25$^+$ T cells that have been activated to the specific antigen are present in the sample if:
(a) proliferation of CD4$^+$,CD25$^+$ T cells is detected;
(b) in samples comprising CD4$^+$,CD25$^+$ and CD4$^+$,CD25$^-$ T cells, there is a reduction of CD4$^+$,CD25$^-$ T cell proliferation in response to the specific antigen; or
(c) molecules are detected which indicate the presence of CD4$^+$,CD25$^+$ T cells that have been activated to the specific antigen.

In some other embodiments, the at least one portion of the sample is incubated in the presence of the specific antigen and in the absence of cytokines capable of stimulating activation of CD4$^+$,CD25$^+$ T cells or of prolonging survival or supporting proliferation of activated CD4$^+$,CD25$^+$ T cells. In these embodiments, it can be determined that CD4$^+$,CD25$^+$ T cells that have been activated to the specific antigen are present in the sample if:
(a) there is reduced proliferation of CD4$^+$,CD25$^+$ T cells;
(b) in samples comprising CD4$^+$,CD25$^+$ and CD4$^+$,CD25$^-$ T cells, there is increased proliferation of CD4$^+$,CD25$^-$ T cell in response to the specific antigen.

In the absence of cytokines capable of prolonging survival or supporting proliferation of activated CD4$^+$,CD25$^+$ T cells, CD4$^+$,CD25$^+$ T cells activated to a specific antigen will not proliferate following contact with the specific antigen, and typically will not survive, or will exhibit reduced proliferation relative to CD4$^+$,CD25$^+$ T cells that have not been activated to the specific antigen. Accordingly, when the at least one portion of the sample is incubated in the presence of the specific antigen and in the absence of cytokines capable of stimulating activation of CD4$^+$,CD25$^+$ T cells or of prolonging survival or supporting proliferation of activated CD4$^+$,CD25$^+$ T cells, a reduction in survival and/or proliferation of CD4$^+$,CD25$^+$ T cells will indicate the presence of CD4$^+$,CD25$^+$ T cells activated to the specific antigen in the sample. In a sample comprising CD4$^+$,CD25$^+$ and CD4$^+$,CD25$^-$ T cells, a reduction in survival and/or proliferation of CD4$^+$,CD25$^+$ T cells will result in an increase in proliferation of the CD4$^+$,CD25$^-$ T cells. This is because a reduction in survival and/or proliferation of CD4$^+$,CD25$^+$ T cells in the sample will mean these cells are no longer able to suppress the proliferation of CD4$^+$, CD25$^-$ T cells in response to the specific antigen. On the other hand, naïve CD4$^+$,CD25$^+$ T cells and CD4$^+$,CD25$^+$ T cells that have been activated to other antigens will survive when incubated under these conditions, and will be able to suppress proliferation of CD4$^+$,CD25$^+$ T cells. The presence of CD4$^+$, CD25$^+$ T cells activated to a specific antigen in the sample indicates that the subject is tolerant, or capable of becoming tolerant, to the specific antigen.

In a second aspect, the invention provides a method of determining whether a subject is tolerant, or capable of becoming tolerant, to a specific antigen, comprising the steps of:
(a) obtaining from the subject a sample of lymphocytes comprising CD4$^+$,CD25$^+$ T cells;
(b) contacting at least one portion of the sample of lymphocytes with the specific antigen;
(c) incubating the at least one portion of the sample of lymphocytes in the absence of cytokines capable of stimulating activation of CD4$^+$,CD25$^+$ T cells or of prolonging survival or supporting proliferation of activated CD4$^+$,CD25$^+$ T cells, or in the presence of at least one cytokine selected from the group consisting of IL-5, IL-12, IL-23 and IFN-γ, or a biologically active fragment thereof, or a functionally equivalent molecule thereof;
(d) thereafter determining whether CD4$^+$,CD25$^+$ T cells that have been activated to the specific antigen are present in the sample.

The presence of CD4$^+$,CD25$^+$ T cells activated to the specific antigen in the sample may be determined by detecting:
(i) no or low proliferation of CD4$^+$,CD25$^+$ T cells when the at least one portion of the sample of lymphocytes is contacted with the specific antigen and incubated in the absence of cytokines capable of stimulating activation of CD4$^+$,CD25$^+$ T cells or of prolonging survival and/or supporting proliferation of activated CD4$^+$,CD25$^+$ T cells; or
(ii) proliferation of CD4$^+$,CD25$^+$ T cells when the at least one portion of the sample of lymphocytes is contacted with the specific antigen and incubated in the presence of at least one cytokine selected from the group consisting of IL-5, IL-12, IL-23 and IFN-γ, or a biologically active fragment thereof, or a functionally equivalent molecule thereof; or
(iii) molecules which indicate the presence of activated CD4$^+$,CD25$^+$ T cells when the at least one portion of the sample of lymphocytes is contacted with the specific antigen and incubated in the presence of at least one cytokine selected from the group consisting of IL-5, IL-12, IL-23 and IFN-γ, or a biologically active fragment thereof, or a functionally equivalent molecule thereof; or (iv) inhibition of proliferation of CD4$^+$,CD25$^-$ T cells when the at least one portion of the sample comprises CD4$^+$,CD25$^+$ T cells and CD4$^+$CD25$^-$ T cells, and the at least one portion of the sample of lymphocytes is contacted with the specific antigen and incubated in the presence of at least one cytokine selected from the group consisting of IL-5, IL-12, IL-23 and IFN-γ, or a biologically active fragment thereof, or a functionally equivalent molecule thereof; and/or (v) stimulation of proliferation of CD4$^+$,CD25$^-$ T cells when the at least one portion of the sample comprises CD4$^+$,CD25$^+$ T cells and CD4$^+$,CD25$^-$ T cells, and the at least one portion of the sample of lymphocytes is contacted with the specific antigen and incubated in the absence of cytokines capable of stimulating proliferation of CD4$^+$,CD25$^+$ T cells, or prolonging survival or supporting proliferation of activated CD4$^+$,CD25$^+$ T cells.

Molecules which indicate the presence of activated CD4$^+$, CD25$^+$ T cells may be metabolic products that are signals of activation, or markers of activation such as expression of the IL-5 receptor, the IL-12 receptor, or the IFN-γ receptor.

Typically, the IL-12 is IL-12p70.

In one embodiment, the at least one portion of the sample of lymphocytes is incubated in the absence of cytokines capable of stimulating activation of CD4$^+$,CD25$^+$ T cells or of prolonging survival or stimulating proliferation of activated CD4$^+$,CD25$^+$ T cells and in the presence of anti-IL-2 and/or anti-IL-4 antibodies. In this embodiment, the presence of activated CD4$^+$,CD25$^+$ T cells in the sample may be determined by detecting no or low proliferation of CD4$^+$,CD25$^+$ T cells.

In one embodiment, the at least one portion of the sample of lymphocytes is incubated in the presence of at least one cytokine selected from the group consisting of IL-5, IL-12, IL-23 and IFN-γ, or a biologically active fragment thereof, or a functionally equivalent molecule thereof, and in the presence of anti-IL-2 and/or anti-IL-4 antibody. In this embodiment, the presence of activated CD4$^+$,CD25$^+$ T cells in the sample may be determined by detecting proliferation of CD4$^+$,CD25$^+$ T cells.

The sample of lymphocytes may be any population of lymphocytes obtained from the subject which contains CD4$^+$, CD25$^+$ T cells. In one embodiment, the sample of lymphocytes is isolated CD4$^+$,CD25$^+$ T cells. In another embodiment, the sample is isolated CD4$^+$ T cells. In yet another embodiment, the sample is a mixed lymphocyte population. Typically, the mixed lymphocyte population is unfractionated lymphocytes. In yet another embodiment, the sample may be an admixed T cell population obtained by mixing isolated CD4$^+$,CD25$^+$ T cells and isolated CD4$^+$,CD24$^-$ T cells obtained from the subject.

In one embodiment, at least one portion of the sample of lymphocytes is incubated with an antibody which reduces proliferation of CD4$^+$,CD25$^-$ lymphocytes. Antibodies which reduce the proliferation of CD4$^+$,CD25$^-$ T cells include anti-CD3, anti-CD45RB/RO or any other antibody which specifically binds to CD4$^+$,CD25$^-$ T cells.

The lymphocytes may be contacted with the specific antigen in any manner which presents the specific antigen to the lymphocyte in a form which will permit the lymphocyte to recognise the specific antigen. The at least one portion of the sample of lymphocytes may be contacted with the specific antigen prior to, or simultaneously with, incubating at least one portion of the sample of lymphocytes in the absence of cytokines capable of stimulating activation of CD4$^+$,CD25$^+$ T cells or of prolonging survival or supporting proliferation of activated CD4$^+$,CD25$^+$ T cells, or in the presence of at least one cytokine selected from the group consisting of IL-5, IL-12, IL-23 and IFN-γ, or a biologically active fragment thereof, or a functionally equivalent molecule thereof. In some embodiments the at least one portion of the sample is contacted with the specific antigen by incubating the at least one portion of the sample with the specific antigen.

The specific antigen may be an antigen located on the surface of an antigen presenting cell. In such a case, the specific antigen may be associated with a class II major histocompatability molecule on the surface of the antigen presenting cell. The antigen presenting cell may be any cell that expresses an antigen presenting molecule (typically class II MHC) and, typically, ligands required to facilitate activation of the CD4$^+$,CD25$^+$ T cells. Examples of ligands include ICAM1, ICAM2, LFA3, ligands for CD28 and CTLA-4 or any activation ligands. Examples of antigen presenting cells include dendritic cells, phagocytes, B-lymphocytes, Langerhans cells or unfractionated lymphocytes in which the proliferation of the stimulator cells is impaired (for example, by irradiation or mitomycin C treatment).

Alternatively, the at least one portion of the sample of lymphocytes may be contacted with the specific antigen in a synthetic antigen presenting system such as that described in, for example, U.S. Pat. Nos. 6,828,150 or 6,787,154.

Where the at least one portion of the sample of lymphocytes is incubated in the presence of at least one cytokine selected from the group consisting of IL-5, IL-12, IL-23 and IFN-γ, or a biologically active fragment thereof, or a functionally equivalent molecule thereof, the at least one portion of the sample of lymphocytes may be incubated in the presence of the at least one cytokine simultaneous with, or subsequent to, contacting the at least one portion of the sample of lymphocytes with the specific antigen.

Typically, the at least one portion of the sample of lymphocytes is incubated in medium. The medium is typically substantially free of exogenous antigens which may cause activation of lymphocytes, other than the specific antigen. In other words, the levels of exogenous antigen present in the medium are sufficiently low, or absent, such that CD4$^+$ T cells do not activate to exogenous antigens (other than the specific antigen) in the medium.

When the at least one portion of the sample of lymphocytes is incubated in the presence of at least one cytokine selected from the group consisting of IL-5, IL-12, IL-23 and IFN-γ, or a biologically active fragment thereof, or a functionally equivalent molecule thereof, the at least one cytokine selected from the group consisting of IL-5, IL-12, IL-23 and IFN-γ, or a biologically active fragment thereof, or a functionally equivalent molecule thereof, is typically added to the medium from an exogenous source. The at least one cytokine selected from the group consisting of IL-5, IL-12, IL-23 and IFN-γ, or a biologically active fragment thereof, or a functionally equivalent molecule thereof, may be purified proteins, recombinant or otherwise. Alternatively, the at least one portion of the sample of lymphocytes may be incubated in the presence of cells which express the at least one cytokine selected from the group consisting of IL-5, IL-12, IL-23 and IFN-γ, or a biologically active fragment thereof, or a functionally equivalent molecule thereof. The medium may comprise growth factors, nutrients and/or buffers.

Typically, when the sample of lymphocytes is incubated in the absence of cytokines capable of stimulating activation of CD4$^+$,CD25$^+$ T cells or of prolonging survival or stimulating proliferation of activated CD4$^+$,CD25$^+$ T cells, the sample is incubated in medium which is substantially free of cytokines.

Proliferation of the CD4$^+$,CD25$^+$ T cells and CD4$^+$,CD25$^-$ T cells may be determined by any methods known in the art. For example, proliferation of the CD4$^+$,CD25$^+$ T cells may be determined by determining the number of CD4$^+$,CD25$^+$ T cells, or determining the proportion of CD4$^+$,CD25$^+$ T cells that are proliferating.

The number of CD4$^+$,CD25$^+$ T cells or CD4$^+$,CD25$^-$ T cells may be determined using any methods known in the art for measuring cell numbers. Such methods include flow cytometry, immunofluorescent microscopy, etc.

The proportion of proliferating CD4$^+$,CD25$^+$ T cells and/or CD4$^+$,CD25$^-$ T cells may be determined by methods such as rate of incorporation of radiolabels such as [H$^3$]-thymidine or incorporation of fluorescent dyes such as ethidium bromide, acridine orange etc.

The specific antigen may be any antigen. The specific antigen may be an autoantigen of the subject and the subject has an autoimmune disease or condition.

The specific antigen may be an alloantigen, for example, an antigen of allograft tissue following, or prior to, an allograft to the subject, or in other words, a transplant of tissue to the subject from another subject of the same species.

The specific antigen may be a xenoantigen, for example, an antigen of xenograft tissue following, or prior to, a xenograft to the subject, or in other words, a transplant of tissue to the subject from a species different to that of the subject.

The specific antigen may be an allergen or part of an allergen that induces the allergic response.

The specific antigen may be a tumour antigen. An example of a tumour antigen is a neoantigen, a tumour cell or a pre-malignant cell.

The specific antigen may be an antigen from an infectious agent.

The specific antigen may be a single specific antigen, or a plurality of specific antigens.

The specific antigen may be a cell transfected with an agent such as a therapeutic agent. In such a case, the cell is typically autologous to the subject. Typically, the cell transfected with an agent is a stem cell.

In a third aspect, the invention provides a method of growing in vitro CD4$^+$,CD25$^+$ T cells activated to a specific antigen, comprising the step of culturing CD4$^+$,CD25$^+$ T cells activated to the specific antigen in vitro in the presence of at least one cytokine selected from the group consisting of IL-5, IL-12, IL-23 and IFN-γ, or a biologically active fragment thereof, or a functionally equivalent molecule thereof.

In one embodiment, the method comprises the further step of contacting the CD4$^+$,CD25$^+$ T cells activated to the specific antigen with the specific antigen in vitro. The activated CD4$^+$,CD25$^+$ T cells may be contacted with the specific antigen in vitro prior to, or simultaneously with, culturing the T cells in the presence of the at least one cytokine selected from the group consisting of IL-5, IL-12, IL-23 and IFN-γ, or a biologically active fragment thereof, or a functionally equivalent molecule thereof. In some embodiments, the activated CD4$^+$,CD25$^+$ T cells are cultured in the presence of the at least one cytokine selected from the group selected from IL-5, IL-12, IL-23 and IFN-γ, or a biologically active fragment thereof, or a functionally equivalent molecule thereof, after contacting the activated T cells with the specific antigen.

Typically, the activated CD4$^+$,CD25$^+$ T cells are cultured in the absence of conconavalin A and/or 1-o-methyl α-mannopyranoside.

Typically, the IL-12 is IL-12p70.

In a fourth aspect, the invention provides a method of increasing tolerance to a specific antigen in a subject in need thereof, comprising administering to the subject an effective amount of CD4$^+$,CD25$^+$ T cells activated to the specific antigen grown in vitro by culturing the activated CD4$^+$,CD25$^+$ T cells in the presence of at least one cytokine selected from the group consisting of IL-5, IL-12, IL-23 and IFN-γ, or a biologically active fragment thereof, or a functionally equivalent molecule thereof.

In one embodiment, the method comprises the further step of contacting the CD4$^+$,CD25$^+$ T cells activated to the specific antigen with the specific antigen in vitro.

The CD4$^+$,CD25$^+$ T cells activated to a specific antigen may be contacted with the specific antigen in vitro prior to, or simultaneous with, culturing the activated T cells in the presence of the at least one cytokine selected from the group consisting of IL-5, IL-12, IL-23 and IFN-γ, or a biologically active fragment thereof, or a functionally equivalent molecule thereof. In some embodiments, the T cells are cultured in the presence of the at least one cytokine selected from the group consisting of IL-5, IL-12, IL-23 and IFN-γ, or a biologically active fragment thereof, or a functionally equivalent molecule thereof after contacting the activated T cells with the specific antigen.

Typically, the CD4$^+$,CD25$^+$ T cells activated to a specific antigen are cultured in vitro in the absence of conconavalin A and/or 1-o-methyl α-mannopyranoside.

Typically, the IL-12 is IL-12p70.

In one embodiment, the CD4$^+$,CD25$^+$ T cells activated to a specific antigen are cultured in vitro in the absence of IL-2 and IL-4.

Without wishing to be bound by theory, the inventors believe that tolerance to a specific antigen may be increased by increasing the ratio of CD4$^+$,CD25$^+$ T cells activated to the specific antigen relative to the CD4$^+$,CD25$^-$ T cells in a subject. Administering CD4$^+$,CD25$^+$ T cells activated to the specific antigen, increases the ratio of CD4$^+$,CD25$^+$ T cells activated to the specific antigen to CD4$^+$,CD25$^-$ T cells in the subject. The ratio of CD4$^+$,CD25$^+$ T cells activated to the specific antigen to CD4$^+$,CD25$^-$ T cells in a subject may be further increased by reducing the number of CD4$^+$ T cells in the subject prior to administering the CD4$^+$,CD25$^+$ T cells activated to the specific antigen. The CD4$^+$ T cells may be reduced in number by any methods known in the art. Lymphocytes, including CD4$^+$ T cells, may be reduced by irradiation. The CD4$^+$ lymphocytes may be reduced by administering to the subject one or more antibodies which specifically bind to CD4$^+$ T cells, typically to CD4$^+$,CD25$^-$ T cells. Suitable antibodies include one or more antibodies selected from the group consisting of anti-CD3, anti-CD4, anti-CD45RB/RO, anti-lymphocyte globulin or anti-thymocyte globulin. In embodiments where the CD4$^+$ T cells are reduced by administering antibodies that specifically bind to the CD4$^+$ T cells or lymphocytes, the antibodies may be subsequently removed or inactivated. Methods for removal or inactivation of antibodies include administration of anti-idiotype antibodies, soluble CD4 ligand, antibodies against the treating antibody or any other technique that removes or neutralizes the treating antibody.

In one embodiment, the CD4$^+$,CD25$^+$ T cells activated to the specific antigen are derived from naïve T cells that are activated in vitro. The naïve T cells may be activated in vitro by contacting naïve CD4$^+$,CD25$^+$ T cells with the specific antigen in vitro, and culturing the T cells in the presence of one or more cytokines capable of supporting activation of naïve CD4$^+$,CD25$^+$ T cells. Typically, the cytokine capable of supporting activation of the naïve CD4$^+$,CD25$^+$ T cells is IL-2, a biologically active fragment thereof, or a functionally equivalent molecule thereof, or IL-4, a biologically active fragment thereof, or a functionally equivalent molecule thereof.

The naïve CD4$^+$,CD25$^+$ T cells may be activated in vitro by:
(a) contacting the naïve CD4$^+$,CD25$^+$ T cells with the specific antigen; and
(b) culturing the CD4$^+$,CD25$^+$ T cell in the presence of IL-2, a biologically active fragment thereof, or functionally equivalent molecule thereof.

Typically, CD4$^+$,CD25$^+$ T cells that have been activated in the presence of IL-2, a biologically active fragment thereof, or functionally equivalent molecule thereof, are simultaneously, or subsequently, cultured in the presence of IL-12, a biologically active fragment thereof, or a functionally equivalent molecule thereof, and/or IFN-γ, a biologically active fragment thereof, or a functionally equivalent molecule thereof.

Naïve CD4$^+$,CD25$^+$ T cells may alternatively activated in vitro by:
(a) contacting the naïve CD4$^+$,CD25$^+$ T cells with the specific antigen; and
(b) culturing the CD4$^+$,CD25$^+$ T cell in the presence of IL-4, a biologically active fragment thereof, or functionally equivalent molecule thereof.

In some embodiments, the CD4$^+$,CD25$^+$ T cells that have been activated in the presence of IL-4, a biologically active fragment thereof, or functionally equivalent molecule thereof, are simultaneously, or subsequently, cultured in the presence of IL-5 or IL-13, a biologically active fragment thereof, or a functionally equivalent molecule thereof. In some embodiments, naïve CD4$^+$,CD25$^+$ T cells that have been activated in the presence of IL-4, a biologically active fragment thereof, or a functionally equivalent molecule thereof, may be cultured in the presence of IL-5, a biologically active fragment thereof, or a functionally equivalent molecule thereof, and IL-13, a biologically active fragment thereof, or a functionally equivalent molecule thereof.

Naïve CD4$^+$,CD25$^+$ T cells may be activated in vitro by:
(a) contacting the naïve CD4$^+$,CD25$^+$ T cells with the specific antigen; and
(b) culturing the CD4$^+$,CD25$^+$ T cells in the presence of IL-2, a biologically active fragment thereof, or a functionally equivalent molecule thereof, and IL-4, a biologically active fragment thereof, or functionally equivalent molecule thereof.

Typically, the CD4$^+$,CD25$^+$ T cells that have been activated in the presence of IL-2, a biologically active fragment thereof, or a functionally equivalent molecule thereof, and IL-4, a biologically active fragment thereof, or a functionally equivalent molecule thereof, are simultaneously, or subsequently, cultured in the presence of one or more of the cytokines selected from the group consisting of IL-5, IL-12, IL-23 and IFN-γ, or a biologically active fragment thereof, or a functionally equivalent molecule thereof. The CD4$^+$,CD25$^+$ T cells that have been activated in the presence of IL-2, a biologically active fragment thereof, or a functionally equivalent molecule thereof, and IL-4, a biologically active fragment thereof, or a functionally equivalent molecule thereof, may further be cultured in the presence of IL-13, a biologically active fragment thereof, or a functionally equivalent molecule thereof.

In another embodiment, the CD4$^+$,CD25$^+$ T cells may be activated to the specific antigen in vivo prior to culturing in vitro. For example, CD4$^+$,CD25$^+$ T cells may be isolated from the subject already activated to the specific antigen. It is envisaged that the CD4$^+$,CD25$^+$ T cells activated to a specific antigen from the subject would typically be activated following contact with specific antigen and exposure to IL-2 and/or IL-4 in the subject, or in other words, in vivo.

It is also envisaged that a sample of CD4$^+$,CD25$^+$ T cells from a subject may contain naïve CD4$^+$,CD25$^+$ T cells and CD4$^+$,CD25$^+$ T cells which have been activated to the specific antigen. These cells may be grown by contacting the naïve CD4$^+$,CD25$^+$ T cells and CD4$^+$,CD25$^+$ T cells activated to the specific antigen with the specific antigen in vitro, and culturing the naïve CD4$^+$,CD25$^+$ T cells and CD4$^+$,CD25$^+$ T cells activated to the specific antigen in the presence of IL-2, a biologically active fragment thereof, or a functionally equivalent molecule thereof, and/or IL-4, a biologically active fragment thereof, or a functionally equivalent molecule thereof, and at least one cytokine selected from the group consisting of IL-5, IL-12, IL-23 and IFN-γ, or a biologically active fragment thereof, or a functionally equivalent molecule thereof. In some embodiments, the CD4$^+$,CD25$^+$ T cells may further be cultured in the presence of IL-13, a biologically active fragment thereof, or a functionally equivalent molecule thereof.

In the method of the third or fourth aspect of the present invention, the CD4$^+$,CD25$^+$ T cells activated to the specific antigen may be cultured in any medium which comprises at least one cytokine selected from the group consisting of IL-5, IL-12, IL-23 and IFN-γ, or a biologically active fragment thereof, or a functionally equivalent molecule thereof. The medium is typically free of conconavalin A and/or 1-o-methyl α-mannopyranoside. The medium may contain, in addition to at least one cytokine selected from the group consisting of IL-5, IL-12, IL-23 and IFN-γ, or a biologically active fragment thereof, or a functionally equivalent molecule thereof, one or more cytokines selected from the group consisting of IL-2, IL-4, biologically active fragments thereof, and functionally equivalent molecules thereof. The medium may contain, in addition to at least one cytokine selected from the group consisting of IL-5, IL-12, IL-23 and IFN-γ, or a biologically active fragment thereof, or a functionally equivalent molecule thereof, one or more antibodies which are directed against CD4$^+$,CD25$^-$ T cells. Examples of such antibodies include anti-CD3, anti-CD45RB/RO. The medium may in addition contain IL-13, a biologically active fragment thereof, or a functionally equivalent molecule thereof.

The CD4$^+$,CD25$^+$ T cells activated to the specific antigen are typically cultured in the presence of at least one cytokine selected from the group consisting of IL-5, IL-12, IL-23 and IFN-γ, or a biologically active fragment thereof, or a functionally equivalent molecule thereof, wherein the at least one cytokine selected from the group consisting of IL-5, IL-12, IL-23 and IFN-γ, or a biologically active fragment thereof, or a functionally equivalent molecule thereof has been added exogenously to the medium in which the CD4$^+$,CD25$^+$ T cells are cultured. The at least one cytokines selected from the group consisting of IL-5, IL-12, IL-23 and IFN-γ, or a biologically active fragment thereof, or a functionally equivalent molecule thereof, may be constituents of a composition comprising other cytokines, growth factors, nutrients and/or buffers. The at least one cytokines selected from the group consisting of IL-5, IL-12, IL-23 and IFN-γ, or a biologically active fragment thereof, or a functionally equivalent molecule thereof may be purified proteins, recombinant or otherwise, which are added directly to the medium in which the lymphocytes are cultured. Alternatively, the CD4$^+$,CD25$^+$ T cells activated to the specific antigen grown in vitro may be cultured in the presence of cells which overexpress the at least one cytokine selected from the group consisting of IL-5, IL-12, IL-23 and IFN-γ, or a biologically active fragment thereof, or a functionally equivalent molecule thereof, and which are co-cultured with the lymphocytes.

The CD4$^+$,CD25$^+$ T cells activated to the specific antigen may be contacted with the specific antigen in vitro in any manner which permits the lymphocyte to recognise the antigen. Typically, the CD4$^+$,CD25$^+$ T cells activated to the specific antigen are contacted with the specific antigen located on the surface of an antigen presenting cell. The specific antigen may be displayed on the surface of the antigen presenting cell associated with a class II major histocompatibility molecule. The antigen presenting cell may be any cell that expresses an antigen presenting molecule (typically class II MHC) and, typically, ligands required to facilitate activation of the CD4$^+$, CD25$^+$ T cells. Examples of ligands include ICAM1, ICAM2, LFA3, ligands for CD28 and CTLA-4 or any activation ligands. Examples of antigen presenting cells include dendritic cells, phagocytes, B-lymphocytes, Langerhans cells or unfractionated lymphocytes in which the proliferation of the stimulator cells is impaired (for example, by irradiation or mitomycin C treatment).

Alternatively, the CD4$^+$,CD25$^+$ T cell activated with the specific antigen may be contacted with the specific antigen in a synthetic antigen presenting system such as that described in, for example, U.S. Pat. No. 6,828,150 or 6,787,154.

In one embodiment, the method of increasing tolerance to a specific antigen in a subject in need thereof comprises the further step of administering an effective amount of at least one cytokine selected from the group consisting of IL-5, IL-12, IL-23 and IFN-γ, or a biologically active fragment thereof, or a functionally equivalent molecule thereof, simultaneously with, or subsequent to, administering the CD4$^+$, CD25$^+$ T cells activated to the specific antigen. The method of increasing tolerance to a specific antigen in a subject may further comprise administering an effective amount of IL-13, a biologically active fragment thereof, or a functionally equivalent molecule thereof.

In a fifth aspect, the invention provides a method of reducing tolerance to a specific antigen in a subject by reducing or eliminating the activity of one or more cytokines selected from the group consisting of IL-5, IL-12, IL-23 and IFN-γ, or a biologically active fragment thereof, or a functionally equivalent molecule thereof, in the subject to thereby decrease the ratio of CD4$^+$,CD25$^+$ T cells activated to the specific antigen relative to CD4$^+$,CD25$^-$ T cells.

The ratio of CD4$^+$,CD25$^+$ T cells activated to the specific antigen to CD4$^+$,CD25$^-$ T cells may be further decreased by administering to the subject an effective amount of an agent which increases production of CD4$^+$,CD25$^-$ T cells, and depletes CD4$^+$,CD25$^+$ T cells. Typically, the agent is IL-2, a biologically active fragment thereof, or a functionally equivalent molecule thereof, and/or IL-4, a biologically active fragment thereof, or a functionally equivalent molecule thereof. The agent may be an anti-CD25 antibody, typically an anti-CD25 monoclonal antibody.

The activity of IL-5, IL-12, IL-23 or IFN-γ may be reduced or eliminated by any means for reducing or eliminating the biological activity of a cytokine in a subject. For example, the activity of IL-5, IL-12, IL-23 or IFN-γ may be reduced or eliminated by administering an effective amount of an antagonist of IL-5, IL-12, IL-23 and/or IFN-γ. The antagonist may be any molecule which reduces or eliminates the activity of IL-5, IL-12, IL-23 and/or IFN-γ. Examples of suitable antagonists include antibody receptor molecules, antisense molecules, iRNA or siRNA molecules, or any other molecules which reduce or eliminate the biological activity of IL-5, IL-12, IL-23 or IFN-γ. Typically, the antagonist is an antibody. Typically, the antibody is a monoclonal antibody.

In a sixth aspect, the present invention provides a composition comprising CD4$^+$,CD25$^+$ T cells activated to a specific antigen together with a cytokine and/or pharmaceutically acceptable carrier wherein said CD4$^+$,CD25$^+$ T cells activated to a specific antigen have been cultured in the presence of at least one cytokine selected from the group consisting of IL-5, IL-12, IL-23 and IFN-γ, or a biologically active fragment thereof, or a functionally equivalent molecule thereof.

In a seventh aspect, the invention provides a method for treating or preventing in a subject in need thereof a disease resulting from an immune response to a specific antigen, the method comprising the step of administering to the subject a therapeutically effective amount of CD4$^+$,CD25$^+$ T cells activated to the specific antigen grown in vitro by culturing CD4$^+$,CD25$^+$ T cells activated to the specific antigen in vitro in the presence of at least one cytokine selected from the group consisting of IL-5, IL-12, IL-23 and IFN-γ, or a biologically active fragment thereof, or a functionally equivalent molecule thereof.

In one embodiment, the number of CD4$^+$ T cells in the subject is reduced prior to administering the CD4$^+$,CD25$^+$ T cells activated to the specific antigen. Typically, the number of CD4$^+$,CD25$^-$ T cells in the subject is reduced. The number of CD4$^+$ T cells may be reduced by any methods known in the art for reducing lymphocytes in a subject including irradiation, administration of antibodies against CD4, typically CD4$^+$,CD25$^-$ T cells, such as anti-CD3, anti-CD4, anti-CD45RB/RO, or administration of cytotoxic or alkylating agent therapy.

In one embodiment, the method comprises the further step of contacting the CD4$^+$,CD25$^+$ T cells activated to the specific antigen with the specific antigen in vitro. The CD4$^+$,CD25$^+$ T cells activated to the specific antigen may be contacted with the specific antigen in vitro prior to, or simultaneous with, culturing the T cells in the presence of the at least one cytokine selected from the group consisting of IL-5, IL-12, IL-23 and IFN-γ, or a biologically active fragment thereof, or a functionally equivalent molecule thereof. Typically, the T cells are cultured in the presence of the at least one cytokine selected from the group consisting of IL-5, IL-12, IL-23 and IFN-γ, or a biologically active fragment thereof, or a functionally equivalent molecule thereof, after contacting the lymphocyte with the specific antigen.

The disease may be any disease resulting from an immune response to one or more specific antigens. In one embodiment, the disease is associated with an immune response to an autoantigen, for example an autoimmune disease. Examples of the types of autoimmune disease that may be prevented or treated using the method of the present invention include, for example, type 1 insulin dependent diabetes mellitis, inflammatory bowel syndrome including ulcerative colitis and Crohn's disease, thrombotic thrombocytopenic purpura, Sjogren's syndrome, encephalitis, acute disseminated encephalomyelitis, Guillain Barre Syndrome, chronic inflammatory demyelination polyneuropathy, idiopathic pulmonary fibrosis/alveolitis, asthma, uveitis, iritis, optic neuritis, rheumatic fever, Reiter's syndrome, psoriasis, psoriatic arthritis, multiple sclerosis, progressive systemic sclerosis, primary biliary cirrhosis, pemphigus, pemphigoid, necrotising vasculitis, myasthenia gravis, polymyositis, sarcoidosis, granulomatosis, vasculitis, pernicious anemia, central nervous system inflammatory disorder, autoimmune haemolytic anaemia, Hashimoto's thyroiditis, Graves disease, habitual spontaneous abortions, Raynaud's syndrome, dermatomyositis, chronic active hepatitis, celiac disease, autoimmune complications of AIDS, atrophic gastritis, ankylosing spondylitis, Addison's disease, chronic demyelinating neuropathy, glomerulonephritis including membranous nephropathy, focal sclerosing glomerulonephritis and minimal change nephropathy, systemic lupus erythematosis, scleroderma, rheumatoid arthritis, juvenile arthritis.

In another embodiment, the disease is the result of an immune response to a non-self antigen in contact with the subject. This may be the case following, for example, transplantation of cells or tissue to the subject where the transplanted cells or tissue undergoes rejection by the immune system of the subject. Typically, the transplanted cells or tissue is allograft or xenograft cells or tissue. Examples of transplant cells or tissue include kidney, liver, heart, valves, lung, skin, pancreas, cornea, lens, bone marrow, muscle, connective tissue, vascular tissue, gastrointestinal tissue, nervous tissue, bone, stem cells or genetically modified cells. Genetically modified cells may be, for example, stem cells, that have been transfected with a therapeutic or other agent.

Alternatively, the disease may be the result of an immune response to an allergen in contact with the subject. Examples of diseases resulting from an allergen include asthma, eczema, atopic dermatitis, anaphylaxis, hayfever, allergic conjunctivitis, contact dermatitis, food allergy.

In an eighth aspect, the invention provides a composition when used for reducing or eliminating tolerance to a specific antigen in a subject, the composition comprising an antagonist of one or more of the cytokines selected from the group consisting of IL-5, IL-12, IL-23 and IFN-γ, or a biologically active fragment thereof, or a functionally equivalent molecule thereof.

The antagonist may be any molecule which reduces or eliminates the activity of IL-5, IL-12, IL-23 and/or IFN-γ, biologically active fragments thereof, or functionally equivalent molecules thereof. Examples of suitable antagonists include antibody receptor molecules, antisense molecules, iRNA or siRNA molecules, or any other molecules which reduce or eliminate the biological activity of IL-5, IL-12, IL-23 or IFN-γ, biologically active fragments thereof, or functionally equivalent molecules thereof. Typically, the antibody is a monoclonal antibody.

In a ninth aspect, the invention provides a method for treating or preventing in a subject in need thereof a disease resulting from tolerance to a specific antigen, the method comprising the step of administering to the subject a therapeutically effective amount of an antagonist of one or more cytokines selected from the group consisting of IL-5, IL-12, IL-23 and IFN-γ, or a biologically active fragment thereof, or a functionally equivalent molecule thereof.

In one embodiment, the method may further comprise the step of administering an effective amount of an antibody against $CD4^+,CD25^+$ T cells. Typically, the antibody is an anti-CD25 antibody.

The disease may be any disease resulting from tolerance to a specific antigen. Examples of such disease include cancer, chronic infection such as hepatitis B and C, leprosy, tuberculosis, cryptococcosis, herpes simplex.

The invention also contemplates a kit for use with the methods of the invention. A kit for assessing whether a subject comprises $CD4^+,CD25^+$ T cells capable of imparting tolerance to a specific antigen may comprise media and/or cytokines for incubating the sample of lymphocytes. The cytokines may be one or more of IL-5, IL-12, IL-23 or IFN-γ, or a biologically active fragment thereof, or a functionally equivalent molecule thereof.

A kit for increasing tolerance to a specific antigen may comprise one or more cytokines selected from the group consisting of IL-5, IL-12, IL-23 and IFN-γ, or a biologically active fragment thereof, or a functionally equivalent molecule thereof. The kit may further comprise a specific antigen in a form suitable for contacting $CD4^+,CD25^+$ T cells from a subject in vitro. For example, the kit may comprise a specific antigen on the surface of an antigen presenting cell. It will be appreciated by persons skilled in the art that the relevant part of the specific antigen may be incorporated into an appropriate MHC molecule on the surface of the antigen presenting cell. The kit may further comprise IL-13, a biologically active fragment thereof, or a functionally equivalent molecule thereof.

A kit for decreasing tolerance to a specific antigen may comprise an antagonist of one or more cytokines selected from the group consisting of IL-5, IL-12, IL-23 and IFN-γ, or a biologically active fragment thereof, or a functionally equivalent molecule thereof. The antagonist may be any molecule which reduces or eliminates the activity of IL-5, IL-12, IL-23 and/or IFN-γ, biologically active fragments thereof, or functionally equivalent molecules thereof. Examples of suitable antagonists include antibody receptor molecules, antisense molecules, IRNA or siRNA molecules, or any other molecules which reduce or eliminate the biological activity of IL-5, IL-12, IL-23 or IFN-γ, biologically active fragments thereof, or functionally equivalent molecules thereof. Typically, the antibodies are monoclonal antibodies. The kit may further comprise IL-2, a biologically active fragment thereof, or a functionally equivalent molecule thereof, and/or IL-4, a biologically active fragment thereof, or a functionally equivalent molecule thereof.

The kits described above may further comprise instructions for use of the kit.

The subject may be any subject which produces $CD4^+$, $CD25^+$ T cells. The subject may be a mammal. The mammal may be a human or non-human animal, such as rodent, non-human primate, cattle, pig, sheep, camel, goat, cat, dog or horse. Typically, the subject is a human.

In a tenth aspect, the invention provides a method of inducing tolerance to a specific antigen in a subject in need thereof, wherein the subject's immune system is exposed to the specific antigen, the method comprising administering to the subject:
(i) an effective amount of one or more cytokines selected from the group consisting of IL-2, a biologically active fragment thereof, or a functionally equivalent molecule thereof, and IL-4, a biologically active fragment thereof, or a functionally equivalent molecule thereof; and
(ii) an effective amount of at least one cytokine selected from the group consisting of IL-5, IL-12, IL-23 and IFN-γ, or a biologically active fragment thereof, or a functionally equivalent molecule thereof.

It is envisaged that administration of IL-2 and/or IL-4, or a biologically active fragment thereof, or a functionally equivalent molecule thereof, supports activation of naïve $CD4^+$, $CD25^+$ T cells in contact with the specific antigen, and the at least one cytokine selected from the group consisting of IL-5, IL-12, IL-23 and IFN-γ, or a biologically active fragment thereof, or a functionally equivalent molecule thereof, maintains and/or stimulates proliferation of $CD4^+,CD25^+$ T cells activated to a specific antigen.

The at least one cytokine of step (ii) may be administered simultaneously with, or subsequent to, administration of the one or more cytokines of step (i). Suitably, the at least one cytokine of step (ii) is administered subsequent to administration of the one or more cytokines of step (i). Typically, the at least one cytokine of step (ii) is administered between 24 hours and 1 week following administration of the one or more cytokines of step (i).

In one embodiment of the tenth aspect, the method comprises administering an effective amount of IL-2, a biologically active fragment thereof, or a functionally equivalent molecule thereof, and an effective amount of IL-12, IL-23 and/or IFN-γ, a biologically active fragment thereof, or a functionally equivalent molecule thereof.

In another embodiment of the tenth aspect, the method comprises administering an effective amount of IL-4, a biologically active fragment thereof, or a functionally equivalent molecule thereof, and an effective amount of IL-5, a biologically active fragment thereof, or a functionally equivalent molecule thereof.

In yet another embodiment of the tenth aspect, the method comprises administering an effective amount of IL-2, a biologically active fragment thereof, or a functionally equivalent molecule thereof, and/or IL-4, a biologically active fragment thereof, or a functionally equivalent molecule thereof, and an effective amount of at least one cytokine selected from the group consisting of IL-5, IL-12, IL-23 and IFN-γ, or a biologically active fragment thereof, or a functionally equivalent molecule thereof.

In another embodiment of the tenth aspect, the method further comprises the step of administering an effective amount of IL-13, a biologically active fragment thereof, or a functionally equivalent molecule thereof.

In an eleventh aspect, the invention provides a method of treating or preventing in a subject in need thereof a disease resulting from an immune response to an antigen, the method comprising administering to the subject:
  (i) an effective amount of one or more cytokines selected from the group consisting of IL-2, a biologically active fragment thereof, or a functionally equivalent molecule thereof, and IL-4, a biologically active fragment thereof, or a functionally equivalent molecule thereof; and
  (ii) an effective amount of at least one cytokine selected from the group consisting of IL-5, IL-12, IL-23 and IFN-γ, or a biologically active fragment thereof, or a functionally equivalent molecule thereof.

The at least one cytokine of step (ii) may be administered simultaneously with, or subsequent to, administration of the one or more cytokines of step (i). Suitably, the at least one cytokine of step (ii) is administered subsequent to administration of one or more cytokines of step (i). Typically, the at least one cytokine of step (ii) is administered between 24 hours and 1 week following administration of the one or more cytokines of step (i).

In one embodiment of the eleventh aspect, the method comprises administering an effective amount of IL-2, or a biologically active fragment thereof, or a functionally equivalent molecule thereof, and an effective amount of at least one cytokine selected from the group consisting of IL-12, IL-23 and IFN-γ, or a biologically active fragment thereof, or a functionally equivalent molecule thereof.

In another embodiment of the eleventh aspect, the method comprises administering an effective amount of IL-4, a biologically active fragment thereof, or a functionally equivalent molecule thereof, and an effective amount of IL-5, a biologically active fragment thereof, or a functionally equivalent molecule thereof.

In yet another embodiment of the eleventh aspect, the method comprises administering an effective amount of IL-2, a biologically active fragment thereof, or a functionally equivalent molecule thereof, and/or IL-4, a biologically active fragment thereof, or a functionally equivalent molecule thereof, and at least one cytokine selected from the group consisting of IL-5, IL-12, IL-23 and IFN-γ, or a biologically active fragment thereof, or a functionally equivalent molecule thereof.

In another embodiment of the eleventh aspect, the method further comprises the step of administering an effective amount of IL-13, a biologically active fragment thereof, or a functionally equivalent molecule thereof.

In one embodiment of the eleventh aspect, the method may comprise, prior to step (ii), the steps of:
  (a) obtaining from the subject a sample of lymphocytes comprising CD4$^+$,CD25$^+$ T cells; and
  (b) determining whether the sample comprises CD4$^+$, CD25$^+$ T cells that are responsive to one or more cytokines selected from the group consisting of IL-5, IL-12, IL-23 and IFN-γ, or a biologically active fragment thereof, or a functionally equivalent molecule thereof.

In such embodiments, step (ii) typically comprises administering an effective amount of a cytokine selected from the group consisting of IL-5, IL-12, IL-23 and IFN-γ, or a biologically active fragment thereof, or a functionally equivalent molecule thereof, to which the CD4$^+$,CD25$^+$ T cells have been determined to be responsive.

In one embodiment, responsiveness of the CD4$^+$,CD25$^+$ T cells from the sample to the one or more cytokines is determined by detecting the expression of a receptor for the one or more cytokines. Expression of the receptor for the one or more cytokines may be detected using an antibody to the receptor. Expression of the receptor for the one or more cytokines may be detected by detecting expression of RNA for the receptor. For example, assay using PCR, RT-PCR, northern blot analysis etc. may be used to detect mRNA that encodes the receptor for the one or more cytokines.

In another embodiment, responsiveness to the one or more cytokines may be determined by assessing proliferation of the sample in the presence of the one or more cytokines selected from the group consisting of IL-5, IL-12, IL-23 and IFN-γ, or a biologically active fragment thereof, or a functionally equivalent molecule thereof. For example, the sample may be incubated in the presence of the one or more cytokines selected from the group consisting of IL-5, IL-12, IL-23 and IFN-γ, or a biologically active fragment thereof, or a functionally equivalent molecule thereof, typically also in the presence of the specific antigen, whereby proliferation of CD4$^+$,CD25$^+$ T cells in the presence of the one or more cytokines indicates that the CD4$^+$,CD25$^+$ T cells are responsive to the one or more cytokines selected from the group consisting of IL-5, IL-12, IL-23 and IFN-γ, or a biologically active fragment thereof, or a functionally equivalent molecule thereof.

The disease may be any disease resulting from an immune response to one or more specific antigens. In one embodiment, the disease is associated with an immune response to an autoantigen, for example an autoimmune disease. Examples of the types of autoimmune disease that may be prevented or treated using the method of the present invention include, for example, type 1 insulin dependent diabetes mellitis, inflammatory bowel syndrome including ulcerative colitis and Crohn's disease, thrombotic thrombocytopenic purpura, Sjogren's syndrome, encephalitis, acute disseminated encephalomyelitis, Guillain Barre Syndrome, chronic inflammatory demyelination polyneuropathy, idiopathic pulmonary fibrosis/alveolitis, asthma, uveitis, iritis, optic neuritis, rheumatic fever, Reiter's syndrome, psoriasis, psoriatic arthritis, multiple sclerosis, progressive systemic sclerosis, primary biliary cirrhosis, pemphigus, pemphigoid, necrotising vasculitis, myasthenia gravis, polymyositis, sarcoidosis, granulomatosis, vasculitis, pernicious anemia, central nervous system inflammatory disorder, autoimmune haemolytic anaemia, Hashimoto's thyroiditis, Graves disease, habitual spontaneous abortions, Raynaud's syndrome, dermatomyositis, chronic active hepatitis, celiac disease, autoimmune complications of AIDS, atrophic gastritis, ankylosing spondylitis, Addison's disease, chronic demyelinating neuropathy, glomerulonephritis including membranous nephropathy, focal sclerosing glomerulonephritis and minimal change nephropathy, systemic lupus erythematosis, scleroderma, rheumatoid arthritis, juvenile arthritis.

In another embodiment, the disease is the result of an immune response to a non-self antigen in contact with the subject. This may be the case following, for example, transplantation of cells or tissue to the subject where the transplanted cells or tissue undergoes rejection by the immune system of the subject. Typically, the transplanted cells or tissue is allograft or xenograft cells or tissue. Examples of transplant cells or tissue include kidney, liver, heart, valves, lung, skin, pancreas, cornea, lens, bone marrow, muscle, connective tissue, vascular tissue, gastrointestinal tissue, nervous tissue, bone, stem cells or genetically modified cells. Genetically modified cells may be, for example, autologous cells, including skin cells, which have been transfected with a therapeutic or other agent.

Alternatively, the disease may be the result of an immune response to an allergen in contact with the subject. Examples of diseases resulting from an allergen include asthma, eczema, atopic dermatitis, anaphylaxis, hayfever, allergic conjunctivitis, contact dermatitis, food allergy, drug or other chemical allergy, venom allergy.

In a twelfth aspect, the invention provides a method of inducing tolerance to a specific antigen in a subject in need thereof, comprising administering to the subject an effective amount of one or more cytokines selected from the group consisting of IL-5, IL-12, IL-23 and IFN-γ, or a biologically active fragment thereof, or a functionally equivalent molecule thereof.

Typically, the method does not comprise administering anti CD-3 antibody.

In some embodiments the subject's immune system is exposed to the specific antigen. In embodiments where the subject's immune system is exposed to the specific antigen, the method may comprise:
  (a) obtaining from the subject a sample of lymphocytes comprising CD4$^+$,CD25$^+$ T cells;
  (b) determining whether the sample comprises CD4$^+$, CD25$^+$ T cells that are responsive to one or more cytokines selected from the group consisting of IL-5, IL-12, IL-23 and IFN-γ, or a biologically active fragment thereof, or a functionally equivalent molecule thereof; and
  (c) administering an effective amount of the one or more cytokines selected from the group consisting of IL-5, IL-12, IL-23 and IFN-γ, or a biologically active fragment thereof, or a functionally equivalent molecule thereof, to which the CD4$^+$,CD25$^+$ T cells are responsive.

In a thirteenth aspect, the invention provides a method of treating or preventing in a subject in need thereof a disease resulting from an immune response to a specific antigen, the method comprising administering an effective amount of one or more cytokines selected from the group consisting of IL-5, IL-12, IL-23 and IFN-γ, or a biologically active fragment thereof, or a functionally equivalent molecule thereof.

In one embodiment, the method comprises the steps of:
  (a) obtaining from the subject a sample of lymphocytes comprising CD4$^+$,CD25$^+$ T cells;
  (b) determining whether the sample comprises CD4$^+$, CD25$^+$ T cells that are responsive to one or more cytokines selected from the group consisting of IL-5, IL-12, IL-23 and IFN-γ, or a biologically active fragment thereof, or a functionally equivalent molecule thereof; and
  (c) administering an effective amount of the one or more cytokines selected from the group consisting of IL-5, IL-12, IL-23 and IFN-γ, or a biologically active fragment thereof, or a functionally equivalent molecule thereof, to which the CD4$^+$,CD25$^+$ T cells are responsive.

The responsiveness of the CD4$^+$,CD25$^+$ T cells from the sample to the one or more cytokines may be determined by detecting the expression of a receptor for the one or more cytokines. Expression of the receptor for the one or more cytokines may be detected using an antibody to the receptor. Expression of the receptor for the one or more cytokines selected from the group consisting of IL-5, IL-12, IL-23 and IFN-γ, or a biologically active fragment thereof, or a functionally equivalent molecule thereof may be detected by detecting expression of RNA for the receptor. For example, assay using PCR, RT-PCR, northern blot analysis etc. may be used to detect mRNA that encodes the receptor for the one or more cytokines selected from the group consisting of IL-5, IL-12 and IFN-γ, or a biologically active fragment thereof, or a functionally equivalent molecule thereof.

The responsiveness to the one or more cytokines selected from the group consisting of IL-5, IL-12, IL-23 and IFN-γ, or a biologically active fragment thereof, or a functionally equivalent molecule thereof may be determined by assessing proliferation of the sample in the presence of the one or more cytokines selected from the group consisting of IL-5, IL-12, IL-23 and IFN-γ, or a biologically active fragment thereof, or a functionally equivalent molecule thereof. For example, the sample may be incubated in the presence of the one or more cytokines selected from the group consisting of IL-5, IL-12, IL-23 and IFN-γ, or a biologically active fragment thereof, or a functionally equivalent molecule thereof, typically also in the presence of the specific antigen, whereby proliferation of CD4$^+$,CD25$^+$ T cells in the presence of the one or more cytokines selected from the group consisting of IL-5, IL-12, IL-23 and IFN-γ, or a biologically active fragment thereof, or a functionally equivalent molecule thereof indicates that the CD4$^+$,CD25$^+$ T cells are responsive to the one or more cytokines selected from the group consisting of IL-5, IL-12, IL-23 and IFN-γ, or a biologically active fragment thereof, or a functionally equivalent molecule thereof.

In one embodiment, the method comprises the step, prior to or simultaneously with administering the one or more cytokines selected from the group consisting of IL-5, IL-12, IL-23 and IFN-γ, or a biologically active fragments thereof, or a functionally equivalent molecule thereof, the step of administering to the subject an effective amount of one or more cytokines selected from the group consisting of IL-2 and IL-4, biologically active fragments thereof, and functionally equivalent molecules thereof.

In one embodiment of the twelfth or thirteenth aspect, the method further comprises the step of administering an effective amount of IL-13, a biologically active fragment thereof, or a functionally equivalent molecule thereof.

The disease resulting from an immune response to an antigen may be any of the diseases resulting from an immune response listed above.

In a fourteenth aspect, the invention provides a kit when used with the method of the ninth, tenth or twelfth aspect, the kit comprising IL-2, a biologically active fragment thereof, or a functionally equivalent molecule thereof, and/or IL-4, a biologically active fragment thereof, or a functionally equivalent molecule thereof, and/or at least one cytokine selected from the group consisting of IL-5, IL-12, IL-23 and IFN-γ, or a biologically active fragment thereof, or a functionally equivalent molecule thereof. The kit may further comprise IL-13. The kit may further comprise instructions for use. It is also envisaged that any of the above methods for increasing tolerance to a specific antigen may be applied in methods of treatment of subjects which involve introducing a foreign entity into the subject for delivery of an agent, typically a therapeutic agent. For example, the methods of the invention may be used to increase tolerance to a virus used for gene therapy, or to other gene delivery vehicles which otherwise elicit an immune response.

In a fifteen aspect, the invention provides the use of $CD4^+$, $CD25^+$ T cells activated to a specific antigen grown in vitro by the method of the third aspect in the manufacture of a medicament for increasing tolerance in a subject in need thereof.

In a sixteenth aspect, the invention provides the use of an antagonist of IL-5, IL-12, IL-23 or IFN-γ in the manufacture of a medicament for reducing tolerance to a specific antigen in a subject.

In a seventeenth aspect, the invention provides the use of $CD4^+$,$CD25^+$ T cells activated to a specific antigen grown in vitro by the method of the third aspect in the manufacture of a medicament for treating or preventing in a subject in need thereof a disease resulting from an immune response to the specific antigen.

In an eighteenth aspect, the invention provides the use of $CD4^+$,$CD25^+$ T cells activated to a specific antigen grown in vitro by the method of the third aspect in the manufacture of a medicament for treating or preventing in a subject in need thereof a disease resulting from tolerance to the specific antigen.

In a nineteenth aspect, the invention provides the use of one or more cytokines selected from the group consisting of IL2, IL-4, a biologically active fragment thereof, or a functionally equivalent molecule thereof, in the manufacture of a medicament for the treatment of a subject to induce tolerance in the subject, the treatment comprising administering an effective amount of the medicament and an effective amount of at least one cytokine selected from the group consisting of IL-5, IL-12, IL-23 and IFN-γ, a biologically active fragment thereof, or a functionally equivalent molecule thereof.

In a twentieth aspect, the invention provides the use of one or more cytokines selected from the group consisting of IL-5, IL-12, IL-23 and IFN-γ, a biologically active fragment thereof, or a functionally equivalent molecule thereof, in the manufacture of a medicament for the treatment of a subject to induce tolerance in the subject, the treatment comprising administering an effective amount of the medicament and an effective amount of at least one cytokine selected from the group consisting of IL-2 and IL-4, a biologically active fragment thereof, or a functionally equivalent molecule thereof.

In a twenty-first aspect, the invention provides the use of one or more cytokines selected from the group consisting of IL-5, IL-12, IL-23 and IFN-γ, a biologically active fragment thereof, or a functionally equivalent molecule thereof, in the manufacture of a medicament for increasing the tolerance to a subject in need thereof.

In a twenty-second aspect, the invention provides the use of one or more cytokines selected from the group consisting of IL-5, IL-12, IL-23 and IFN-γ, a biologically active fragment thereof, or a functionally equivalent molecule thereof, in the manufacture of a medicament for treating or preventing in a subject in need thereof a disease resulting from an immune response to a specific antigen.

In a twenty-third aspect, the invention provides a method of activating $CD4^+$,$CD25^+$ T cells to a specific antigen, the method comprising:
(a) contacting naïve $CD4^+$,$CD25^+$ T cells with the specific antigen; and
(b) culturing the $CD4^+$,$CD25^+$ T cells in the presence of IL-2, a biologically active fragment thereof, or a functionally equivalent molecule thereof, and/or IL-4, a biologically active fragment thereof, or a functionally equivalent molecule thereof.

In a twenty-fourth aspect, the invention provide a method of culturing $CD4^+$,$CD25^+$ T cells activated to a specific antigen, the method comprising culturing the $CD4^+$,$CD25^+$ T cells in the presence of at least one cytokine selected from the group consisting of IL-5, IL-12, IL-23 and IFN-γ, a biologically active fragment thereof, or a functionally equivalent molecule thereof.

BRIEF DESCRIPTION OF THE FIGURES

FIG. 5B is graphs showing proliferation of CD4$^+$,CD25$^+$ T cells, CD4$^+$,CD25$^-$ T cells and CD4$^+$,CD25$^-$ T cells admixed with CD4$^+$,CD25$^+$ T cells in a ratio of 1:1 following incubation in the presence of self antigen (black) or alloantigen (grey) The effects of antibodies to block IL-5, TGF-β or IL-10 were compared to a control antibody Mog-Ig2a.

DETAILED DESCRIPTION OF THE INVENTION

Figure 1A:
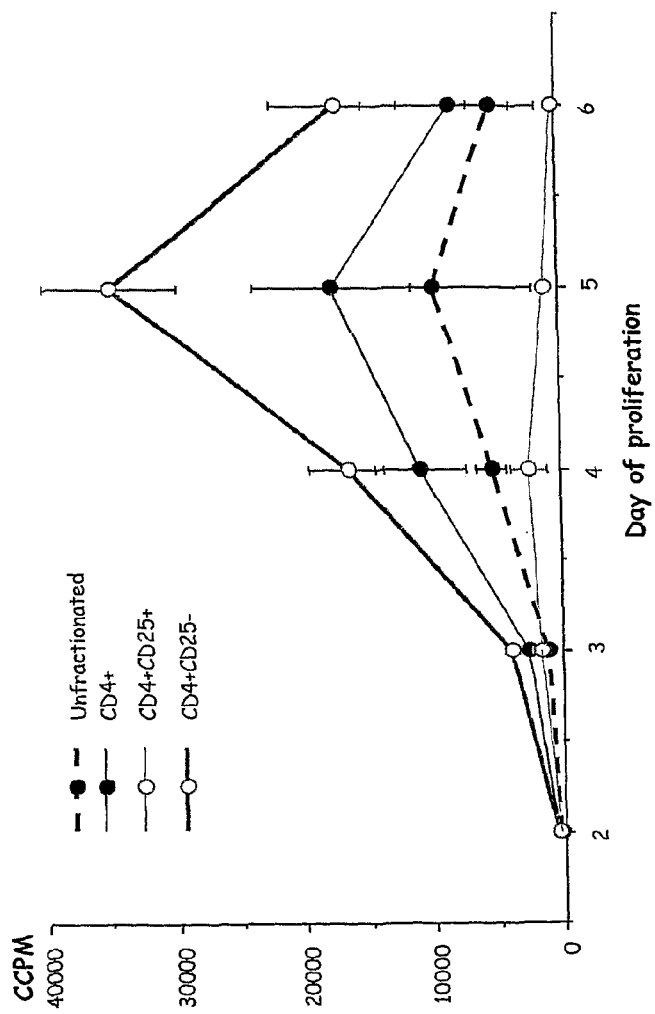
FIG. 1A is a graph of the proliferation of naïve unfractionated lymphocytes (dashed line and filled in circles), naïve $CD4^+$ T cell/lymphocytes (hard line, filled in circles), naïve $CD4^+$,$CD25^+$ T cells (open circles thin line), and naïve $CD4^+$,$CD25^-$ T cells (open circles thick line). Proliferation assayed at days 2, 3, 4, 5 and 6 following contacting the lymphocytes with an alloantigen.

Tolerance is a critically important immunological discriminatory process without which a serious disease state might exist. As described above, there are circumstances when abnormal induction of an immune response leads to autoimmune diseases, and the re-establishment of tolerance would be desirable. There are also special circumstances when induction of tolerance is desirable, for example, following organ transplantation.

There are also circumstances where induction of tolerance to a specific antigen is not desirable, for example, in the case of chronic infection or cancer. In such circumstances, it would be desirable to reduce or break tolerance to the antigen of the infectious agent or tumour to which a subject has developed tolerance to thereby reduce or eliminate the chronic infection, or the tumour.

In one aspect, the invention relates to a method of assessing whether a subject comprises CD4$^+$,CD25$^+$ T cells that have been activated to a specific antigen. The CD4$^+$,CD25$^+$ T cells activated to a specific antigen are capable of imparting tolerance to a specific antigen. Thus, the invention also relates to a method of determining whether a subject is tolerant, or capable of becoming tolerant, to a specific antigen. As used herein, the term "tolerant" refers to the process of suppressing a portion of the immune system that recognises an antigen as being foreign. It will be appreciated by persons skilled in the art that the term "tolerance" as used herein has the same meaning as "immune tolerance". Therefore, the phrase "tolerant to a specific antigen" will be understood by those skilled in the art as meaning a state of immune unresponsiveness or reduced immune responsiveness to the specific antigen without a prolonged generalised immunosuppression. Thus, a subject tolerant to a specific antigen is capable of eliciting an immune response to antigens foreign to the subject other than the specific antigen. A subject that is "capable of becoming tolerant to a specific antigen" is one whose immune system contains the lymphocytes necessary for inducing tolerance to a specific antigen but which has not yet progressed to full tolerance to the specific antigen.

The subject may be any subject which produces CD4$^+$, CD25$^+$ T cells. For many years, animals of various species such as, for example mice and rats, have been used as models for studying the human immune system as well as the immune system of other mammals. This has been the case because findings in mice and rats, for example, have been directly applicable to models of the immune system of humans and other mammals. Accordingly, results obtained in studies of mice, rats and other mammals are directly applicable to humans and other mammals (Kostakis et al. IRCS Med Sci Libr Compend 1977, 5, 280).

The method of the invention for assessing whether a subject comprises CD4$^+$,CD25$^+$ T cells that have been activated to a specific antigen, comprises obtaining from the subject a sample of lymphocytes comprising CD4$^+$,CD25$^+$ T cells, incubating at least one portion of the sample of lymphocytes so as to promote distinction of CD4$^+$,CD25$^+$ T cells that have been activated to the specific antigen from CD4$^+$,CD25$^+$ T cells that have not been activated to the specific antigen, and thereafter determining whether CD4$^+$,CD25$^+$ T cells that have been activated to the specific antigen are present in the sample.

The at least one portion of the sample may be incubated in any manner that promotes a distinction of CD4$^+$,CD25$^+$ T cells that have been activated to the specific antigen from other CD4$^+$,CD25$^+$ T cells. The distinction may, for example, be increased or decreased proliferation or survival of CD4$^+$, CD25$^+$ T cells activated to the specific antigen relative to other CD4$^+$,CD25$^+$ T cells. This distinction may, for example, be increased or decreased expression of messenger RNA species by the CD4$^+$,CD25$^+$ T cells activated to the specific antigen relative to other CD4$^+$,CD25$^+$ T cells.

Typically, the subject is a subject whose immune system is exposed to the specific antigen. The term "lymphocyte" will be understood by those skilled in the art to refer to the cells of the immune system that are responsible for initiating and controlling the specific immune response. Such cells include T lymphocytes, also known as T cells. CD4$^+$ lymphocytes are T lymphocytes. The sample of lymphocytes may be, for example, mixed peripheral lymphocytes, isolated CD4$^+$ lymphocytes or isolated CD4$^+$,CD25$^+$ lymphocytes. Typically, the sample of lymphocytes is peripheral blood lymphocytes.

The sample of lymphocytes is typically isolated from peripheral blood lymphocytes. The isolation and characterisation of a population of T lymphocyte cells in vitro has been described in a number of prior art documents, for example, those shown in U.S. Pat. No. 5,622,853 and International Patent Application No. WO00/20445; however, any known procedure for isolating lymphocytes may be used. Briefly, in one optional approach a blood sample containing T-cells is taken from a mammal. Peripheral blood lymphocytes are then isolated from the blood sample using the methods for T lymphocyte isolation referred to above. For example, peripheral blood lymphocytes may be isolated by Ficoll-Hypaque gradient centrifugation (Pharmacia, Piscataway, N.J.).

Following isolation of peripheral blood lymphocytes, CD4$^+$,CD25$^+$ T cells may be isolated from the population of isolated peripheral blood lymphocytes. As used herein, "CD4$^+$,CD25$^+$ T cell" is any lymphocyte that expresses on its surface the cluster of differentiation markers known as CD4 and CD25. A CD4$^+$,CD25$^+$ T cell is also known as CD4$^+$, CD25$^+$ lymphocyte. The CD4$^+$,CD25$^+$ T cell may also express other markers which may aid in the isolation of CD4+, CD25+ T cells such as, for example, CD45RO−,RB−. Naïve CD4+,CD25+ T cells may express L-selectin. Typically, the CD4+,CD25+ T cells are CD4+,CD25+high T cells.

Typically, CD4+,CD25+ T cells are isolated by positive enrichment of CD25+ T cells using an anti-CD25 antibody. For example, CD4+,CD25+ T cells may be isolated by means of multiparameter flow cytometric analysis using one or more fluorescent labelled anti-CD25 antibodies. This method includes the analysis of both light scatter parameters as well as one or more fluorescence parameters. Other methods of isolation include, for example, magnetic bead based separation as previously described in U.S. Pat. No. 517,101. Flow cytometric analysis may be performed, for example, on a FACScan™ flow cytometer or a FACStar™ plus cell sorter (both available from Becton Dickinson Immunocytometry Systems, "BDIS"). Data acquisition may be performed with FACScan Research software and FACStar Plus software (BDIS). Forward light scatter, orthogonal light scatter and three fluorescence signals are determined for each cell and stored in listmode data files. Each experiment measures approximately 30,000 cells, although it will be appreciated that the number of cells may vary greatly depending on the subject and available lymphocytes. The analysis of the listmode data files is preferably performed with Paint-A-Gate, TM software (BDIS). (See U.S. Pat. No. 4,845,653). To increase the orthogonal light scattering resolution, the orthogonal light scattering signals may be transformed by using a polynomial function as described in U.S. patent application Ser. No. 517,096. For light microscope examination, 10,000 sorted cells are centrifuged for five minutes at 200 g and resuspended in 100 ml RPMI 1640 containing 10% FCS. Cytospin preparations are made on a Shandon cyto-centrifuge (Southern Products Ltd). Slides containing sorted cells may be stained with Wright Giemsa stain (Sigma).

CD4+,CD25+ T cells may be fluorescently labelled for identification and/or isolation using a variety of monoclonal antibodies available from BDIS. Antibodies may be fluorescent labelled with one of the following fluorochromes: phycoerythrin ("PE"), fluorescein isothiocyanate ("FITC") and peridinin chlorophyll complex ("PerCp"). For a description of PE and PerCp, see U.S. Pat. Nos. 4,520,110 and 4,876,190 respectively. The monoclonal antibodies which may be used include, for example: anti-CD4 FITC, PE or PerCp; anti-CD25 PE. (All antibodies commercially available from BDIS).

CD4+,CD25− T cells may be isolated by any methods known in the art. For example, CD4+,CD25− T cells may be isolated by depleting CD4+ T cells of CD4+,CD25+ T cells. In some embodiments, the at least one portion of the sample of lymphocytes is contacted with the specific antigen prior to, or simultaneously with, incubating the at least one portion of the sample in the absence of cytokines capable of stimulating activation of CD4+,CD25+ T cells or of prolonging survival or supporting proliferation of activated CD4+,CD25+ T cells, or the presence of and one or more cytokines capable of prolonging survival or supporting proliferation of activated CD4+,CD25+ T cells. In some embodiments, the at least one portion is contacted with the specific antigen by incubating in the presence of specific antigen. The at least one portion of the sample may be incubated in the presence of the specific antigen in any manner that permits lymphocytes in the sample to contact the specific antigen and to recognise the specific antigen. As used herein, the term "contacting" or "contacted" refers to contacting a lymphocyte with an antigen in a manner which permits the lymphocyte to recognise the antigen. In other words, the at least one portion of the sample of lymphocytes are contacted with the specific antigen in a manner which would permit activation of T cells in the sample.

Typically, the at least one portion of the sample of lymphocytes is contacted with the specific antigen by presenting the specific antigen to the lymphocytes on the surface of a stimulator cell such as, for example, an antigen presenting cell. Typically, the specific antigen is presented to the lymphocytes associated with a major histocompatibility (MHC) molecule (typically class II) on the surface of an antigen presenting cell. As defined herein, a "stimulator cell" is a cell which is capable of presenting an antigen to a lymphocyte in a manner in which the lymphocyte can recognise the antigen. For example, the stimulator cell may be a tumour cell (see for example U.S. Pat. No. 5,342,774, Knuth et al. (Proc. Natl. Acad. Sci. USA 86: 2804-2808, 1989) and Van Den Eynde et al. (Int. J. Cancer 44: 634-640, 1989) or the stimulator cell may be an antigen presenting cell.

An "antigen presenting cell" will be understood by those skilled in the art to be a cell which contributes to the induction of an immune response by presenting antigen to T-lymphocytes. Antigen presenting cells may be dendritic cells, mononuclear phagocytes, B-lymphocytes, unfractionated lymphocytes or Langerhans cells. The antigen presenting cells may be isolated from, for example, bone marrow, blood, thymus, epidermis, liver or fetal liver. The antigen presenting cells may be unfractionated lymphocytes in which stimulator cells have been impaired by treatment with, for example, irradiation or mitomycin C. The antigen presenting cells may be cells expressing the relevant antigen presenting molecule (eg. Class II MHC) and other ligands that are required to facilitate binding and activation of naïve CD4+,CD25+ T cells. Suitable ligands include ICAM1, ICAM2, LFA3, and the ligands for CD28 and CTL-A and other activation ligands or part of the antigen that is presented on self MHC molecules and recognised by T cells activated in an autoimmune response.

The at least one portion of the sample of lymphocytes may be contacted with the specific antigen using synthetic antigen presenting systems, such as those described in U.S. Pat. Nos. 6,828,150 or 6,787,154.

As will be apparent to those skilled in the art, a sample of lymphocytes may be contacted with other antigens by the same manner as described above for contacting the at least one portion of the sample of lymphocytes with the specific antigen.

The specific antigen may be any substance which elicits an immune response in a subject that is not tolerant to the specific antigen. The specific antigen may or may not be derived from the subject. The specific antigen may be an autoantigen, which will be understood by those skilled in the art as referring to an antigen that can elicit a reaction in persons with a propensity to allergy. The specific antigen may be an alloantigen, which will be understood by those skilled in the art as referring to an antigen derived from a subject of the same species. The specific antigen may be a xenoantigen, which will be understood by those skilled in the art as referring to an antigen derived from a subject of a different species.

The specific antigen may be an allergen.

As mentioned above, the specific antigen may be any substance which elicits an immune response in a subject that is not tolerant to the antigen. For example, a typical alloantigen may be donor transplant cells or tissue from another human. A typical xenoantigen may be transplant cells or tissue from a non-human animal such as, for example, a pig. Donor transplant cells or tissue from humans or non-human animals may include kidney, liver, heart, lung, skin, pancreas, cornea, lens, bone marrow, muscle, connective tissue, vascular tissue, gastrointestinal tissue, nervous tissue, bone, valves, stem cells, cells, such as stem cells, transfected with an agent such as a therapeutic agent.

The antigen presenting cell may be isolated with the specific antigen already presented on the surface of the cell. For example, antigen presenting cells isolated from, for example, the spleen of a subject suffering from an autoimmune disease will have the autoantigen presented on the surface of the cell. In the case of tissue transplantation, antigen presenting cells isolated from the tissue of a transplant donor will have the alloantigen presented on the surface of such cells. For example, the antigen presenting cells may be frozen or stored spleen or lymph node cells from the cadaver of a donor, or peripheral blood cells from a living donor. Alternatively, empty MHC molecules of antigen presenting cells isolated from the subject may be loaded with specific antigens as described in U.S. Pat. No. 5,731,160 whereby empty MHC molecules are loaded with immunogenic exogenous peptides of approximately 8 to 18 amino acids in length.

Antigen presenting cells may be isolated from blood or tissue by methods known in the art. For example, B-lymphocytes can be purified from a mixed population of cells (e.g. other cell types in peripheral blood or spleen) by standard cell separation techniques. For example, adherent cells can be removed by culturing spleen cells on plastic dishes and recovering the non-adherent cell population. T-lymphocytes can be removed from a mixed population of cells treated with an anti-T cell antibody (e.g. anti-CD3 (see for example WO 01/37860), anti-CD2) and complement. In one embodiment, resting B-lymphocytes are used as the antigen presenting cell. Resting B-lymphocytes can be isolated by methods based on the small size and density of the B-lymphocytes. Resting lymphoid cells may be isolated by counterflow centrifugal elutriation as described in Tony, H-P, Parker, D. C. (1985) J. Exp. Med. 161: 223-241. Using counterflow centrifugal elutriation, a small, resting lymphoid cell population depleted of cells which can activate T cell responses can be obtained as described in U.S. Pat. No. 6,312,692.

In another embodiment, unfractionated lymphocytes may be used as the antigen presenting cell. Typically, the unfractionated lymphocytes are treated to impair proliferation of stimulator cells. Examples of treatments suitable for impairing proliferation of stimulator cells include irradiation, or treatment with mitomycin C.

In one embodiment of the method of the first aspect of the present invention, simultaneous with, or following contacting the at least one portion of the sample of lymphocytes with the specific antigen, the at least one portion of the sample of lymphocytes is incubated:

(i) in the absence of cytokines capable of stimulating activation of $CD4^+,CD25^+$ T cells or of prolonging survival or supporting proliferation of activated $CD4^+,CD25^+$ T cells; or (ii) in the presence of at least one cytokine selected from the group consisting of IL-5, IL-12, IL-23 and IFN-$\gamma$, or a biologically active fragment thereof, or a functionally equivalent molecule thereof.

In some embodiments, a portion of the sample is contacted with the specific antigen and incubated in the absence of cytokines capable of stimulating activation of $CD4^+,CD25^+$ T cells or of prolonging survival or supporting proliferation of activated $CD4^+,CD25^+$ T cells, and another portion of the sample is contacted with the specific antigen and incubated in the presence of at least one cytokine selected from the group consisting of IL-5, IL-12, IL-23 and IFN-$\gamma$, or a biologically active fragment thereof, or a functionally equivalent molecule thereof.

It will be understood by those skilled in the art that the expression "in the absence of cytokines capable of stimulating activation of $CD4^+,CD25^+$ T cells or of prolonging survival or supporting proliferation of activated $CD4^+,CD25^+$ T cells" means that those cytokines that are capable of stimulating activation of $CD4^+,CD25^+$ T cells (such as IL-2 or IL-4, or a biologically active fragment thereof, or a functionally equivalent molecule thereof) or of prolonging survival or supporting proliferation of activated $CD4^+,CD25^+$ T cells (such as IL-5, IL-12, IL-23 and IFN-$\gamma$, or a biologically active fragment thereof, or a functionally equivalent molecule thereof), are either not present, or are present in such low amounts that they do not have a biological effect. As used herein, the expression "biological effect" refers to the ability to activate $CD4^+,CD25^+$ T cells or to prolong survival or support proliferation of activated $CD4^+,CD25^+$ T cells. It will also be understood that the expression "in the presence of at least one cytokine selected from the group consisting of IL-5, IL-12, IL-23 or IFN-$\gamma$, or a biologically active fragment thereof, or a functionally equivalent molecules thereof" means that one or more of IL-5, IL-12, IL-23 or IFN-$\gamma$, or a biologically active fragment thereof, or a functionally equivalent molecule thereof, is present in a sufficient amount to maintain survival and/or promote proliferation of activated $CD4^+,CD25^+$ T cells. The expression "biologically active fragment thereof" in relation to IL-5, IL-12, IL-23 or IFN-$\gamma$ refers to any fragment of these cytokines which has the ability to maintain survival or support proliferation of $CD4^+,CD25^+$ T cells activated to a specific antigen, and in relation to IL-2 and IL-4 refers to any fragment of these cytokines which has the ability to support activation of naïve $CD4^+,CD25^+$ T cells. For example, a biologically active fragment of IL-5 may be any portion of the IL-5 molecule which has the ability to maintain survival and/or support proliferation of $CD4^+,CD25^+$ T cells activated to a specific antigen.

It is envisaged by the inventors that as the cytokines IL-5, IL-12, IL-23 and/or IFN-$\gamma$ are capable of prolonging survival, or supporting proliferation, of activated $CD4^+,CD25^+$ T cells, any molecules which interact with the IL-5, IL-12, IL-23 or IFN-$\gamma$ receptor of the activated $CD4^+,CD25^+$ T cells to activate the same signal transduction pathways as IL-5, IL-12, IL-23 or IFN-$\gamma$ will also be effective in prolonging survival and/or supporting proliferation of activated $CD4^+,CD25^+$ T cells. As used herein, the term "functionally equivalent molecule" refers to a molecule that is not a cytokine or a biologically active fragment thereof, but which has the same biological activity as a cytokine. Accordingly, the expression "functionally equivalent molecule thereof" in relation to IL-5, IL-12, IL-23 or IFN-$\gamma$ refers to a molecule that is not IL-5, IL-12, IL-23 or IFN-$\gamma$, or a biologically active fragment thereof, but which is nonetheless a ligand for the IL-5, IL-12, IL-23 or IFN-$\gamma$ receptor and which is capable of prolonging survival and/or supporting proliferation of $CD4^+,CD25^+$ T cells activated to a specific antigen. As used herein (other than in this paragraph), the term "cytokine" includes biologically active fragments of cytokines and functionally equivalent molecules of cytokines.

The at least one portion of the sample of lymphocytes may be incubated in a medium. Suitably, the medium is cell culture medium. Lymphocytes incubated in the absence of cytokines capable of stimulating activation of $CD4^+,CD25^+$ T cells or of prolonging survival or supporting proliferation of activated $CD4^+,CD25^+$ T cells will typically be incubated in medium that does not contain cytokines, or contains cytokines in such low amounts that they do not stimulate activation of $CD4^+,CD25^+$ T cells or prolong survival or support proliferation of activated $CD4^+,CD25^+$ T cells. Cytokine free medium is known in the art and is that with no foreign serum, conditioned media or specific cytokines has been added. The at least one portion of the sample of lymphocytes incubated in the presence of at least one cytokine selected from the group consisting of IL-5, IL-12, IL-23 and IFN-γ, or a biologically active fragment thereof, or a functionally equivalent molecule thereof, may be incubated in the same media as mentioned above, to which has been added the at least one cytokine selected from the group consisting of IL-5, IL-12, IL-23 and IFN-γ, or a biologically active fragment thereof, or a functionally equivalent molecule thereof.

Activated $CD4^+,CD25^+$ T cells are typically capable of conferring tolerance in a subject to the antigen to which the $CD4^+,CD25^+$ T cells have been activated. Thus, it would be expected that the peripheral blood of a subject that was tolerant to a specific antigen would comprise $CD4^+,CD25^+$ T cells activated to the specific antigen that are capable of conferring tolerance to that specific antigen. However, as discussed above, the inventors have found that $CD4^+,CD25^+$ T cells activated to a specific antigen are short lived in the absence of specific cytokines and the activated $CD4^+,CD25^+$ T cells are generally not viable or have reduced viability after a period of between 24 hours and 1 week following contact with the specific antigen, unless the activated $CD4^+,CD25^+$ T cells are incubated in the presence of at least one cytokine selected from the group consisting of IL-5, IL-12, IL-23 and IFN-γ, or a biologically active fragment thereof, or a functionally equivalent molecule thereof.

The inventors have developed methods whereby a sample of lymphocytes may be incubated so as to promote a distinction between $CD4^+,CD25^+$ T cells that have been activated to a specific antigen from those that have not been activated to the specific antigen. For example, the inventors have observed that $CD4^+,CD25^+$ T cells activated to a specific antigen are not capable of proliferation, and typically die, when contacted with specific antigen in media which does not contain cytokines capable of prolonging survival or supporting proliferation of activated $CD4^+,CD25^+$ T cells. Accordingly, $CD4^+,CD25^+$ T cells activated to the specific antigen will not proliferate in the absence of cytokines which are capable of stimulating activation of $CD4^+,CD25^+$ T cells or of prolonging survival or supporting proliferation of activated $CD4^+$, $CD25^+$ T cells, such as IL-5, IL-12, IL-23 and IFN-γ, or a biologically active fragment thereof, or a functionally equivalent molecules thereof, and tolerance to a specific antigen can therefore be determined by low or no proliferation of $CD4^+$, $CD25^+$ T cells when the lymphocytes are contacted with a specific antigen in the absence of cytokines capable of stimulating activation of activated $CD4^+,CD25^+$ T cells or of prolonging survival or supporting proliferation of $CD4^+,CD25^+$ T cells. The presence of $CD4^+,CD25^+$ T cells activated to the specific antigen may be detected by, for example, measuring the proliferation of $CD4^+,CD25^+$ T cells in the absence of cytokines which are capable of stimulating activation of $CD4^+,CD25^+$ T cells or prolonging survival or supporting proliferation of activated $CD4^+,CD25^+$ T cells, relative to that of $CD4^+,CD25^+$ T cells in the presence of at least one cytokine selected from the group consisting of IL-5, IL-12, IL-23 and IFN-γ, or a biologically active fragment thereof, or a functionally equivalent molecule thereof. Thus, in one embodiment, tolerance to a specific antigen in a subject may be determined by:

(a) obtaining from the subject a sample comprising $CD4^+$, $CD25^+$ T cells;

(b) contacting the $CD4^+,CD25^+$ T cells with the specific antigen;

(c) incubating a first portion of the $CD4^+,CD25^+$ T cells in the absence of cytokines capable of stimulating activation of $CD4^+,CD25^+$ T cells or of prolonging survival or supporting proliferation of activated $CD4^+,CD25^+$ T cells, and a second portion of the $CD4^+,CD25^+$ T cells in the presence of at least one cytokine selected from the group consisting of IL-5, IL-12, IL-23 and IFN-γ, or a biologically active fragment thereof, or a functionally equivalent molecule thereof;

(d) thereafter detecting whether the $CD4^+,CD25^+$ T cells from each portion have proliferated whereby tolerance to the specific antigen, is indicated by increased proliferation of the $CD4^+,CD25^+$ T cells of the second portion relative to the $CD4^+,CD25^+$ T cells of the first portion.

Lack of tolerance of the subject for the specific antigen is indicated by a decrease in proliferation, or no change in proliferation, of the $CD4^+,CD25^+$ T cells of the second portion relative to the first portion.

In one form, $CD4^+$ T cells may be used in combination with an antibody which removes or inactivates $CD4^+,CD25^-$ T cells such as, for example, anti-CD45RB RO. Thus, in another embodiment, tolerance to a specific antigen in a subject may be determined by:

(a) obtaining from the subject a sample comprising $CD4^+$ T cells;

(b) contacting the $CD4^+$ T cells with the specific antigen;

(c) incubating the $CD4^+$ T cells in the presence of an antibody which inactivates $CD4^+,CD25^-$ T cells;

(d) incubating a first portion of the $CD4^+$ T cells in the absence of cytokines capable of stimulating activation of $CD4^+,CD25^+$ T cells or of prolonging survival or of supporting proliferation of $CD4^+CD25^+$ T cells, and a second portion of the $CD4^+$ T cells in the presence of at least one cytokine selected from the group consisting of IL-5, IL-12, IL-23 and IFN-γ, or a biologically active fragment thereof, or a functionally equivalent molecule thereof;

(e) thereafter detecting whether $CD4^+,CD25^+$ T cells from each portion have proliferated whereby tolerance to the specific antigen is indicated by proliferation of the $CD4^+$, $CD25^+$ T cells of the second portion relative to the T cells of the first portion.

Lack of tolerance of the subject for the specific antigen is indicated by a decrease, or no change, in proliferation of the $CD4^+,CD25^+$ T cells of the second portion relative to the first portion.

Typically the antibody which inactivates $CD4^+,CD25^-$ T cells is an anti-CD45 RB/RO antibody, such as that described in WO02/072832.

As $CD4^+,CD25^+$ T cells activated to a specific antigen will not proliferate unless they are incubated in the presence of the specific antigen and cytokines which support proliferation of activated $CD4^+,CD25^+$ T cells, in samples obtained from a subject which has $CD4^+,CD25^+$ T cells activated to the specific antigen, the first portion will not proliferate, while the second portion, which is incubated in the presence of at least one cytokine selected from the group consisting of IL-5, IL-12, IL-23 and IFN-γ, or a biologically active fragment thereof, or a functionally equivalent molecule thereof, will proliferate.

Optionally, the lymphocytes are incubated in the presence of anti-IL-2 and/or anti-IL-4 antibody to inactivate any IL-2 or IL-4.

Alternatively, proliferation of $CD4^+,CD25^+$ T cells may be determined in $CD4^+$ T cell populations by measuring the proliferation of $CD4^+,CD25^-$ T cells. As $CD4^+,CD25^+$ T cells activated to a specific antigen are not capable of growth or survival in the presence of the specific antigen and in the absence of cytokines which are capable of stimulating activation of $CD4^+,CD25^+$ T cells or of prolonging survival or supporting proliferation of activated $CD4^+,CD25^+$ T cells, they are therefore not capable of inhibiting activation and proliferation of the $CD4^+,CD25^-$ population in response to the specific antigen in the absence of cytokines which are capable of stimulating activation of $CD4^+,CD25^+$ T cells or of prolonging survival or stimulating proliferation of activated $CD4^+,CD25^+$ T cells. However, a portion of $CD4^+,CD25^+$ T cells will proliferate in response to third party antigen, and will therefore suppress $CD4^+,CD25^-$ T cells in response to the third party antigen. Accordingly, tolerance may be determined in a sample of $CD4^+$ lymphocytes from a subject by comparing proliferation of unfractionated $CD4^+$ T cells to that of $CD4^+,CD25^-$ T cells. In the absence of cytokines capable of stimulating activation of $CD4^+,CD25^+$ T cells, proliferation of $CD4^+,CD25^-$ T cells in response to third party antigen will increase relative to that of the mixed population in $CD4^+$ T cells from a subject tolerant to a specific antigen. In contrast, in the absence of cytokines capable of stimulating activation or prolonging survival or supporting proliferation of $CD4^+,CD25^+$ T cells, proliferation of isolated $CD4^+,CD25^-$ T cells in response to specific antigen will not increase relative to that of the mixed population in $CD4^+$ T cells from a subject tolerant to a specific antigen. Thus, in another embodiment, the method comprises the steps of:

(a) obtaining from the subject a sample of lymphocytes comprising $CD4^+$ T cells;
(b) preparing from the sample a $CD4^+$ T cell population and a $CD4^+,CD25^-$ T cell population;
(c) contacting a first portion of the $CD4^+$ T cell population with the specific antigen, and a first portion of the $CD4^+,CD25^-$ T cell population with the specific antigen, and contacting a second portion of the $CD4^+$ T cell population with a further antigen, and contacting a second portion of the $CD4^+,CD25^-$ T cell population with a further antigen;
(d) incubating the first and second portions in the absence of cytokines that are capable of stimulating activation of $CD4^+,CD25^+$ T cells or of prolonging survival or stimulating proliferation of activated $CD4^+CD25^+$ T cells; and
(e) thereafter comparing proliferation of the portions of the $CD4^+$ T cell population and the $CD4^+,CD25^-$ T cell population in the first and second portions, whereby low or no increase in proliferation of the $CD4^+,CD25^-$ T cell population relative to that of the $CD4^+$ T cell population in the first portions, and increased proliferation of the $CD4^+,CD25^-$ T cell population relative to the $CD4^+$ T cell population in the second portions, is indicative of tolerance to the specific antigen in the subject.

Typically, the $CD4^+,CD25^-$ T cell population is prepared by depleting $CD4^+,CD25^+$ T cells from a portion of the sample of lymphocyte comprising $CD4^+$ T cells.

In this embodiment, $CD4^+,CD25^+$ T cells activated to the specific antigen in the first portion from a subject tolerant to the specific antigen will not proliferate in response to the specific antigen and will not be able to suppress proliferation of $CD4^+,CD25^-$ T cell population in the unfractionated $CD4^+$ T cells. Thus, proliferation of the $CD4^+$ T cells will be similar to proliferation of the first portion of $CD4^+,CD25^-$ T cells following contacting the T cells with specific antigen. However, $CD4^+,CD25^+$ T cells in the $CD4^+$ population of the second portion will proliferate following contact with a further antigen and will therefore be capable of inhibiting proliferation of $CD4^+,CD25^-$ lymphocytes in unfractionated $CD4^+$ T cells. When the $CD4^+,CD25^+$ T cells are removed from the $CD4^+$ T cell population, the resulting $CD4^+,CD25^-$ T cells are enriched, and these enriched cells of the second portion exhibit greater proliferation following contact with the further antigen.

If the subject does not comprise $CD4^+,CD25^+$ T cells activated to the specific antigen, then the level of proliferation in response to the specific antigen in the first portion will be similar to proliferation following contact with the further antigen in the second portion, that is the response of the $CD4^+,CD25^-$ T cell population will be greater than that of unfractionated $CD4^+$ T cells in the first portion.

It is also possible to determine tolerance by detecting proliferation of $CD4^+,CD25^+$ T cells activated to the specific antigen in the presence of IL-5, IL-12, IL-23 or IFN-$\gamma$, or a biologically active fragment thereof, or a functionally equivalent molecule thereof, and in the absence of cytokines which are capable of stimulating activation of $CD4^+,CD25^+$ T cells, because naïve $CD4^+,CD25^+$ T cells are not capable of proliferation in the presence of any one or more of IL-5, IL-12, IL-23 or IFN-$\gamma$, or a biologically active fragment thereof, or a functionally equivalent molecule thereof, and in the absence of cytokines which are capable of stimulating activation of $CD4^+,CD25^+$ T cells. Thus, in the presence of IL-5, IL-12, IL-23 or IFN-$\gamma$, or a biologically active fragment thereof, or a functionally equivalent molecule thereof, and in the absence of cytokines which are capable of stimulating activation of $CD4^+,CD25^+$ T cells, only activated $CD4^+,CD25^+$ T cells will proliferate.

Proliferation of $CD4^+,CD25^+$ T cells activated to a specific antigen will inhibit proliferation of $CD4^+,CD25^-$ T cells in response to the specific antigen. Thus, proliferation of $CD4^+,CD25^+$ T cells activated to the specific antigen in the presence of IL-5, IL-12, IL-23 and/or IFN-$\gamma$, or biologically active fragments thereof, or functionally equivalent molecules thereof, may be detected by measuring the proliferation of unfractionated $CD4^+$ T cells in the presence of at least one cytokine selected from the group consisting of IL-5, IL-12, IL-23 and IFN-$\gamma$, or a biologically active fragment thereof, or a functionally equivalent molecule thereof, and in the absence of cytokines which are capable of stimulating activation of $CD4^+,CD25^+$ T cells. Accordingly, in another embodiment, the method comprises the steps of:

(a) obtaining from the subject a sample comprising unfractionated lymphocytes, the sample comprising $CD4^+$ T cells;
(b) contacting the unfractionated lymphocytes with the specific antigen;
(c) incubating a first portion of the unfractionated lymphocytes in the absence of cytokines which are capable of stimulating activation of $CD4^+,CD25^+$ T cells or of prolonging survival or supporting proliferation of activated $CD4^+,CD25^+$ T cells, and a second portion of the unfractionated lymphocytes in the presence of at least one cytokine selected from the group consisting of IL-5, IL-12, IL-23 and IFN-$\gamma$, or a biologically active fragment thereof, or a functionally equivalent molecule thereof;
(d) thereafter detecting proliferation of unfractionated lymphocytes in the first portion relative to the second portion, whereby reduced proliferation of $CD4^+$ T cells in the second portion relative to the first portion indicates that the subject is tolerant to the specific antigen.

In unfractionated lymphocytes populations, proliferation of $CD4^+,CD25^+$ T cells activated to the specific antigen in the presence of at least one cytokine selected from the group consisting of IL-5, IL-12, IL-23 and IFN-$\gamma$, or a biologically active fragment thereof, or a functionally equivalent molecule thereof, results in inhibition of proliferation of $CD4^+,CD25^-$ T cells in response to the specific antigen. The proliferation of CD4+,CD25− T cells is usually an order of magnitude greater than that of the minority CD4+,CD25+ T cells, thus the inhibition of the CD4+,CD25− population is not exceeded by the increased proliferation of the minor CD4+,CD25+ T cell population. The net effect in a sample from a tolerant subject is inhibition of proliferation of the unfractionated CD4+ T cells incubated in the presence of at least one cytokine selected from the group consisting of IL-5, IL-12, IL-23 and IFN-γ, or a biologically active fragment thereof, or a functionally equivalent molecule thereof, relative to proliferation of unfractionated CD4+ T cells incubated in the absence of cytokines capable of stimulating activation of CD4+,CD25+ T cells or of prolonging survival or supporting proliferation of activated CD4+,CD25+ T cells. The lack of proliferation of CD4+,CD25+ T cells in the absence of cytokines capable of stimulating activation of CD4+,CD25+ T cells or of prolonging survival or supporting proliferation of activated CD4+, CD25+ T cells, results in proliferation of CD4+,CD25− T cells (in the CD4+ population) in response to the specific antigen as this response is uninhibited by CD4+,CD25+ T cells activated to the specific antigen which die without the specified cytokines.

The inventors have further found that while CD4+,CD25+ T cells activated to a specific antigen are not capable of proliferation in the absence of cytokines capable of stimulating activation of CD4+,CD25+ T cells, or of prolonging survival or supporting proliferation of activated CD4+,CD24+ T cells, following contact with the specific antigen, the activated CD4+,CD25+ T cells will proliferate in response to contact with a further antigen in the absence of cytokines capable of stimulating activation of CD4+,CD25+ T cells, or of prolonging survival or supporting proliferation of activated CD4+,CD25+ T cells. Accordingly, in another embodiment, the method comprises the steps of:

(a) obtaining from the subject a sample comprising CD4+, CD25+ T cells;
(b) contacting a first portion of the CD4+,CD25+ T cells with the specific antigen, and a second portion of the CD4+, CD25+ T cells with a further antigen;
(c) incubating the first and second portions in the absence of cytokines which are capable of stimulating activation of CD4+,CD25+ T cells or prolonging survival or supporting proliferation of activated CD4+,CD25+ T cells;
(d) thereafter detecting the proliferation of the CD4+,CD25+ T cells in the first and second portion, whereby greater proliferation of CD4+,CD25+ T cells in the second portion relative to CD4+,CD25+ T cells in the first portion indicates that the subject is tolerant to the specific antigen.

It will be understood by those skilled in the art that the further antigen is different to that of the specific antigen. For example, where the specific antigen may be a donor antigen, the further antigen may be a third party antigen.

The inventors have further found that proliferation of CD4+,CD25− T cells from animals tolerant to a specific antigen is not fully suppressed by CD4+,CD25+ T cells from tolerant animals when admixed at a ratio of CD4+,CD25+ T cells:CD4+,CD25− T cells of greater than about 1:3, typically about 1:1, when incubated in the absence of cytokines capable of stimulating activation of CD4+,CD25+ T cells, or of prolonging survival or supporting proliferation of CD4+, CD25+ T cells activated to the specific antigen. This contrasts with the ability of naïve CD4+,CD25+ T cells to fully inhibit the responses of naïve CD4+,CD25− T cells when present in a ratio of at least 1:3, typically 1:1. As IL-5, IL-12, IL-23 or IFN-γ can prolong survival and support proliferation of CD4+,CD25+ T cells activated to a specific antigen, incubation of CD4+,CD25+ T cells with CD4+,CD25− T cells from a subject tolerant to a specific antigen in the presence of specific antigen and one or more of IL-5, IL-12, IL-23 or IFN-γ, a biologically active fragment thereof, or a functionally equivalent molecule thereof, would result in inhibition of proliferation of the CD4+,CD25− T cells.

Accordingly, in another embodiment, the method comprises the steps of:

(a) obtaining from the subject a sample comprising CD4+, CD25+ T cells and CD4+,CD25 T cells;
(b) preparing from the sample an admixed T cell population comprising CD4+,CD25+ T cells and CD4+,CD25− T cells in a ratio of greater than about 1:3 (CD4+,CD25+ T cells:CD4+,CD25− T cells), typically about 1:1;
(c) contacting a first portion of the admixed T cell population with the specific antigen, and a second portion of the admixed T cell population with a further antigen;
(d) incubating the first and second portions in the absence of cytokines which are capable of stimulating activation of CD4+,CD25+ T cells or of prolonging survival or supporting proliferation of activated CD4+,CD25+ T cells;
(e) thereafter determining proliferation of the first portion relative to the second portion whereby greater proliferation in the first portion relative to the second portion indicates that the subject is tolerant to the specific antigen.

Typically, a CD4+,CD25− T cell population is prepared by depleting CD4+,CD25+ T cells from a portion of the sample, and a CD4+,CD25+ T cell population is prepared by depleting CD4+,CD25− T cells from a portion of the sample, and the admixed T cell population prepared by mixing the CD4+, CD25+ T cell population and the CO4+,CD25− T cell population to obtain the ratio of CD4+,CD25+ T cells:CD4+, CD25− T cells of greater than 1:3.

As the first and second portions are incubated in the absence of cytokines capable of stimulating activation of CD4+,CD25+ T cells or of prolonging survival or supporting proliferation of CD4+,CD25+ T cells activated to the specific antigen, then CD4+,CD25+ T cells activated to the specific antigen will not survive or proliferate in response to the specific antigen and will therefore not be able to inhibit proliferation of the CD4+,CD25− T cells. In contrast, naïve CD4+, CD25+ T cells will be able to inhibit proliferation of CD4+, CD25− T cells in the second portion.

In another embodiment, the method comprises the steps of:
(a) obtaining from the subject a sample comprising CD4+, CD25+ T cells and CD4+,CD25− T cells;
(b) preparing from the sample a CD4+CD25− T cell population, and an admixed T cell population comprising CD4+, CD25+ T cells and CD4+,CD25− T cells in a ratio of greater than 1:3;
(c) contacting the CD4+,CD25− T cell population and the admixed T cell population with the specific antigen;
(d) incubating the CD4+,CD25− T cell population and the admixed T cell population in the absence of cytokines which are capable of stimulating activation of CD4+, CD25+ T cells or of prolonging survival or supporting proliferation of activated CD4+,CD25+ T cells;
(e) thereafter determining proliferation of the CD4+,CD25− T cell population and the admixed T cell population whereby proliferation of the admixed T cell population substantially the same as that of the CD4+,CD25− T cell population indicates that the subject is tolerant to the specific antigen.

Typically, a CD4+,CD25− T cell population is prepared by depleting CD4+,CD25+ T cells from a portion of the sample, and a CD4+,CD25+ T cell population is prepared by depleting CD4+,CD25− T cells from a portion of the sample, and the admixed T cell population prepared by mixing the CD4+, CD25+ T cell population and the CD4+,CD25− T cell population to obtain the ratio of CD4+,CD25+ T cells:CD4+, CD25− T cells of greater than 1:3.

In this embodiment, in the absence of cytokines capable of stimulating activation of CD4+,CD25+ T cells or of prolonging survival or supporting proliferation of activated CD4+, CD25+ T cells, activated CD4+,CD25+ T cells in the admixed T cell population would not survive and would therefore not be able to suppress proliferation of the CD4+,CD25− T cells. The effect would be that proliferation of the CD4+,CD25− T cells in the admixed T cell population would be approximately the same as that of the CD4+,CD25− T cell population.

In another embodiment, the method comprises the steps of:
(a) obtaining from the subject a sample comprising CD4+, CD25+ T cells and CD4+,CD25− T cells;
(b) preparing from the sample an admixed T cell population by mixing the CD4+,CD25+ T cells and the CD4+,CD25− T cells in a ratio greater than 1:3, typically 1:1;
(c) contacting the admixed T cell population with the specific antigen;
(d) incubating a first portion of the admixed T cell population in the absence of cytokines capable of stimulating activation of CD4+,CD25+ T cells or of prolonging survival or supporting proliferation of activated CD4+CD25+ T cells, and a second portion of the admixed T cell population in the presence of at least one cytokine selected from the group consisting of IL-5, IL-12, IL-23 and IFN-γ, or a biologically active fragment thereof, or a functionally equivalent molecule thereof;
(e) thereafter determining proliferation of T cells in the first and second portions whereby greater proliferation of T cells in the first portion relative to the second portion indicates tolerance to the specific antigen.

Typically, a CD4+,CD25− T cell population is prepared by depleting CD4+,CD25+ T cells from a portion of the sample, and a CD4+,CD25+ T cell population is prepared by depleting CD4+,CD25− T cells from a portion of the sample, and the admixed T cell population prepared by mixing the CD4+, CD25+ T cell population and the CD4+,CD25− T cell population to obtain the ratio of CD4+,CD25+ T cells:CD4+, CD25− T cells of greater than 1:3.

In this embodiment, CD4+,CD25+ T cells activated to the specific antigen survive and proliferate in the presence of the at least one cytokine selected from the group consisting of IL-5, IL-12, IL-23 and IFN-γ, or a biologically active fragment thereof, or a functionally equivalent molecule thereof, and as a consequence, inhibit proliferation of the CD4+, CD25− T cells. In contrast, in the absence of cytokines capable of stimulating activation of CD4+,CD25+ T cells or of prolonging survival or supporting proliferation of activated CD4+,CD25+ T cells, CD4+,CD25+ T cells activated to the specific antigen do not proliferate or survive and therefore do not inhibit CD4+,CD25− T cells. As a consequence, in the presence of CD4+,CD25+ T cells activated to the specific antigen, proliferation of T cells is greater in the first portion.

In embodiments where the at least one portion of the sample of lymphocytes is incubated in the presence of at least one cytokine selected from the group consisting of IL-5, IL-12, IL-23 and IFN-γ, or a biologically active fragment thereof, or a functionally equivalent molecule thereof, the at least one sample of lymphocytes may, in some embodiments, be incubated in the presence of:
(a) at least one cytokine selected from the group consisting of IL-5, IL-12 and IFN-γ, or a biologically active fragment thereof, or a functionally equivalent molecule thereof; or
(b) IL-5, a biologically active fragment thereof, or a functionally equivalent molecule thereof; or
(c) IL-12, a biologically active fragment thereof, or functionally equivalent molecule thereof; or
(d) IFN-γ, a biologically active fragment thereof, or a functionally equivalent molecule thereof; or
(e) IL-23, a biologically active fragment thereof, or a functionally equivalent molecule thereof.

The period of time in which the at least one portion of the sample of lymphocytes is incubated to promote distinction of CD4+,CD25+ T cells that have been activated to a specific antigen from CD4+,CD25+ T cells that have not been activated to the specific antigen may include: 24 hours to 10 days; 24 hours to 9 days; 24 hours to 8 days; 24 hours to 7 days; 24 hours to 6 days; 24 hours to 5 days; 24 hours to 4 days; 24 hours to 3 days. As used herein, the term "proliferation" refers to division of cells or cell growth. Proliferation of CD4+, CD25+ T cells and CD4+,CD25− T cells may be determined by any methods known in the art for measuring proliferation of lymphocyte populations. Examples of suitable methods are described in, for example, Transplantation (1999) 67:605-613.

The specific antigen may be any antigen. For example, in the case of testing for the development of tolerance to a transplant, the specific antigen will typically be a donor antigen. The donor antigen may be alloantigen or xenoantigen. In the case of testing for development of tolerance during autoimmune disease, the specific antigen will typically be the autoantigen. In the case of testing for tolerance to an infectious agent, the specific antigen will typically be the infectious agent or an antigen derived from that infectious agent. In the case of testing for tolerance to a tumour, the specific agent will typically be tumour antigen or tissue.

It will be appreciated by persons skilled in the art that the method may be applied over a time period to determine whether tolerance to a specific antigen is changing over time in the subject.

The inventors have further developed methods whereby CD4+,CD25+ T cells activated to a specific antigen, and therefore are capable of inducing tolerance to a specific antigen in a subject, can be cultured in vitro. This is made possible by the finding by the inventors that CD4+,CD25+ T cells activated to the specific antigen can proliferate in the presence of at least one cytokine selected from the group consisting of IL-5, IL-12, IL-23 and IFN-γ, or a biologically active fragment thereof, or a functionally equivalent molecule thereof. Thus, the present invention further provides a method of growing CD4+,CD25+ T cells activated to a specific antigen in vitro by culturing the activated CD4+,CD25+ T cells in the presence of at least one cytokine selected from the group consisting of IL-5, IL-12, IL-23 and IFN-γ, or a biologically active fragment thereof, or a functionally equivalent molecule thereof. The activated CD4+,CD25+ T cells are typically contacted with a specific antigen in vitro prior to, or simultaneously with, culturing the activated CD4+,CD25+ T cells in the presence of the at least one cytokine selected from the group consisting of IL-5, IL-12, IL-23 and IFN-γ, or a biologically active fragment thereof, or a functionally equivalent molecule thereof. The activated CD4+,CD25+ T cells may be cultured in the presence of the specific antigen.

In some embodiments, the CD4+,CD25+ T cells activated to the specific antigen may be cultured in the presence of the at least one cytokine selected from the group consisting of IL-5, IL-12, IL-23 and IFN-γ, or a biologically active fragment thereof, or a functionally equivalent molecule thereof, for a period of time longer than the time in which activated CD4+,CD25+ T cells remain viable in vitro following activation when cultured in the absence of at least one cytokine selected from the group consisting of IL-5, IL-12, IL-23 and IFN-γ, or a biologically active fragment thereof, or a functionally equivalent molecule thereof.

The CD4+,CD25+ T cells activated to a specific antigen grown in vitro may be administered to a subject in need thereof to increase the subject's tolerance to the specific antigen. The CD4+,CD25+ T cells activated to the specific antigen grown in vitro may be used to suppress that portion of the immune system that recognises the specific antigen, but not other antigens. As the tolerance is increased to a specific antigen (rather than to antigens in general), that portion of the immune system that does not recognise the specific antigen is largely unaffected. For example, tolerance may be induced to a specific transplanted tissue, while at the same time the subject is capable of eliciting an effective immune response to other antigens such as infectious agents or transplanted tissue from an unrelated donor, etc. In other words, although the subject is tolerant to the specific antigens of the transplanted tissue, the subject is otherwise not immunosuppressed. In contrast, known methods of ameliorating or reducing transplant rejection in a subject involve immunosuppression of the subject's immune system to all antigens, which renders the subject susceptible to infection from, for example, pathogens and opportunistic organisms, and to cancer.

Thus, the invention further provides a method for increasing tolerance to a specific antigen in a subject which comprises administering to the subject an effective amount of CD4+,CD25+ T cells activated to the specific antigen wherein the activated CD4+,CD25+ T cells have been grown in vitro by culturing activated CD4+,CD25+ T cells in the presence of at least one cytokine selected from the group consisting of IL-5, IL-12, IL-23 and IFN-γ, or a biologically active fragment thereof, or a functionally equivalent molecule thereof. As used herein, the expression "increasing tolerance to a specific antigen" means an increase in tolerance to a specific antigen relative to the tolerance to the specific antigen prior to application of the method of the invention.

The CD4+,CD25+ T cells activated to the specific antigen are typically grown in vitro by:
(a) contacting CD4+,CD25+ T cells activated to the specific antigen with the specific antigen in vitro;
(b) culturing the activated CD4+,CD25+ T cells in the presence of at least one cytokine selected from the group consisting of IL-5, IL-12, IL-23 and IFN-γ, or a biologically active fragment thereof, or a functionally equivalent molecule thereof.

The activated CD4+,CD25+ T cells may in some embodiments be cultured in the presence of:
(a) at least one cytokine selected from the group consisting of IL-5, IL-12 and IFN-γ, or a biologically active fragment thereof, or a functionally equivalent molecule thereof; or
(b) IL-5, a biologically active fragment thereof, or a functionally equivalent molecules thereof; or
(c) IL-12, a biologically active fragment thereof, or a functionally equivalent molecules thereof; or
(d) IFN-γ, a biologically active fragment thereof, or a functionally equivalent molecules thereof; or
(e) IL-23 a biologically active fragment thereof, or a functionally equivalent molecules thereof.

The CD4+,CD25+ T cells activated to the specific antigen may be activated in vitro or in vivo. In some embodiments, CD4+,CD25+ T cells are isolated as naïve T cells and thereafter activated in vitro. The term "naïve CD4+,CD25+ T cell" refers to a CD4+,CD25+ T cell which has not been contacted by an antigen in the presence of IL-2 and/or IL-4, and is therefore not activated. Naïve CD4+,CD25+ T cells may be isolated from thymus, bone marrow, peripheral lymphoid tissue or blood. Typically, the naïve CD4+,CD25+ T cells are isolated from the subject. Naïve CD4+,CD25+ T cells may be activated in vitro by contacting naïve T cells with an antigen and culturing the T cells in the presence of one or more of the cytokines selected from the group consisting of IL-2 and IL-4, or a biologically active fragment thereof, of a functionally equivalent molecule thereof.

Thus, in one embodiment, the method of growing CD4+, CD25+ T cells activated to the specific antigen in vitro may comprise the following steps:
(a) contacting naïve CD4+,CD25+ T cells with a specific antigen and culturing the lymphocytes in the presence of IL-2, a biologically active fragment thereof, or a functionally equivalent molecule thereof, and/or IL-4, a biologically active fragment thereof, or a functionally equivalent molecule thereof, to thereby activate the CD4+,CD25+ T cells; and
(b) culturing the activated CD4+,CD25+ T cells in the presence of at least one cytokine selected from the group consisting of IL-5, IL-12, IL-23 and IFN-γ, or a biologically active fragment thereof, or a functionally equivalent molecules thereof.

Steps (a) and (b) above may be performed simultaneously, or step (a) may be performed prior to step (b).

Antigen presenting cells with the specific antigen presented on the cell surface are typically co-cultured with the naïve CD4+,CD25+ T cells at 37° C. in the presence of IL-2 and/or IL-4, biologically active fragments thereof, or functionally equivalent molecules thereof, for a sufficient length of time to permit proliferation of CD4+,CD25+ T cells activated to the specific antigen.

In another embodiment, the CD4+,CD25+ T cells are activated in vivo and thereafter isolated for use in the method of the invention. In this instance, the CD4+,CD25+ T cells that are activated in vivo are isolated from peripheral blood lymphocytes. Typically, the activated CD4+,CD25+ T cells are isolated from the subject.

Without wishing to be bound by theory, the inventors believe that in the case of CD4+,CD25+ T cells that are activated in vivo, following contact with the antigen in vivo, activation of the resident naïve CD4+,CD25+ T cells is thereafter supported by the presence of IL-2, a biologically active fragment thereof, or a functionally equivalent molecule thereof, and/or IL-4, a biologically active fragment thereof, or a functionally equivalent molecule thereof, in vivo. However, subsequent to this activation the activated CD4+,CD25+ T cells are less responsive to further contact with the antigen in the presence of IL-2, a biologically active fragment thereof, or a functionally equivalent molecule thereof, and/or IL-4, a biologically active fragment thereof, or a functionally equivalent molecule thereof.

In another embodiment, CD4+,CD25+ T cells activated to the specific antigen may be grown by:
(a) contacting a mixture of activated and naïve CD4+, CD25+ T cells with the specific antigen in vitro;
(b) culturing the CD4+,CD25+ T cells in the presence of IL-2, a biologically active fragment thereof, or a functionally equivalent molecule thereof, and/or IL-4, a biologically active fragment thereof, or a functionally equivalent molecule thereof, and at least one cytokine selected from the group consisting of IL-5, IL-12, IL-23 and IFN-γ, or a biologically active fragment thereof, or a functionally equivalent molecule thereof.

In this embodiment, the presence of IL-2 and/or IL-4, biologically active fragments thereof, or functionally equivalent molecules thereof, permits activation of naïve CD4+, CD25+ T cells, while the presence of the at least one cytokine selected from the group consisting of IL-5, IL-12, IL-23 and IFN-γ, or a biologically active fragment thereof, or a functionally equivalent molecule thereof, permits proliferation of the CD4$^+$,CD25$^+$ T cells activated to the specific antigen.

In some embodiments, the mixture of activated and naïve CD4$^+$,CD25$^+$ T cells is contacted with the specific antigen in vitro and cultured in the presence of IL-4, a biologically active fragment thereof, or a functionally equivalent molecule thereof, IL-13, a biologically active fragment thereof, or a functionally equivalent molecule thereof, and IL-S, a biologically active fragment thereof, or a functionally equivalent molecule thereof.

It is envisaged that it may not be immediately apparent whether CD4$^+$,CD25$^+$ T cells from a subject are naïve or have been activated to the specific antigen in vivo. Typically, a T cell may be determined to be naïve or activated in vivo by contacting the T cell with the specific antigen, and determining proliferation of the T cell in the presence of one or more cytokines selected from the group consisting of IL-5, IL-12, IL-23 and/or IFN-γ, or a biologically active fragment thereof, or a functionally equivalent molecule thereof. Under such conditions, naïve T cells will not undergo a proliferation while CD4$^+$,CD25$^+$ T cells activated to the specific antigen will exhibit proliferation.

Once the CD4$^+$,CD25$^+$ T cells are activated, whether it be in vitro or in vivo, the CD4$^+$,CD25$^+$ T cells activated to the specific antigen are then contacted with the specific antigen in a similar manner to that described above. That is, the CD4$^+$,CD25$^+$ T cells activated to the specific antigen are contacted with the specific antigen by presenting the antigen to the T cell on the surface of an antigen presenting cell. Typically, the antigen is presented to the T cell associated with a major histocompatibility (MHC) molecule (typically class II) on the surface of an antigen presenting cell.

Subsequent to, or simultaneously with, contacting the specific antigen, the CD4$^+$,CD25$^+$ T cells are cultured in the presence of one or more cytokines selected from the group consisting of IL-5, IL-12, IL-23 and IFN-γ, or a biologically active fragment thereof, or a functionally equivalent molecule thereof. As discussed above, activated CD4$^+$,CD25$^+$ T cells are short-lived and normally do not remain viable for more than 3 days. By culturing the activated CD4$^+$,CD25$^+$ T cells in the presence of at least one cytokine selected from the group consisting of IL-5, IL-12, IL-23 and IFN-γ, or a biologically active fragments thereof, or a functionally equivalent molecules thereof, the CD4$^+$,CD25$^+$ T cells activated to the specific antigen can undergo proliferation following or during contact with the specific antigen. The step of culturing may be accomplished by simply incubating the T cells in media containing the cytokines selected from the group consisting of IL-5, IL-12, IL-23 and IFN-γ, or a biologically active fragment thereof, or a functionally equivalent molecule thereof, and typically, the antigen presenting cell with specific antigen. For example, by culturing in the presence of a cytokine selected from the group consisting of IL-5, IL-12, IL-23 and IFN-γ, or a biologically active fragment thereof, or a functionally equivalent molecule thereof, the T cells are contacted with the cytokine selected from the group consisting of IL-5, IL-12, IL-23 and IFN-γ, or a biologically active fragment thereof, or a functionally equivalent molecule thereof.

As used herein, the term "culturing" refers to the growth and maintenance in a viable state of cells in vitro. The step of culturing CD4$^+$,CD25$^+$ T cells may be accomplished by simply incubating the T cells in a culture medium which provides sufficient carbon, nitrogen, oxygen and other nutrients, growth factors, buffers, co-factors and any other substance as required to at least maintain the viability of the T cells. For example, T cells may be cultured in RPMI or DMEM supplemented with 10% fetal calf-serum (FCS) and other supplements such as antimicrobial agents, growth factors, other cytokines (see, for example, Transplantation (1993) 55:374-379). Examples of suitable medium include medium formulations that are known to those skilled in the art such as, for example, RPMI, IMDM, DMEM, DMEM/F12, EMEM with or without serum or with reduced serum, and further optionally including antibiotics, lipids, transferrin, insulin, additional nutrient supplements such as amino acids and co-factors as required.

Generally, cultured T cells are incubated at 37° C. in a 5% $CO_2$ atmosphere.

The CD4$^+$,CD25$^+$ T cells activated to a specific antigen are cultured in the presence of one or more cytokines selected from the group consisting of IL-5, IL-12, IL-23 and IFN-γ, or a biologically active fragment thereof, or a functionally equivalent molecule thereof. Typically, the cytokine selected from the group consisting of IL-5, IL-12, IL-23 and IFN-γ, or a biologically active fragment thereof, or a functionally equivalent molecule thereof, is an isolated polypeptide that is added exogenously to the media in which the T cells are cultured, either as part of a culturing medium or as a purified polypeptide. Alternatively, the cytokine selected from the group consisting of IL-5, IL-12, IL-23 and IFN-γ, or a biologically active fragment thereof, or a functionally equivalent molecule thereof, may be the product of heterologous gene expression in cells that are co-cultured with the T cells.

As discussed above, contacting the CD4$^+$,CD25$^+$ T cell activated to the specific antigen with the specific antigen and culturing the T cells in the presence of one or more cytokines selected from the group consisting of IL-5, IL-12, IL-23 and IFN-γ, or a biologically active fragment thereof, or a functionally equivalent molecule thereof, results in proliferation of the CD4$^+$,CD25$^+$ T cells activated to the specific antigen.

In another embodiment, the CD4$^+$,CD25$^+$ T cells activated to the specific antigen may be contacted with the specific antigen as a portion of a mixed population of cell lineages or as a portion of a mixed population, and the CD4$^+$,CD25$^+$ T cells isolated using the isolation methods described above.

Upon culturing in the presence of one or more cytokines selected from the group consisting of IL-5, IL-12, IL-23 and IFN-γ, or a biologically active fragment thereof, or a functionally equivalent molecule thereof, and subsequent to proliferation, the T cells may then be administered to the subject.

The T cells are administered to the subject to increase the number of CD4$^+$,CD25$^+$ T cells activated to the specific antigen. The T cells are typically administered by parenteral administration. Preparations for parenteral administration include suspensions in sterile aqueous carriers. Aqueous carriers for suspensions may include saline and buffered media. Parenteral vehicles include any solution which is capable of maintaining the activity and viability of the lymphocytes, and may include, for example, cell culture medium, sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

The T cells can be administered, parenterally by injection or by gradual infusion over time independently or together. Administration may be intravenously, intra-arterial, intraperitoneally, intramuscularly, intracavity, intraarticularly, or transdermally. Typically, administration is intravenously.

The administration may be local administration or regional administration to a site of immune activity.

Typically, the $CD4^+,CD25^+$ T cells activated to the specific antigen are administered to obtain a ratio of $CD4^+,CD25^+$ T cells:$CD4^+,CD25^-$ T cells in the subject of about 1:20. Typically, 1:10.

In another aspect, the invention provides a method for treating or preventing in a subject in need thereof a disease resulting from an immune response to an antigen. For example, the disease may be an autoimmune disease, or host-versus-graft disease resulting from allograft or xenograft rejection, or an allergic reaction.

In one embodiment, the disease is an autoimmune-disease. As used herein, "autoimmune disease" refers to a disease resulting from an immune response to an autoantigen. Autoimmune disease may include, but is not intended to be limited to, these particular types of autoimmune diseases: type 1 insulin dependent diabetes mellitus, inflammatory bowel syndrome including ulcerative colitis and Crohn's disease, thrombotic thrombocytopenic purpura, Sjogren's syndrome, encephalitis, acute encephalomyelitis, Guillain Barre Syndrome, chronic inflammatory demyelination polyneuropathy, idiopathic pulmonary fibrosis/alveolitis, asthma, uveitis, iritis, optic neuritis, rheumatic fever, Reiter's syndrome, psoriasis, psoriasis arthritis, multiple sclerosis, progressive systemic sclerosis, primary biliary cirrhosis, pemphigus, pemphigoid, necrotising vasculitis, myasthenia gravis, polymyositis, sarcoidosis, granulomatosis, vasculitis, pernicious anemia, CNS inflammatory disorder, autoimmune haemolytic anaemia, Hashitomo's thyroiditis, Graves disease, habitual spontaneous abortions, Raynaud's syndrome, dermatomyositis, chronic active hepatitis, celiac disease, autoimmune complications of AIDS, atrophic gastritis, ankylosing spondylitis, Addison's disease, atopic dermatitis, allergic rhinitis and conjunctivitis, asthma, chronic demyelinating neuropathy, glomerulonephritis including membranous nephropathy, focal sclerosing glomerulonephritis and minimal change nephropathy, systemic lupus erythematosis, scleroderma, rheumatoid arthritis, and juvenile arthritis.

Without wishing to be bound by theory, the inventors believe that autoimmune disease may be the result of an imbalance in the ratio of $CD4^+,CD25^+$ T cells to $CD4^+,CD25^-$ T cells. The present invention permits the ratio between these cells to be manipulated by culturing $CD4^+,CD25^+$ T cells capable of inducing immune tolerance in vitro and subsequently introducing these cells into the subject to increase the ratio of $CD4^+,CD25^+$ T cells to $CD4^+,CD25^-$ T cells.

The ratio of $CD4^+,CD25^+$ T cells to $CD4^+,CD25^-$ T cells may be further increased by administering to the subject an effective amount of at least one cytokine selected from the group consisting of IL-5, IL-12, IL-23 and IFN-$\gamma$, or a biologically active fragment thereof, or a functionally equivalent molecule thereof.

In another embodiment, the disease is a host-versus-graft disease resulting from allograft rejection. The term "allograft rejection" will be understood by those skilled in the art as referring to an immune response to an antigen(s) of a graft or transplanted tissue in a subject wherein the graft or tissue is obtained from a different member of the same species as the subject.

Allograft rejection includes rejection of all types of allograft and may include for example, allografts of cornea, heart, valves, lung, kidney, liver, pancreas, pancreatic islets, brain, bone, intestine, skin, bone marrow, stem cells, hematopoietic cell or other cells.

In yet another embodiment, the disease is a graft-versus-host disease resulting from bone marrow transplantation or other transplants or lympho-haemopoietic cells such as small bowel transplants.

In yet another embodiment, the disease is a host versus graft response to a xenograft. The term "xenograft rejection" will be understood by those skilled in the art as referring to an immune response to an antigen(s) of a graft or tissue transplant in a subject wherein the tissue is obtained from a member of a different species from the subject.

Xenograft rejection includes rejection of all types of xenograft and may include for example, xenografts of cornea, heart, lung, kidney, liver, pancreas, pancreatic islets, brain, bone, intestine, skin, valves, bone marrow, stem cells, hematopoietic cells or other cells from, for example, rodent, non-human primate, human, cattle, pig, sheep, camel, goat, kangaroo or horse.

In a further embodiment, the disease is an allergy. The term "allergy" will be understood by those skilled in the art to refer to a type I hypersensitivity that is associated with a T cell response, typically a Th2 response, following contact with an allergen. The allergy may be an allergy to any allergen and includes, for example, asthma, eczema, atopic dermatitis, anaphylaxis, hayfever, allergic conjunctivitis, contact dermatitis, food allergy, drug or any other chemical allergy, fungal allergy, or an allergy as defined above to any other allergens or parts thereof.

Generally, the terms "treat", "treating", "treatment" and the like are used herein to mean affecting a subject, tissue or cell to obtain a desired pharmacologic and/or physiologic effect. The effect may be prophylactic in terms of completely or partially and/or may be therapeutic in preventing a disease or sign or symptom of disease terms of a partial or complete cure of a disease.

The disease may be treated by administering to the subject a therapeutically effective amount of a composition comprising the activated $CD4^+,CD25^+$ T cells that have been grown in vitro according to the methods described above and a pharmaceutically acceptable carrier. The composition comprising activated $CD4^+,CD25^+$ T cells that have been grown in vitro according to the methods described above, may be administered parenterally in formulations containing conventional non-toxic pharmaceutically acceptable carriers, adjuvants, and vehicles.

As used herein, the term "therapeutically effective amount" is meant as an amount effective to yield a desired therapeutic response. For example, an amount sufficient to prevent or treat autoimmune disease such as those mentioned above.

The specific therapeutically effective amount will, obviously, vary with such factors as the particular condition being treated, the physical condition of the subject, the type of mammal being treated, the duration of the treatment, the nature of concurrent therapy (if any), and the specific formulations employed and the relative constituent cell populations of the subjects immune system.

As used herein, a "pharmaceutically acceptable carrier" is a pharmaceutically acceptable suspending agent, medium or vehicle for delivering a therapeutic composition to a subject. Pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975). The pH and exact concentration of the various components of the pharmaceutical composition are adjusted to maintain cell viability and activity according to routine skills in the art. See Goodman and Gilman's The Pharmacological Basis for Therapeutics (7th ed.).

Compositions comprising cytokines or antibodies can be administered, for in vivo application, parentally by injection or by gradual perfusion over time independently or together. Administration may be intravenously, intra-arterial, intraperitoneally, intramuscularly, intracavity, intraarticular, transdermally or subcutaneously. Typically, cytokines and antibodies are administered subcutaneously.

The compositions are preferably prepared and administered in dose units. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The compositions according to the invention may be administered systemically, locally or regionally to a site of immune activity, in a therapeutically effective dose. Amounts effective for this use will, of course, depend on the severity of the side effects and the weight and general state of the subject. Typically, dosages used in vitro may provide useful guidance in the amounts useful for administration of the composition, and animal models may be used to determine effective dosages for treatment of the cytotoxic side effects. Various considerations are described, eg., in Langer, Science, 249: 1527, (1990).

The compositions may be in the form of a sterile injectable suspension. This suspension may be formulated according to known methods using those agents suitable for suspending and administering cell suspensions which have been mentioned above. Among the acceptable vehicles and solvents that may be employed to suspend cells are cell culture medium, Ringer's solution, and isotonic sodium chloride solution.

Dosage levels of the composition of the present invention are of the order of about $5 \times 10^6$ to about $5 \times 10^9$ cells per kilogram body weight, with a typical dosage range between about $5 \times 10^6$ to about $5 \times 10^8$ cells per kilogram body weight per day (from about $3 \times 10^8$ cells to about $3 \times 10^{11}$ cells per patient per day). The amount of cells that may be combined with the carrier materials to produce a single dosage will vary depending upon the host treated and the particular mode of administration. For example, a formulation intended for administration to humans may contain about $5 \times 10^8$ to $5 \times 10^{11}$ cells with an appropriate and convenient amount of carrier material which may vary from about 5 to 95 percent of the total composition. Dosage unit forms will generally contain between from about $5 \times 10^8$ to $10^9$ cells.

The inventors believe that the administration of naïve $CD4^+, CD25^+$ T cells will suppress the activity of $CD4^+, CD25^-$ T cell, resulting in a general immune suppression to all antigens. The inventors believe that tolerance to a specific antigen may be increased using significantly less $CD4^+, CD25^+$ T cells activated to the specific antigen than the amount of naïve $CD4^+, CD25^+$ T cells that would need to be administered to provide a similar reduced immune response to the specific antigen.

It will be understood, however, that the specific dose level for any particular patient will depend upon a variety of factors including the activity of the cells, the age, body weight, general health, sex, diet, time of administration, drug combination and the severity of the particular disease undergoing therapy.

There are also circumstances in which tolerance to a specific antigen is undesirable. For example, tolerance to tumour cells, or to infectious agents in chronic infections, is undesirable. The invention envisages that the requirement of $CD4^+, CD25^+$ T cells activated to the specific antigen for the presence of cytokines selected from the group consisting of IL-5, IL-12, IL-23 and IFN-$\gamma$, or a biologically active fragment thereof, or a functionally equivalent molecule thereof, can be exploited to reduce or break tolerance.

Thus, in a further aspect, the invention provides a method of reducing tolerance to a specific antigen which comprises depleting $CD4^+, CD25^+$ T cells activated to a specific antigen in a subject by reducing or eliminating the activity of one or more cytokines selected from the group consisting of IL-5, IL-12, IL-23 and IFN-$\gamma$. The activity of IL-5, IL-12, IL-23 or IFN-$\gamma$ may be reduced by any methods known in the art for reducing the activity of these cytokines in a subject. Typically, the activity of IL-5, IL-12, IL-23 or IFN-$\gamma$ may be reduced by administering an effective amount of an antagonist of IL-5, IL-12, IL-23 and/or IFN-$\gamma$. Examples of antagonists include antibodies, soluble receptors or portions thereof, iRNA or siRNA, antisense molecules, etc. For example, the activity of IL-5, IL-12, IL-23 or IFN-$\gamma$ may be reduced by administering antibodies to IL-5, IL-12, IL-23 or IFN-$\gamma$. The tolerance may be further reduced by administering an effective amount of IL-2 and/or IL-4, biologically active fragments thereof, or functionally equivalent molecules thereof. Without wishing to be bound by theory, the inventors believe that the administration of IL-2 and/or IL-4, biologically active fragments thereof, or functionally equivalent molecules thereof, will activate naïve $CD4^+, CD25^+$ T cells, thereby committing these T cells to a requirement for at least one cytokine selected from the group consisting of IL-5, IL-12, IL-23 and IFN-$\gamma$, or a biologically active fragment thereof, or a functionally equivalent molecule thereof. Thus, in the absence of IL-5, IL-12, IL-23 and/or IFN-$\gamma$, biologically active fragments thereof, or functionally equivalent molecules thereof, it is anticipated that activated $CD4^+, CD25^+$ T cells will die, further reducing tolerance to the specific antigen.

Compositions comprising one or more of IL-2, IL-4, biologically active fragments thereof, or functionally equivalent molecules thereof, and/or antagonists of IL-5, IL-12, IL-23 and/or IFN-$\gamma$, such as antibodies, may be prepared and administered as discussed above in relation to compositions comprising $CD4^+, CD25^+$ T cells.

Also contemplated for use with the method of the invention are kits. As used herein, the term "kit" refers to a group of components that are capable of being used together in the methods of the invention. For example, the kit may be used to detect the presence of $CD4^+, CD25^+$ T cells in a subject capable of inducing tolerance in the subject, or in other words, a diagnostic kit, or to prepare cells for inducing tolerance to an antigen in accordance with the invention, or to administer antibody and/or cytokines to a subject. A kit may include, for example, one or more cytokines selected from the group consisting of IL-5, IL-12, IL-23 and IFN-$\gamma$, or a biologically active fragment thereof, isolated protein or a medium such as, for example, a medium suitable for the culturing of lymphocytes. The kit may further comprise one or more cytokines selected from the group consisting of IL-2 and IL-4. The kit may further comprise antigen and/or antigen presenting cells. The kit may further include instructions for applying the method of the invention using the components of the kit.

The kit may further comprise one or more specific antigens, such as, for example, a plurality of antigens for testing of tolerance to various allergens. The antigens of the kit may be present on the surface of antigen presenting cells as described herein.

In another form, kit may include antibodies to one or more of the following: IL-5, IL-12, IL-23 or IFN-γ, or a biologically active fragment thereof.

The kit may further comprise IL-2, a biologically active fragment thereof, or a functionally equivalent molecule thereof, and/or IL-4, a biologically active fragment thereof, or a functionally equivalent molecule thereof.

The invention will now be further described by way of reference only to the following non-limiting examples. It should be understood, however, that the examples following are illustrative only, and should not be taken in any way as a restriction on the generality of the invention described above. In particular, while the invention is described in detail in relation to autoimmune disease, tissue rejection and allergic reactions, it will be clearly understood that the findings herein are not limited to treatment of autoimmune disease, tissue rejection and allergic reactions.

EXAMPLES

Example 1

These studies compared proliferation of $CD4^+$ T cells to $CD4^+,CD25^+$ T cells or $CD4^+,CD25^-$ T cell subsets or combinations of these $CD4^+$ T cell subsets in Mixed Lymphocyte Cultures (MLC). Cells were prepared from lymph nodes and spleen of either naïve DA rats or DA rats that are tolerant to a fully allogenic PVG heterotopic heart graft. Tolerance was defined as non-rejection of the graft after 75 days in the absence of maintenance immunosuppression. Responses to self (DA), and to fully MHC incompatible specific donor (PVG) and fully MHC incompatible third party (Lewis) were compared. DA, PVG, Lewis share no MHC antigens and are fully allogeneic to each other. The nature of this tolerance has previously been described and can be induced in DA rats with PVG heterotopic cardiac allografts by a variety of therapies in the first 2 weeks post transplant including cyclosporine, as well as either anti-CD4 or anti-CD3 monoclonal antibody therapy (J. Exp Med. 1990, 171: 141,Transplantation, 1993, 55: 459, Transplantation 1997, 64: 1559). The MLC proliferative response of unfractionated peripheral lymphocytes to specific donor stimulation is generally comparable to that to third party (Transplantation, 1993, 55, 380-385).

Materials and Methods

Animals and procedures. DA ($RT1^a$), PVG ($RT1^c$), Lewis ($RT1^1$) and Sprague Dawley rats were bred and maintained as previously described (J. Immunol. 1998, 161; 5146). Operative procedures including heterotopic heart grafts, irradiation and preparation of lymph node and spleen cells have been previously described (J. Exp. Med 1978, 148; 878). Heterotopic heart graft survival was monitored daily by palpation for loss of contraction and swelling associated with rejection. Rejection was defined as total loss of contraction equivalent to that when there is total loss of electrocardiographic activity. Some grafts destined to become tolerant have transient swelling and reduced contractility, but recover. This is consistent with an acute inflammatory response that may be required to induce the specific tolerance mediating $CD4^+,CD25^+$ T cells.

Preparation of Peripheral Lymphoid Cells.

Single cell suspensions from spleen and lymph node cells (LNC) were prepared, as described (34) and RBC lysed by a buffer of 0.83% $NH_4Cl$, 0.1% $KHCO_3$ and 10 mM EDTA at pH 7.2. Cells were resuspended in PBS/2% BSA (MultiGel, Biosciences, Castle Hill, NSW, Australia).

Subsets were identified by mAb and indirect immunofluorescence staining, and analysis on a FACScan, as described (35). Monoclonal antibodies used were R7.2 (TCR-α,β), G4.18 (CD3), W3/25 (CD4), MRCOx8 (CD8), MRCOx39 (CD25, IL-2R alpha chain), L316 (CD122 IL-2R beta chain), (Pharmingen/Becton Dickenson, San Diego, Calif.).

Subsets of T cells were enriched by a combination of an indirect panning technique to deplete $CD8^+$ T cells and B cells, as described (9) and Magnetic bead separation techniques and a MACS column, as described by the manufacturer, (Miltenyi, Bergisch Gadenbach, Germany).

Briefly, cells were incubated at 4° C. with optimised concentrations of MRCOx8 (anti-CD8 monoclonal antibody) and MRC Ox33 (anti-CD45RA monoclonal that binds to B cells and other leucocytes except it does not bind T cells), washed three times with PBS/2% BSA then resuspended at $2 \times 10^7$ cells/ml. These cells were incubated for 30 min at 4° C. on Petri dishes (Greiner Labortechnik, Frickenhausen, Germany) coated with rabbit anti-rat Ig and anti-mouse Ig (DAKO A/s. Glostrup, Denmark). This supernatant was concentrated in 85 μl of PBS and incubated for 4° C. for 15 minutes with 13 μl of goat anti-mouse Ig micro-beads (Miltenyi) per $10^6$ cells. After washing, cells were eluted on a CS MACS column (Milentyi) to obtain 97-99% enrichment for $CD4^+$ T cells. The enriched $CD4^+$ T cells were then incubated at 4° C. for 20 min with PE conjugated MRCOx39 (anti-CD25 monoclonal antibody), then washed twice before incubation for 15 min at 4° C. with 8 μl/$10^6$ cells of mouse anti-PE mAb microbeads (Miltenyi). Cells were then eluted through a LS MACS column (Miltenyi) and were either resuspended in media with 20% Lewis rat serum for use in MLC or in PBS/2% BSA for injection to rats. The cells were 96-99% $CD4^+$ and the depleted population had <1% $CD4^+$, $CD25^{+high}$ T cells. The enriched population was 85-95% $CD4^+,CD25^{+high}$ T cells. For those experienced in the art, it is known that enriched $CD4^+,CD25^+$ T cells populations refers to the $CD4^+$, $CD25^{+high}$ T cells, as separation techniques preferentially enrich this population of $CD4^+,CD25^+$ T cells.

In some experiments $CD4^+,CD25^+$ T cells were directly enriched by incubation of unfractionated lymphoid cells at 4° C. for 20 min with PE conjugated MRCOx39, then washed twice before incubation for 15 min at 4° C. with mouse anti-PE mAb microbeads (Miltenyi). Cells were then eluted through a LS MACS column (Miltenyi) and were either resuspended in media with 20% Lewis rat serum for use in MLC or in PBS/2% BSA for injection to rats.

Mixed Lymphocyte Cultures (MLC)

Stimulator cells were from thymus of rats given 8.5 gray whole body irradiation 24 hours before. This population of stimulator cells is depleted of mature lymphocytes and is enriched for antigen presenting cells. Enriched antigen presenting cells are preferred as functional lymphoid cells will be stimulated and may produce cytokines that will activate responder cells or may produce background stimulation. Stimulator cells from whole body irradiated donors have the peripheral and thymic lymphoid cells destroyed in vivo within 24 hours. An alternate method that could be used to enrich dendritic cells could be with monoclonal antibody selection and Magnetic bead separation. The stimulator cells can also be irradiated and left over night to allow peripheral lymphocytes to die of the effects of irradiation, leaving an antigen presenting cell enriched population. $10^4$ of these stimulator cells were as effective as $2 \times 10^5$ in vitro irradiated spleen cells. The normal ratio of responder to stimulator cells is 1:1 to 2:1 when peripheral lymphoid cells are used as stimulators but when there is enrichment of antigen presenting cells by depletion of T and B lymphocytes then responders to stimulators cells may be 10-100:1.

Microcultures in U-bottom microtiter plates (Linbro, Flow Labs, VA) had $2\times10^4$ stimulators cells and either $2\times10^5$ or $1\times10^5$ responder cells/well in a total volume of 200 µl. Usually there are 4-6 replicate wells set up for each experimental sample. Cell culture medium used was RPMI 1640 (GIBCO, Grand Island, N.Y.) supplemented with 100 ng/ml penicillin, 100 U/ml streptomycin (Glaxo, Boronia, Victoria, Australia), 2 mM L-glutamine, $5\times10^{-5}$ M 2-mercaptoethanol (Sigma Chemicals, St. Louis, Mo.), and 20% Lewis rat serum. 20% Lewis rat serum produced low background stimulation. Autologous or same species serum results in a very low background stimulation. This low background is due to elimination of the response to heterologous proteins in products such as fetal calf serum that are not used in the media.

In other experiments, serial dilutions of T cells subsets were cultured with $2\times10^5$ stimulators cells. Different ratios of mixtures of $CD4^+$ T cell subsets were also cultured with $2\times10^4$ stimulators cells in limiting dilution assays.

Cells were cultured at 37° C. in humidified air containing 5% $CO_2$ and at various time points, usually at 3, 4, 5 and 6 days the cultures were pulsed with 0.5 µCi $^3$H-TdR (Amersham, Arlington Heights, Ill.) 16 hr prior to harvesting with a Titretek Cell Harvester (Flow Lab, Ayrshire, Scotland). Proliferation was assayed by adding liquid scintillation fluid before counting on a beta counter (1450 Microbeta Plus, Beckman Instruments, Palo Alto, Calif.). Other wells were harvested at 24 and 48 hours to extract mRNA for RT-PCR analysis of cytokine mRNA induction.

Results

FIG. 1A

The results of measurement of the proliferation of naïve unfractionated lymphocytes, and the enriched populations of $CD4^+,CD25^+$ T cells, $CD4^+$ T cells or $CD4^+,CD25^-$ T cells are shown in FIG. 1A. As can be seen from FIG. 1A, the response at 4 and 5 days of $CD4^+$ T cells is less that that after depletion of $CD4^+,CD25^+$ T cells as seen with the enriched $CD4^+,CD25^-$ T cells. The response of $CD4^+,CD25^+$ T cells is much smaller than with either unfractionated $CD4^+$ T cells or $CD4^+,CD25^-$ T cells. This kinetic study demonstrates that the proliferation at day 4 and 5 is most useful, to demonstrate proliferative responses for unfractionated $CD4^+$ T cells and $CD4^+, CD25^-$ T cells. The response of naïve $CD4^+,CD25^+$ T cells peaks earlier at day 3 and 4 and wanes by day 5 and 6, where as the response of unfractionated $CD4^+$ T cells and of naïve $CD4^+,CD25^-$ T cells does not appear until day 4 and peaks at days 5 or 6 before waning.

FIG. 1B

Figure 1B:
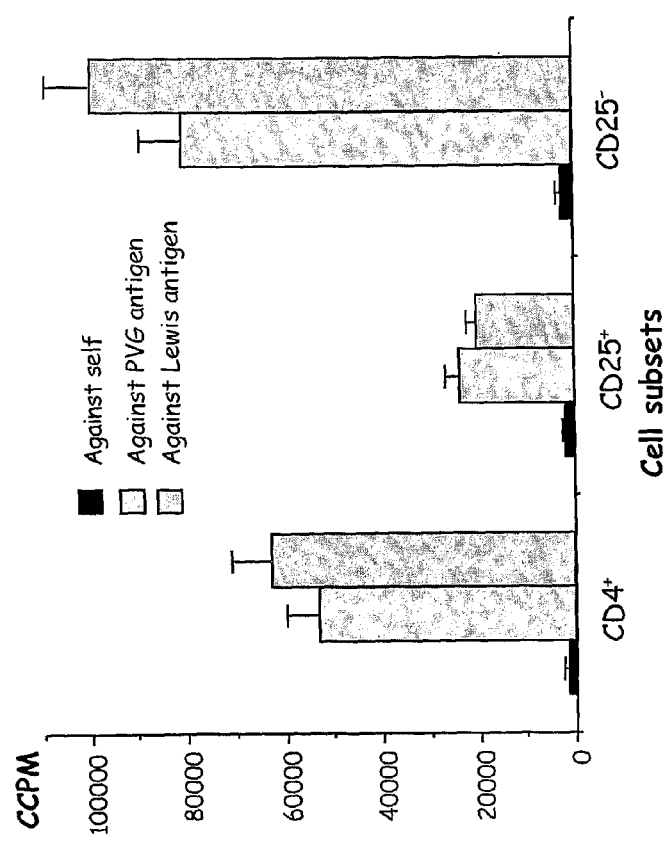
FIG. 1B is a graph comparing proliferation of naïve $CD4^+$ T cell lymphocytes, naïve $CD4^+$,$CD25^+$ T cells and naïve $CD4^+$,$CD25^-$ T cells in response to self antigen (black), PVG antigen (donor antigen) (light grey) and Lewis antigen (third party antigen) (dark grey) after 4 days.

The results of comparison of proliferation to self, and two allogeneic stimulator strains of naïve $CD4^+$ T cells, naïve $CD4^+,CD25^+$ T cells and naïve $CD4^+,CD25^-$ T cells are shown in FIG. 1B. As can be seen from FIG. 1B, the proliferative response at day 4 to syngeneic DA stimulators is low in all cases. The responses to PVG and Lewis are similar in each subtype of cells. As described above, the response of $CD4^+,CD25^+$ T cells is less than the other populations and $CD4^+,CD25^-$ T cells have a greater response than unfractionated $CD4^+$ T cells.

FIG. 1C

Figure 1C:
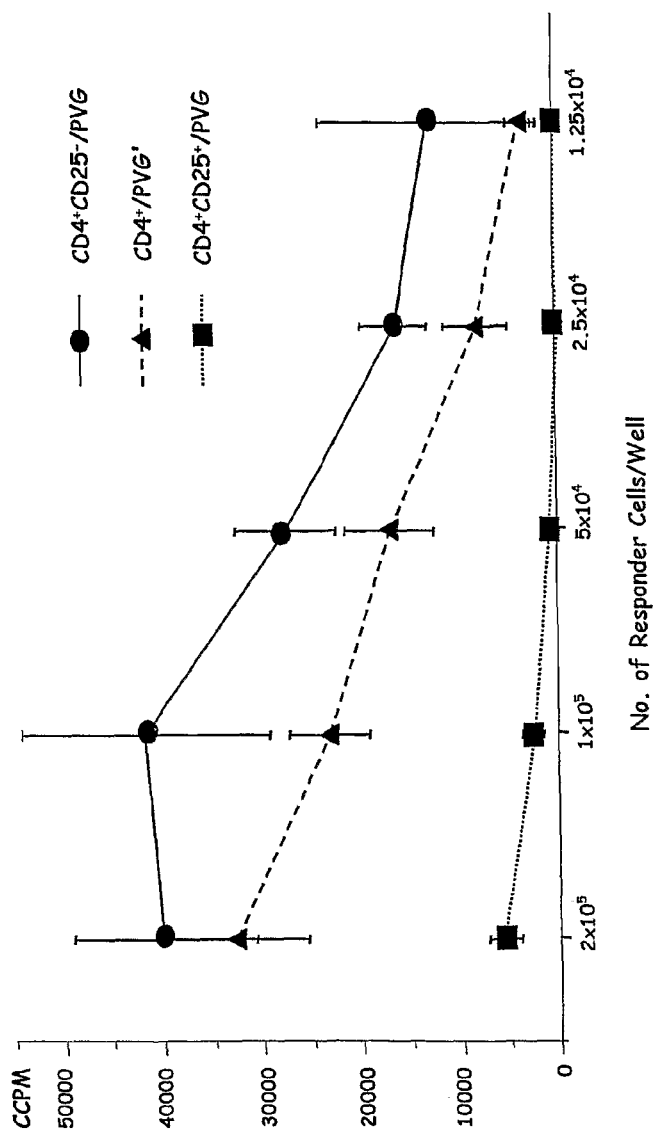
FIG. 1C is a graph of the proliferation (on y axis) of serial dilutions (shown on x axis) of populations of naïve $CD4^+$ T cell lymphocytes (triangles), naïve $CD4^+$,$CD25^+$ T cells (squares) and naïve $CD4^+$,$CD25^-$ T cells (circles) following contacting the lymphocytes with alloantigen (PVG).

FIG. 1C shows the result of serial dilution of naïve $CD4^+$, $CD4^+,CD25^+$ or $CD4^+,CD25^-$ T cells. As can be seen from FIG. 1C, at all dilutions the response by $CD4^+,CD25^-$, T cells is greater that the equivalent number of unfractionated $CD4^+$ T cells. The unfractionated $CD4^+$ T cells are a mixed population with approximately 5% naïve $CD4^+,CD25^+$ T cells and 95% $CD4^+,CD25^-$ T cells. Thus the greater proliferation of $CD4^+,CD25^-$ T cells is not simply due to an effect of enrichment (ie due to the loss of the 5% $CD4^+,CD25^+$ T cells). It is consistent with an active effect of the minority population of naïve $CD4^+,CD25^+$ T cells inhibiting the major population of $CD4^+, CD25^-$ T cells.

FIG. 1D

Figure 1D:
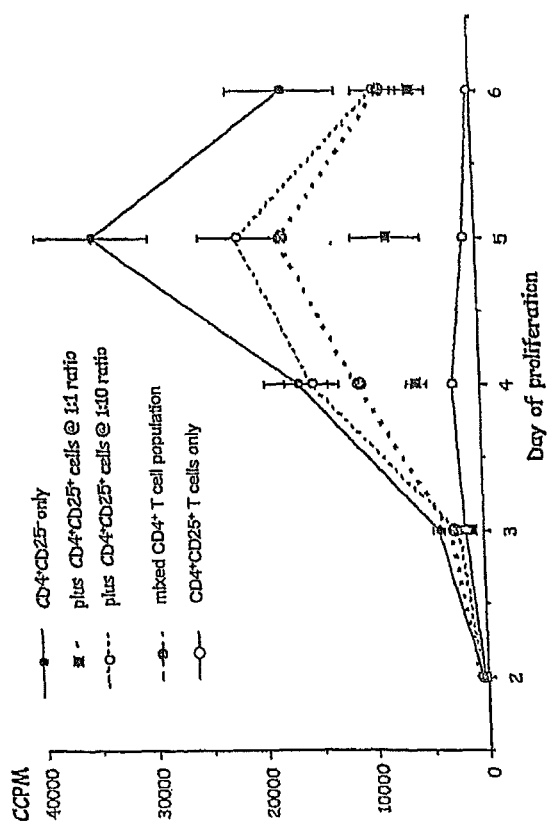
FIG. 1D is a graph of the effect on proliferation of mixing separate naïve $CD4^+$,$CD25^+$ T cells with separate $CD4^+$, $CD25^-$ T cells over 6 days following contacting the lymphocytes with alloantigen (PVG). Mixtures are as indicated.
Figure 1E:
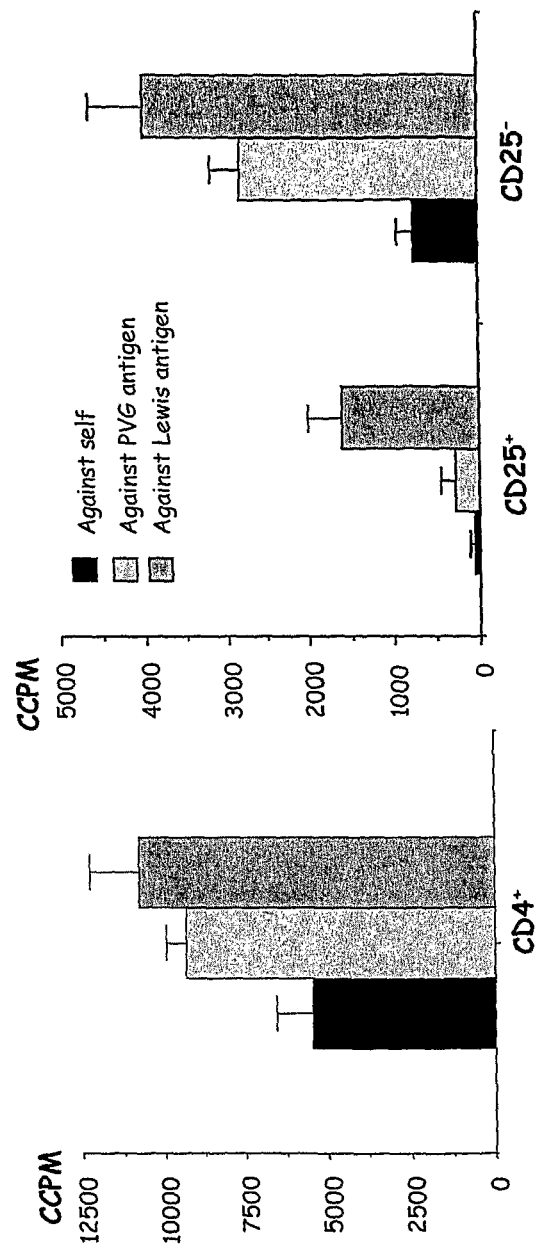
FIG. 1E is graphs of proliferation of $CD4^+$ T cells, $CD4^+$,$CD25^+$ T cells and $CD4^+$,$CD25^-$ T cells from DA rats tolerant to a PVG cardiac allograft following contacting the lymphocytes with self antigen (black), donor antigen (PVG antigen—light grey) or third party antigen (Lewis—dark grey).

The effect of admixing separated naïve $CD4^+,CD25^+$ T cells with separated naïve $CD4^+,CD25^-$ T cells was examined and the result is shown in FIG. 1D. As can be seen from FIG. 1D, naïve $CD4^+,CD25^+$ T cells had an active suppressor effect $CD4^+,CD254^-$ T cells. In these experiments 1:10 mixes of $CD4^+,CD25^+$ with $CD4^+, CD25^-$ T cells resulted in proliferative responses similar to the mixed population in $CD4^+$ T cells where the ratio is 1:10-1:20. Increasing the ratio to 1:1 resulted in near total suppression of the proliferative responses. This is consistent with the demonstrated non-specific inhibitory effect of naïve $CD4^+,CD25^+$ T cells on immune responses in vitro.

FIG. 1E

Illustrates the proliferation of $CD4^+$ T cells, $CD4^+,CD25^+$ T cells or $CD4^+,CD25^-$ T cells from tolerant animals. The response at 4 and 5 days of $CD4^+$ T cells is similar to the tolerated strain (PVG) as it is to third party Lewis. After depletion of $CD4^+,CD25^+$ T cells, as seen with the enriched $CD4^+,CD25^-$ T cells, the proliferative response to the tolerated strain is less than to the third party strain.

The response of $CD4^+,CD25^+$ T cells is much smaller than with either unfractionated $CD4^+$ or $CD4^+,CD25^-$ T cells. These $CD4^+,CD25^+$ T cells do not respond to specific donor in that their response is similar to the response to self (DA). These $CD4^+,CD25^+$ T cells from tolerant animals retain their response to third party, which is greater than to either specific donor or self.

The response to self (DA) is less in all cultures than that to fully allogeneic stimulators, PVG or Lewis. The response to PVG and Lewis which are MHC unrelated strains is similar for unfractionated $CD4^+$ T cells, but is less to PVG than to Lewis for both $CD4^+,CD25^+$ T cells and $CD4^+,CD25^-$ T cells.

These results suggested that the $CD4^+,CD25^+$ T cells from tolerant animals die in standard culture conditions. Thus they do not inhibit the $CD4^+,CD25^-$ T cells in the mixed population of unfractionated $CD4^+$ T cells, thereby their removal does not lead to an enhanced response of enriched $CD4^+$, $CD25^-$ T cells. Alone $CD4^+,CD25^+$ T cells do not respond to donor alloantigen, again consistent with them not surviving, and their possible dependence on cytokines for growth.

FIG. 1F

Shows serial dilution of $CD4^+$, $CD4^+,CD25^+$ T cells or $CD4^+,CD25^-$ T cells from DA rats tolerant to PVG heart allografts. At all dilutions the response to specific donor (PVG) by $CD4^+,CD25^-$ T cells is less that the response to third party (Lewis) and no greater than that to self (DA). In contrast, with unfractionated peripheral lymphocytes or with $CD4^+$ T cells the response to specific donor (PVG) is similar to third party (Lewis) and greater than to self (DA). At all dilutions the response of $CD4^+,CD25^-$ T cells to third party (Lewis) or to self (DA) is much greater than the equivalent number of unfractionated $CD4^+$ T cells.

This study demonstrates that the response to PVG by $CD4^+,CD25^-$ T cells compared to Lewis is reduced and is different to that observed with naïve $CD4^+,CD25^-$ T cells where there was a similar increase to both PVG and Lewis above that observed with unfractionated $CD4^+$ T cells. Further, naïve $CD4^+,CD25^-$ T cells response to PVG is always greater than to self.

This study suggested that the response of unfractionated CD4+ T cells from tolerant animals is due to a diminished response of the CD4+,CD25- T cells to PVG being unchecked by CD4+, CD25+ T cells in the absence of cytokines capable of stimulating activation of CD4+,CD25+ T cells or of prolonging survival or stimulating proliferation of activated CD4+CD25+ T cells. In contrast CD4+,CD25+ T cells from animals tolerant to PVG retain the capacity to inhibit the response to third party Lewis and their removal allowed an enhanced response of CD4+,CD25- T cells to Lewis compared to unfractionated CD4+ T cells.

These studies demonstrated that there is a difference in the CD4+,CD25+ T cells in tolerant animals compared to naïve. This is consistent with the CD4+,CD25+ T cell from tolerant host dying in culture without critical growth factors, and that it thereby cannot suppress in this assay. Alternately the activation of CD4+,CD25- T cells results in a change of cytokine milieu that destroys rather than promotes the function of specific CD4+,CD25+ T cells that are maintaining tolerance. That is, new activation and release of early T cell activation cytokines destroys the specific tolerance mediating CD4+, CD25+ T cells.

Conclusions

In mixed lymphocyte cultures (MLC), the proliferative response of CD4+,CD25+ T cells:

a) to MHC incompatible alloantigens can be reproducibly assayed with the defined culture conditions that eliminate any background.
b) from naïve animals is only to MHC incompatible stimulators, not to self.
c) from naïve animals inhibits the proliferation of naïve CD4+,CD25- T cells.
d) from tolerant animals is only to third party and not to specific donor or self.
e) from tolerant animals cannot inhibit the response of tolerant CD4+,CD25- T cells to specific donor but can inhibit the response to third party.
f) From naïve animals has a non-alloantigen specific suppressor effect, in distinction from those from tolerant animals that retain the capacity to suppress response to third party alloantigen but not to specific donor alloantigens in the absence of cytokines capable of stimulating activation of CD4+,CD24+ T cells or of prolonging survival or stimulating proliferation of activated CD4+ CD25+ T cells.

Example 2

The following experiments examined the effects of various cytokines on the proliferative response in MLC of CD4+, CD25+ T cells, and the response of naïve and tolerant enriched CD25+,CD4+ T cells to individual cytokines was compared.

Materials and Methods

Cytokines were produced as described, and include IL-2 (32, 33) and one unit was defined as that required to induce 50% of maximal proliferation of the IL-2 dependent CTLL line. The cloning production and assaying of these cytokines has been described and used standard methods for transfection into CHO—K1 cells (Transplantation Proc. (1999) 31, 1574-5, 1999 and 31, 1572, 1999) and included IL-4, IL-5, IFN-γ, IL-10, IL-12 (p70), IL-12 (p40), IL-13. Human TGF-β was purchased from Sigma. Cytokine was added to each relevant well as a 50 μl aliquot of CHO—K transfected cell line supernatant. These supernatants have 5000-50,000 units per ml. Thus the relevant cytokines were at a final concentration of 1000-12,000 units per ml. Controls had supernatant from a non transfected CHO—k1 cell line added to the medium.

Reverse transcription—polymerase chain reaction (RT-PCR): The methods for mRNA extraction, cDNA synthesis and semi-quantitative PCR have been described (31, 35). All samples were standardized by quantitation of cDNA by spectroscopy and by PCR of the house-keeping gene GAPDH. The primers and optimal cycle conditions for the cytokines IL-2, IL-4, IL-S, IL-10, IFN-γ, TNF-α, have been described (Transplantation 1998; 1145-1142). Primers for IFN-γ receptor and IL-S-receptor alpha chain were designed and validated. Reaction and amplification conditions were optimised for each primer set using a PCR machine (Corbett Research, Sydney, NSW, Australia). PCR product was then analysed by electrophoresis on 6% polyacrylamide gels and stained with ethidium bromide. The specificity of the RT-PCR products were verified by Southern transfer and hybridisation with dideoxygenin (DIG) 3'-end labelled oligonucleotide probes. Hybridised probe was detected using the DIG luminescent detection kit (Boehringer Mannheim). The methods for the semi-quantitative technique RT-PCR used were as previously described (Transplantation 1997, 64; 1559-1567). Starting cDNA samples were assayed at neat, 10, 100 and 1000 fold dilutions and reactions terminated at a cycle in the optimum range for each product. For most samples there were duplicate samples assayed at each dilution. Levels of mRNA expression were compared using the lowest dilution at which the PCR product was detected. Negative controls without cDNA, and positive controls of cDNA from ConA stimulated rat lymphocytes, were included in all experiments.

Results

Enriched CD4+,CD25+ T cells were cultured in MLC against self (DA), specific donor (PVG) and third party (Lewis) stimulators. Cultures were assayed for proliferation at 3-4 days as described above.

FIG. 2A

Figure 1F:
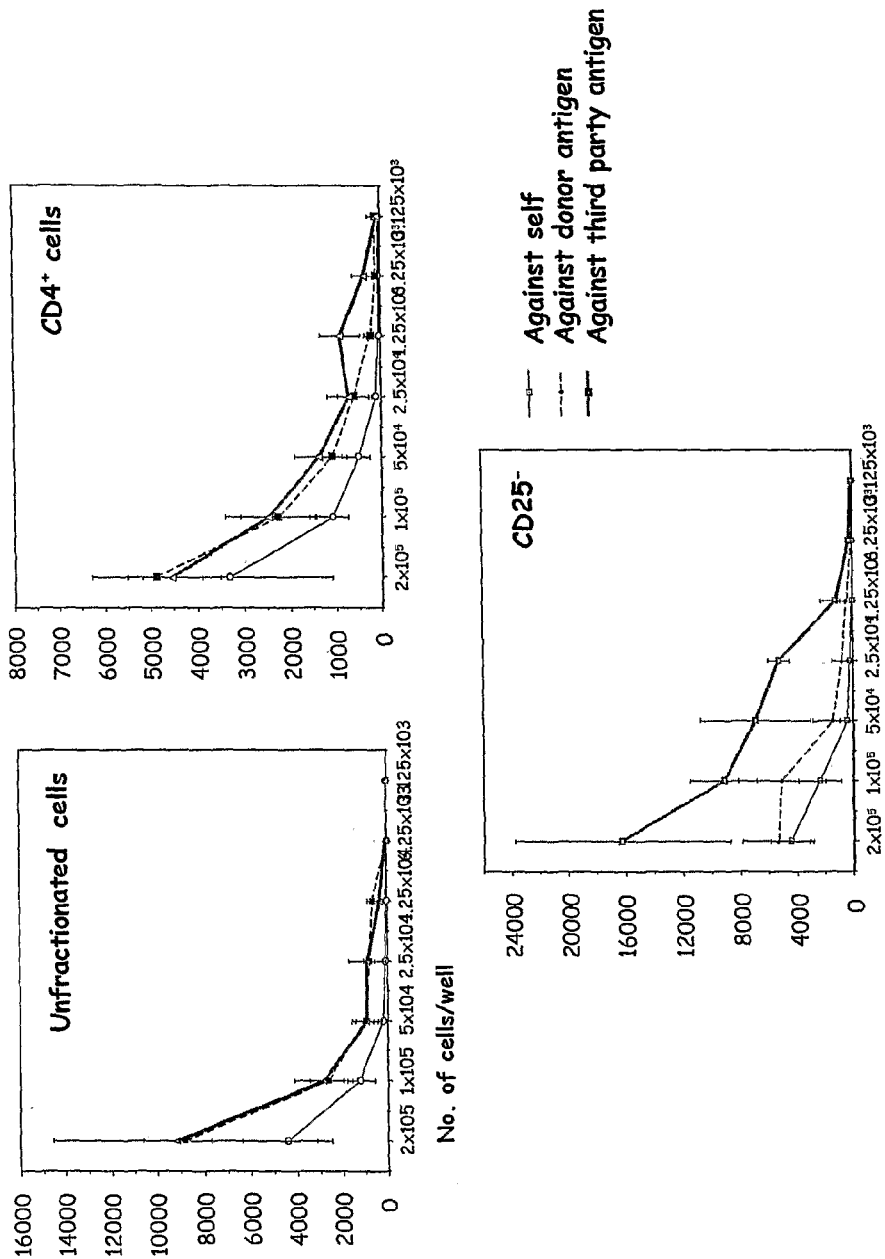
FIG. 1F is graphs showing the results of a limiting dilution assay of unfractionated T cells, fractionated $CD4^+$ T cells and fractionated $CD4^+$,$CD25^-$ T cells from DA rats tolerant to a PVG allograft at day 4 following contacting the lymphocytes with self antigen (open circles, full thin line), donor antigen (dashed line) or third party antigen (thick line, open squares).
Figure 2A:
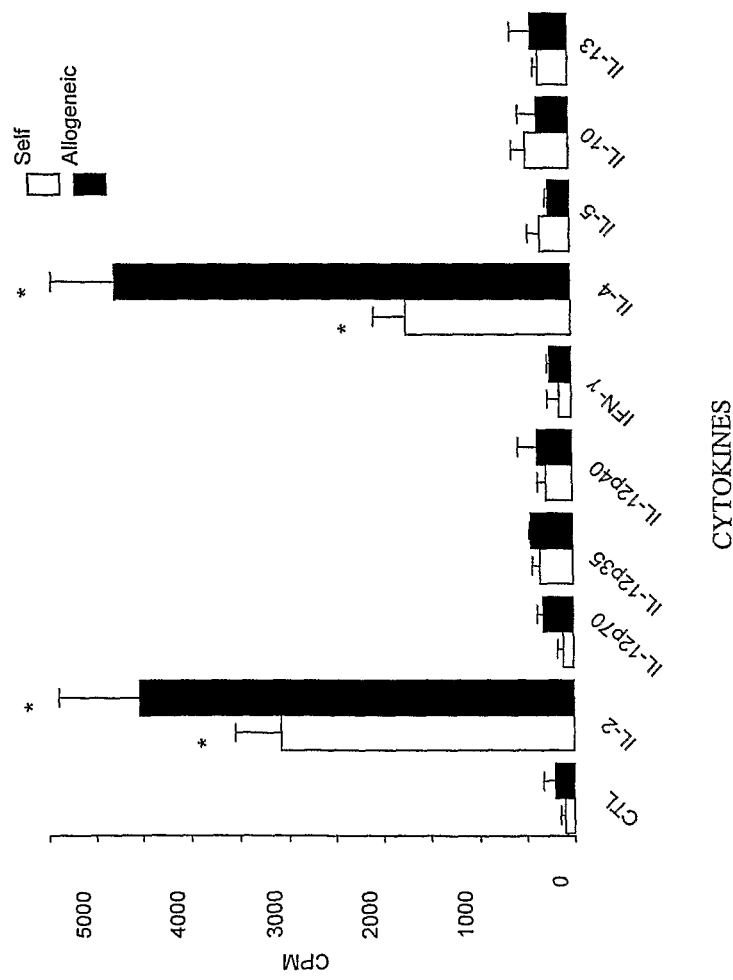
FIG. 2A is a graph of proliferation of naïve $CD4^+$,$CD25^+$ T cells following contact with self antigen (black) or donor antigen (cross-hatch) and incubation in the presence of cytokines as indicated.

FIG. 2A illustrates the response of naïve DA cells to either DA antigen or PVG antigen in the presence of cytokines as indicated. As can be seen from FIG. 2A, only IL-2 and IL-4 resulted in enhanced proliferation of naïve CD4+,CD25+ T cells. These cytokines enhance proliferation to self, and both allogeneic stimulators, to a similar degree. This is consistent with poly-clonal activation by either IL-2, or IL-4. Addition of IL-5, IL-10, IL-13, IFN-γ did not enhance proliferation of naïve CD4+,CD25+ T cells. Note the background response to self is at approx 100 cpm, equivalent to counts obtained with distilled water. That is with the methods used, (as described in FIG. 1) there was no non-specific proliferation to extraneous factors like media, or stimulator cells. The background counts are equivalent to having distilled water assayed.

FIG. 2B

Figure 2B:
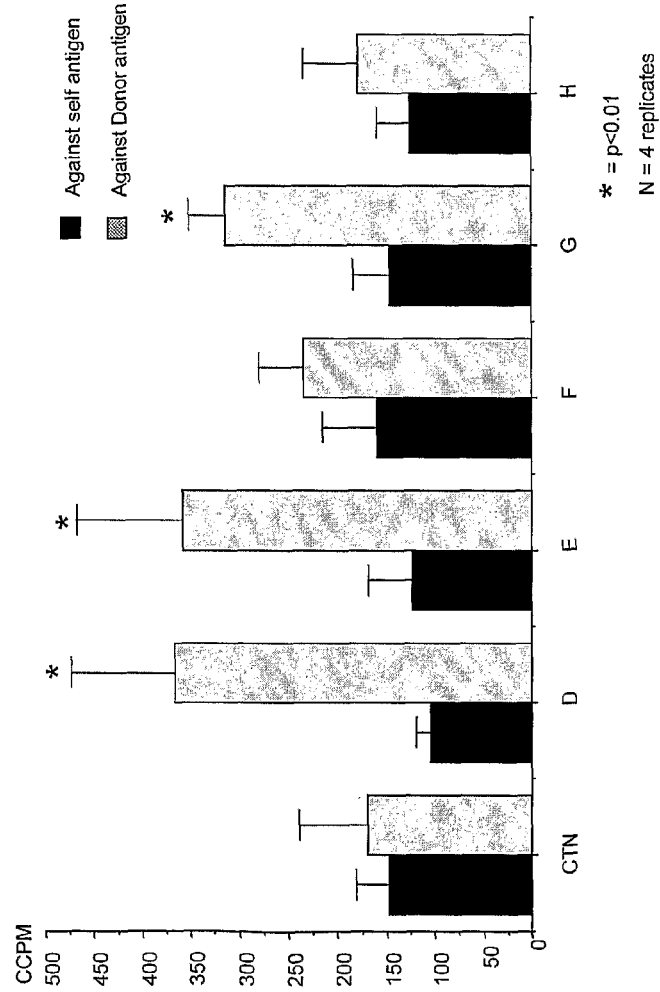
FIG. 2B is a graph of proliferation at day 3 of activated $CD4^+$,$CD25^+$ T cells against self antigen (black) or donor antigen (grey) in the presence of TGF-β(D), IFN-γ(E), IL-12 (p7O) (F), IL-5(G) or IL-10(H).

FIG. 2B is a graph showing the proliferation at day 3 of activated CD4+,CD25+ T cells against self-antigen (black) or donor antigen (grey) in the presence of TGF-β (D), IFN-γ (E), IL-12p70 (F), IL-5 (G), or IL-10 (H). FIG. 2B shows that the response of activated CD4+,CD25+ T cells is different to that of naïve CD4+,CD25+ T cells in several aspects. First as described in FIG. 1E, activated CD4+,CD25+ T cells do not proliferate to specific donor in the absence of specific cytokines and thereby differ from naïve CD4+,CD25+ T cells. Activated CD4+,CD25+ T cells proliferate to third party Lewis in a manner similar to naïve CD4+,CD25+ T cells. Both activated and naïve CD4+,CD25+ T cells do not proliferate to self (DA). The addition of IL-2 or IL-4 to cultures resulted in polyclonal activation, like that observed with naïve CD4+, CD25+ T cells (data not shown), in that there was a marked enhanced proliferative response of naïve CD4+,CD25+ T cells to self (DA), specific donor (PVG) and third party (Lewis).

The response to other cytokines identified a different pattern for activated CD4+,CD25+ T cells to the specific donor PVG for some cytokines but not others. Activated CD4+, CD25+ T cells response to both self (DA) and third party Lewis stimulators were similar to that of naïve cells for all cytokines.

Thus these experiments demonstrated a different response to PVG (donor or specific antigen), that was most consistent with IFN-γ and IL-5. IL-12 (p70) and TGF-β also showed an effect. Control cultures and those with cytokines that did not induce proliferation, had responses at background, approx. 100 cpm.

These experiments demonstrated that CD4+,CD25+ T cells activated to a specific antigen require either IL-5, IL-12 or IFN-γ to grow and survive.

Conclusions

Cytokines have different effects on naïve and tolerant CD4+,CD25+ T cells.
  a) IL-2 and IL-4 markedly enhance proliferation of CD4+, CD25+ T cells from naïve or tolerant cell donors to self, specific donor and third party.
  b) IL-5 and IFN-γ only enhances proliferation of tolerant CD4+,CD25+ T cells to specific donor and not to self or third party. They have no effect on naïve CD4+,CD25+ T cells proliferation to self or to alloantigens.

Example 3

These studies examine the ability of CD4+,CD25+ T cells to transfer tolerance to a host.

Materials and Methods

Adoptive Transfer Assays.

These were conducted as described (J. Exp. Med 1978, 148; 878-889 and Transplantation 1993, 55; 374-379). Briefly, DA rats were irradiated with 7.5-8.5 gray from a $^{60}$Co source, then grafted with heterotopic adult heart from a PVG donor that had also been irradiated (FIG. 3 A). This source of irradiation required treatment over 15-30 minutes, as described (J. Exp. Med 1978, 148; 878-889). In the later experiments the irradiation source was a linear accelerator and whole body irradiation was delivered in 2-3 minutes. These irradiated hosts were given a heterotopic heart graft and also were restored within twenty-four hours of irradiation with CD4+ T cells, either unfractionated or enriched for CD4+,CD25− T cells or CD4+,CD25+ T cells. Heart graft rejection is monitored initially by daily palpation and if there is doubt by ECG monitoring. Rejection is scored when there is loss of all palpable contraction that is equivalent to total loss of electrocardiograph activity.

Results

Figure 3A:
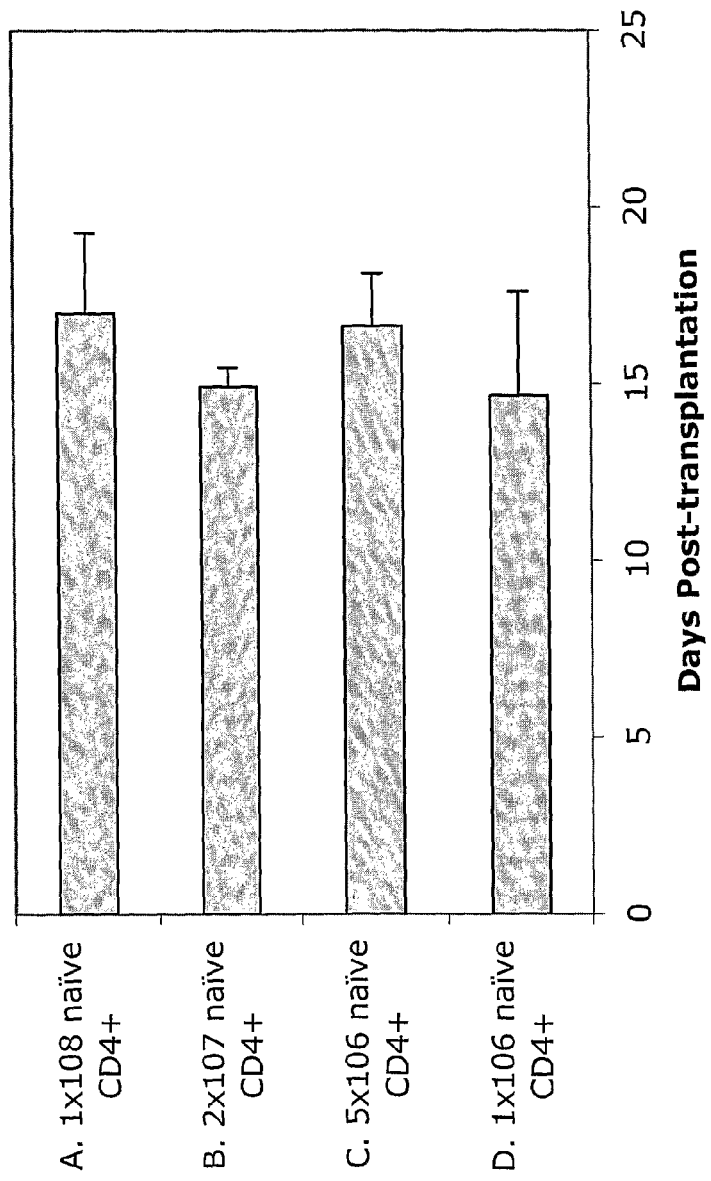
FIG. 3A is a graph of rejection time of heart allografts in rats following whole-body irradiation and administration of various doses (as indicated at A to D) of naïve $CD4^+$ T cells/lymphocytes.
Figure 3B:
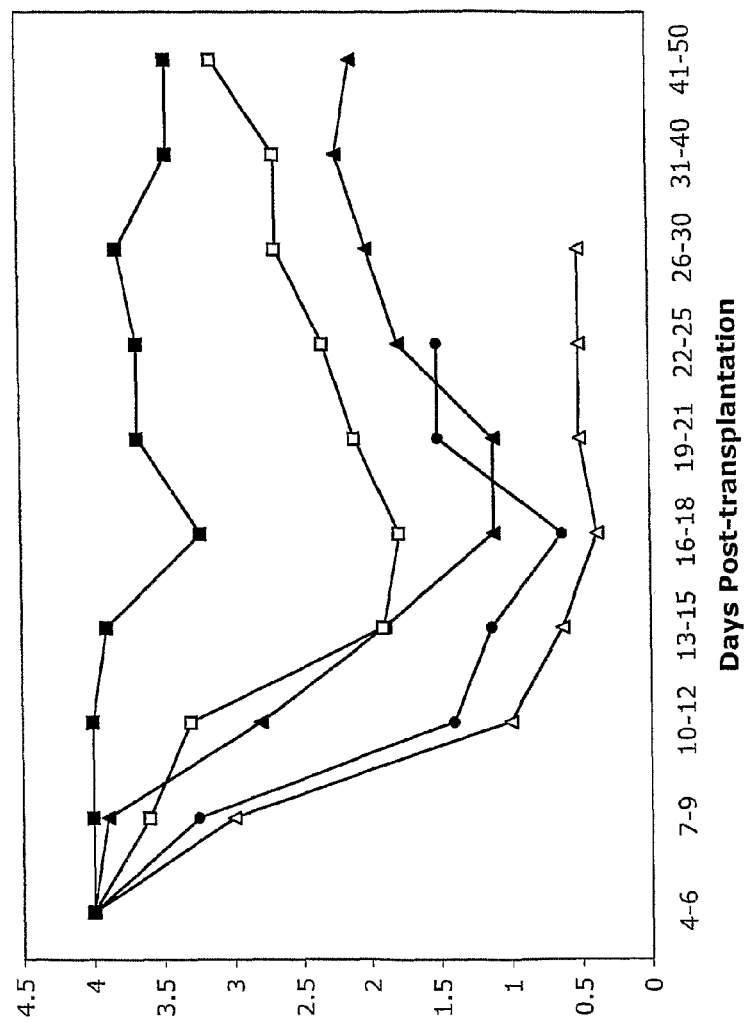
FIG. 3B is a graph of heart graft function up to 50 days post-transplantation in rats following administration of A, $5 \times 10^6$ naïve CD4$^+$ T cell lymphocytes (closed triangles); B, $20 \times 10^6$ naïve CD4$^+$ T cells (closed circles); C, $5 \times 10^6$ naïve CD4$^+$,CD25$^-$ T cells (open triangles); D, $0.5 \times 10^6$ naïve CD4$^+$,CD25$^+$ T cells plus $5 \times 10^6$ naïve CD4$^+$ T cells (open squares); E, $5 \times 10^6$ naïve CD4$^+$,CD25$^+$ T cells plus $5 \times 10^6$ naïve CD4$^+$ T cells (closed squares).

FIGS. 3A and 3B show the capacity of naïve CD4+ T cells to effect rejection response on adoptive transfer to irradiated hosts.

For the studies reported in FIG. 3B a semi-quantitative scale was used where a score of 4+ indicated robust contraction with normal auxiliary heart graft rate. 3+ indicated minor slowing and or reduced contractility. 2+ indicated obvious slowing and swelling of the graft but clear palpation of beat. 1+ indicated marked slowing and poorly palpable beat, usually associated with markedly reduced amplitude of the ECG. 0 indicated no palpable contraction and equivalent to no detectable ECG activity.

FIG. 3A

FIG. 3A shows a comparison of rejection time in adoptive irradiated DA rats restored with different doses of naïve CD4+ cells. Data combined from all laboratories and sites of Prof B. Hall. Group A, n=7; Group B, n=17; Group C, n=86; Group D, n=6. To alter the balance of cells in a host, adoptive transfer experiments were performed where the DA hosts own lymphocytes were destroyed by near lethal whole body irradiation (700-850 rads). In this model, heterotopic PVG heart grafts are not rejected by the whole body irradiated hosts, whilst in non irradiated hosts rejection occurs in 6-9 days which is first set rejection time. Restoration of the irradiated host with an enriched population of CD4+ T cells restores a rejection response, but not to the normal first set time. There is no dose response with these cells, in that 5 million CD4+ T cells are as effective as 20 or 100 million CD4+ T cells. The rejection time on average is >12 days with these cells.

TABLE 1

Rejection of PVG heterotopic cardiac allografts in irradiated DA recipients restored with unfractionated CD4+ T cells and/or subpopulations of CD4+ T cells

| | Irradiation | Restorative Inoculata Subtype | Number | Graft rejection times in days median | actual | significance* p |
|---|---|---|---|---|---|---|
| 1 | − | − | − | 8 | 7(3), 8(5), 9(1) | <0.001 |
| 2 | + | — | — | >100 | >100(10) | <0.001 |
| 3 | + | CD4+ | 5 × 10$^6$ | 11 | 8, 11(11), 13, 15, >100 | |
| 4 | + | CD4+, CD25− | 5 × 10$^6$ | 9 | 8, 9(3), 10(3) | <0.001 |
| 5 | + | CD4+, CD25+ | 5 × 10$^6$ | >100 | >100(5) | <0.001 |
| 6 | + | CD4+CD25+, CD4+ | 5 × 10$^6$ 5 × 10$^6$ | >100 | >100(5) | <0.001 |
| 7 | + | cultured IL-2 CD4+, CD25+ CD4+ | 5 × 10$^6$ 5 × 10$^6$ | >100 | >100(3) | <0.01 |
| 8 | + | cultured IL-2 CD4+, CD25+ | 5 × 10$^6$ | >100 | >100(3) | <0.01 |

*Compared to 5 × 10$^6$ CD4+ T cells (see row 3)

The effects of enriched naïve CD4+ T cells, CD4+,CD25+ T cells or CD4+,CD25− T cells in the adoptive DA host with a PVG allograft were compared and the results are shown in Table 1. As in FIG. 3A, unfractionated naïve CD4+ T cells did not restore first-set rejection time but restored rejection to a median of 11 days. In this model the irradiation source was different to that in FIG. 1. CD4+,CD25+ T cells had no capacity to effect rejection, and no grafts rejected. CD4+,CD25- T cell restored rejection to near first-set tempo. Admixing naïve CD4+,CD25+ T cells with naïve CD4+ T cells in a ratio of 1:1 prevented restoration of rejection, and the grafts appeared to function without a significant rejection episode for over 100 days. CD4+,CD25+ T cells expanded by culture for three days with donor antigen (PVG) and IL-2 to expand the numbers suppressed naïve CD4+ T cells. This was done as described in methods for mixed lymphocyte culture, but in bulk in 50 ml tissue culture flasks. These results demonstrate that naïve CD4+,CD25+ T cells can be cultured with donor antigen and expanded in vitro to maintain suppressor function and not acquire the capacity to effect rejection.

FIG. 3B

The effects of varying the ratios of naïve CD25+,CD4+ T cells to naïve CD25-,CD4+ T cells in the restorative inoculum on rejection times in irradiated adoptive hosts was examined and a graph of the results is shown in FIG. 3B.

FIG. 3B illustrates heart graft function up to 50 days post-transplantation in rats following administration of; A, $5 \times 10^6$ naïve CD4+ T cells (closed triangles) (n=9); B, $20 \times 10^6$ naïve CD4+ T cells (closed circles) (n=4); C, $5 \times 10^6$ naïve CD4+, CD25-, T cells (open triangles) (n=4); D, $0.5 \times 10^6$ naïve CD4+,CD25+ T cells plus $5 \times 10^6$ naïve CD4+ T cells (open squares) (n=9): E, $5 \times 10^6$ naïve CD4+,CD25+ T cells plus $5 \times 10^6$ naïve CD4+ T cells (closed squares) (n=9). On this scale rats given 20 million CD4+ T cells effected rejection most rapidly and those given CD4+,CD25- T cells had a similar rapidity of rejection. Those given 5 million CD4+ T cells alone rejected less rapidly than those restored with CD25-, CD4+ T cells. Mixing 0.5 million CD4+,CD25+ T cells with 5 million CD4+ T cells further slowed the rejection processes, in that grafts were not totally rejected but had poor function long term. In these animals the ratio of CD25+, CD4+ T cells:CD25-, CD4+ T cells was 1:5-10 compared to 1:20-40 in those given unfractionated cells.

Mixing 5 million CD4+,CD25+ T cells with 5 million CD4+ T cells totally suppressed rejection with all grafts surviving indefinitely with very good function.

These studies demonstrate that the naïve CD4+,CD25+ T cells can suppress naïve CD4+, CD25- T cells if present in a ratio approaching 1:1.

Further it shows that expansion of CD4+, CD25+ T cells by culture with IL-2 may allow production of sufficient self suppressor T cells to achieve such ratios, if the host is depleted of CD4+,CD25- T cells or the CD4+,CD25- T cells function is impaired. Culture of naïve CD4+,CD25+ T cells with donor antigen does not convert these cells into ones that can effect rejection. Thus culture of naïve CD4+,CD25+ T cells may expand the number of suppressor CD4+,CD25+ T cells. Treatment of unfractionated CD4+ T cells in vitro with IL-4, does not enhance the tolerance effect of that CD4+,CD25+ T cells, indicating enriched CD4+,CD25+ T cells must be used. (Data not shown)

Conclusions

Altering the balance of CD4+,CD25+ T cells to CD4+, CD25- T cells in vivo can lead to tolerance, manifest by experiments with naïve cells used to restore rejection in irradiated hosts;

a) Naïve unfractionated CD4+ T cells do not show a dose response effect, suggesting there is a homeostatic balance of the 1-10% CD4+,CD25+ T cells against the >90% CD4+,CD25- T cells.

b) Removal of the 1-10% CD4+,CD25+ T cells, allows the CD4+,CD25- T cells to effect rapid rejection, confirming that the naïve CD4+,CD25+ T cells in their natural mixed population in naïve CD4+ T cells function to moderate rejection.

c) CD4+,CD25+ T cells alone do not effect rejection and can inhibit rejection when the ratio of naïve CD4+, CD25+ T cells to naïve CD4+,CD25- T cells is increased, with near total suppression of rejection when the ratio is 1:1.

d) Naïve CD4+,CD25+ T cells when expanded in MLC with specific donor antigen and IL-2 retain the capacity to suppress at 1:1 ratio and do not revert to cells that effect rejection.

Example 4

This study examines proliferation of CD4+,CD25+ T cells following contact with antigen in the presence of IL-2 or IL-4.

FIG. 4A

Figure 4A:
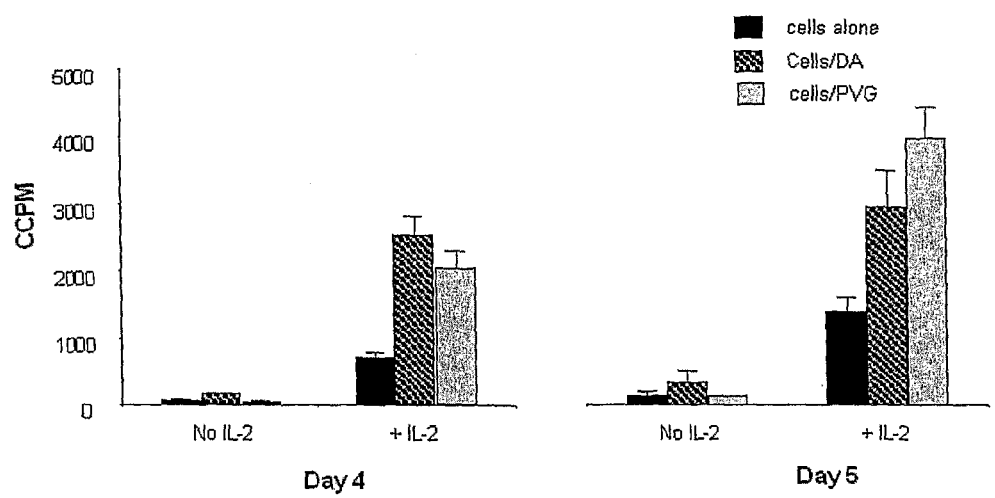
FIG. 4A is graphs showing the effect of IL-2 (upper) and IL-4 (lower) on proliferation of naïve CD4$^+$,CD25$^+$ T cells from DA rats alone (black), in contact with self antigen (cross-hatch) or in contact with alloantigen (PVG) (shaded) following 4 and 5 days after contact with antigen as indicated.
Figure 4A:
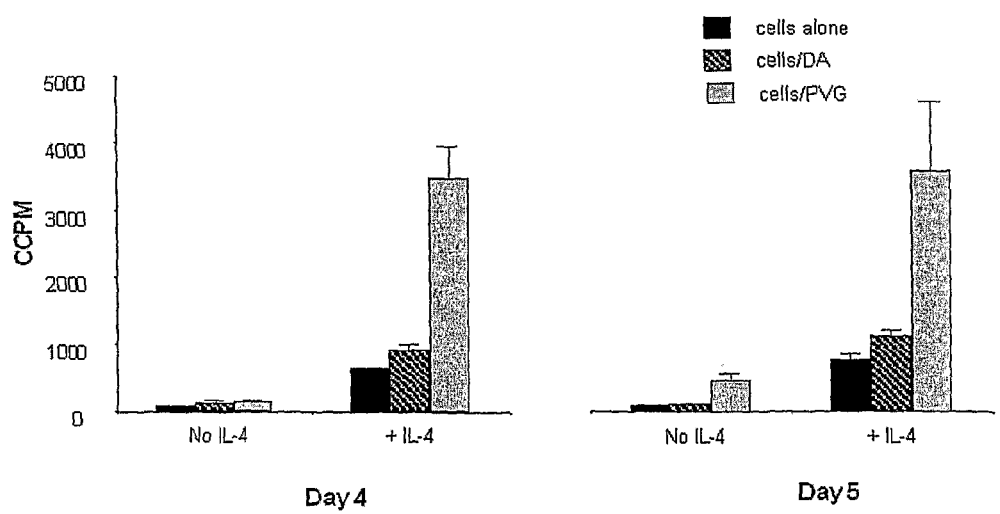

FIG. 4A shows the results of culture of naïve CD4+,CD25+ T cells from DA rats with no stimulator cells ie. no antigen (first column), self stimulator cells ie. antigen presenting cells presenting antigen from DA rats (middle column), or allogeneic PVG stimulator cells ie. antigen presenting cells presenting antigen from PVG rats.

The top panel of FIG. 4A shows the effect of contacting naïve CD4+,CD25+ T cells with antigen in the presence of IL-2. As can be seen from FIG. 2, contact with PVG antigen in the presence of IL-2 resulted in increased proliferation in all assays, with greater effect at day 5 than day 4. The proliferation to self and allogeneic stimulator cells, was similar, and that to no stimulators much less.

The bottom panel of FIG. 4A shows the effect of contacting naïve CD4+,CD25+ T cells with antigen in the presence of IL-4. The response to allogeneic was greater than that to self or those with no stimulators. This suggests the effect of culturing CD4+,CD25+ T cells in the presence of IL-4 is greater when the cells are contacted with specific antigen rather than with self antigen.

FIG. 4B

Figure 4B:
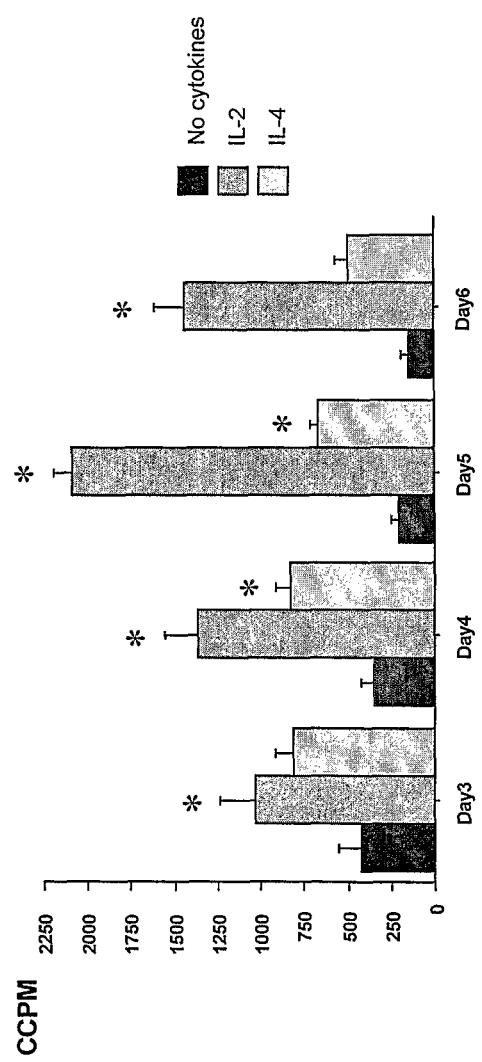
FIG. 4B is a graph showing the effect from day 3 to day 6 on proliferation of naïve CD4$^+$,CD25$^+$ T cells cultured with alloantigen and no cytokines (dark shading), IL-2 (mid-shading) or IL-4 (light shading).

FIG. 4B illustrates a time course of proliferation of naïve CD4+,CD25+ T cells from DA rats cultured with allogeneic PVG stimulator cells. Cells cultured with no cytokine supplementation had peak proliferation at day 3 as described in FIG. 1A. No proliferation was detectable at day 5 and day 6 with counts at background (equal to distilled water counts <150 ccpm). IL-2 induced marked proliferation at all days with a peak at day 5. IL-4 enhanced proliferation on all days and this proliferation peaked at day 4. Profiles of the phenotype of these cells after 3-4 days in culture shows there is an emergence of a double positive population that expresses both CD8 and CD4 (10-35% of cells) and continue to express CD25. The original cells were <1% CD4+, CD8+ cells, and <2% CD8+ T cells.

FIG. 4C

Figure 4C:
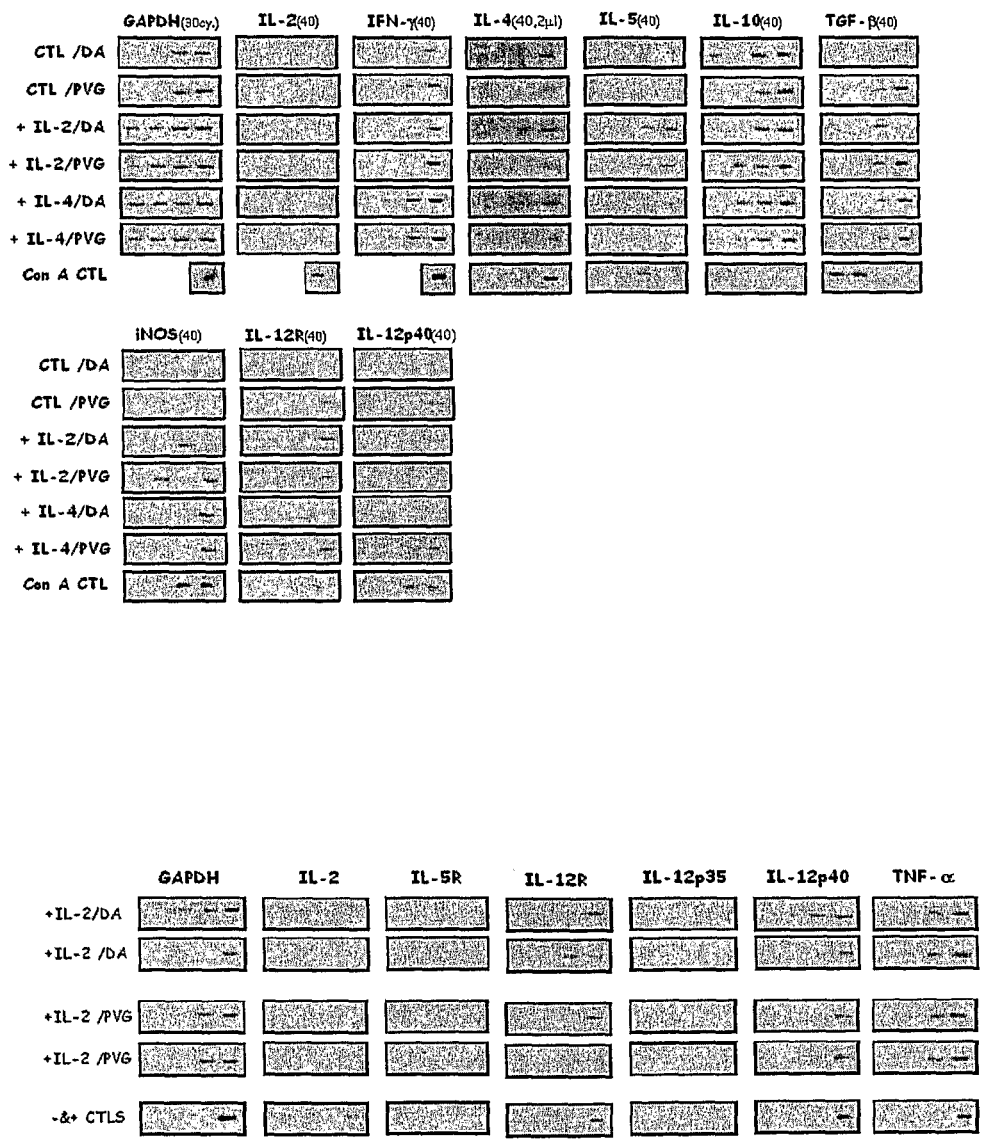
FIG. 4C shows the results of semi-quantitative RT-PCR using primers to cytokines or cytokine receptors (as indicated) on mRNA isolated from naïve CD4$^+$,CD25$^+$ T cells cultured in the presence of self or alloantigen and IL-2 or IL-4 as indicated.

FIG. 4C shows the result of a semi-quantitative RT-PCR assay for mRNA expression of cytokines and cytokine receptors by CD4+,CD25+ T cells cultured with IL-2 and IL-4.

Two experiments are shown in which naïve CD4+,CD25+ T cells were cultured in MLC with IL-2, IL-4 or controls with CHO—k1 cell supernatants. Culture was for 3 days before mRNA was extracted. Semi-quantitative RT-PCR was performed as described (Transplantation, 1997, 64, 1559-1567). The samples are serial dilutions of cDNA from right to left.

The results show that there was no induction of IL-2 by any treatment, but abundant mRNA for IL-4, IL-5, IL-10, IL-13, IFN-γ and inducible nitric oxide synthetase. Those cells cultured with IL-2 expressed IL-12Rβ2 that was not expressed in those cultured with IL-4. With IL-2 there was no IL-5Rα expression but in other experiments this receptor is induced by culture with IL-4.

FIG. 4D

Figure 4D:
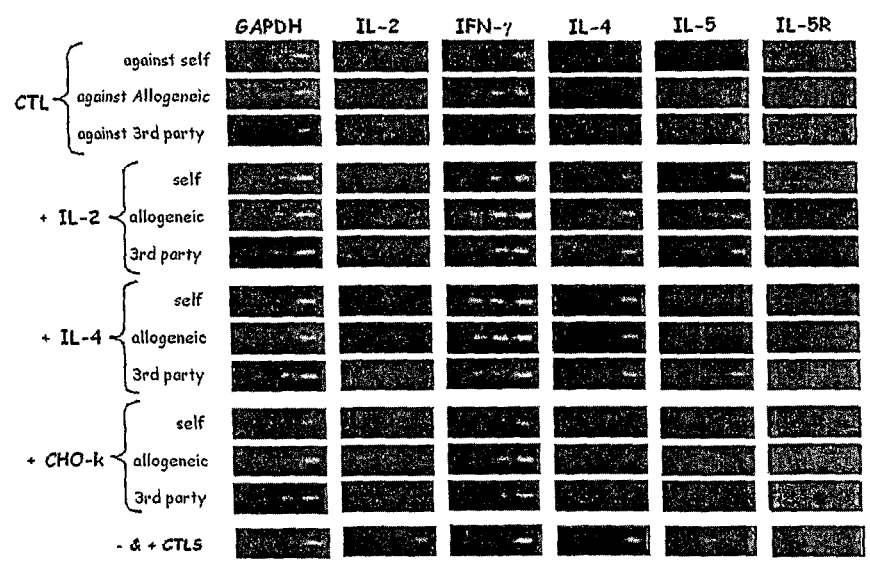
FIG. 4D shows the results of semi-quantitative RT-PCR using primers to cytokines or cytokine receptors (as indicated) on mRNA isolated from CD4$^+$,CD25$^+$ T cells from DA rats tolerant to PVG allografts cultured in the presence of self antigen (from DA rats), donor antigen (from PVG rats) or third party antigen (from Lewis rats) in the presence of IL-2 or IL-4.
Figure 4D:
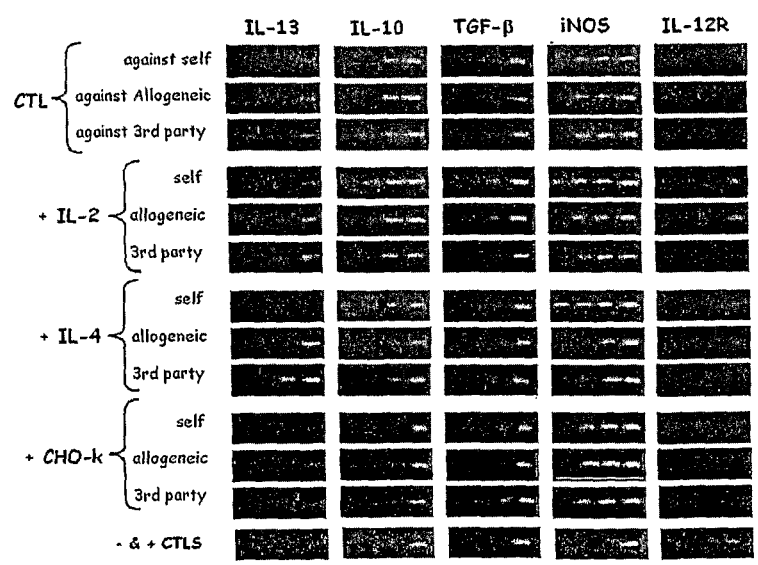

FIG. 4D illustrates cytokine and cytokine receptor induction in cultured tolerant CD4+,CD25+ T cells. This compares tolerant cells stimulated by specific donor, third party stimulators or self stimulators. Cultures contained no cytokine supplement (CTL top three lines) or were supplemented with IL-2, IL-4 or CHO—k supernatant. −&+CTLS were cDNA from ConA activated T cells was used as a control for the assay itself (−&+controls). mRNA was assayed using semi-quantitative RT-PCR with serial dilutions of cDNA from right to left.

There was no induction of IL-2 mRNA in any CD4+, CD25+ T cells preparation. The most consistent and abundant mRNA was for IFN-γ that was detected in all assays and tended to be enhanced after culture of CD4+,CD25+ T cells with either IL-2 or IL-4. IL-12Rβ2 was induced in CD4+, CD25+ T cells cultured with IL-2 and to a lesser extent with IL-4, and was not observed in CD4+,CD25+ T cells cultured with no cytokines. IFN-γ mRNA was induced in cells cultured with IL-4. mRNA for IL-4 and IL-5 was only mainly induced in CD4+,CD25+ T cells exposed to IL-2 or IL-4 and in neither control culture with no cytokines or CHO—k supernatant. IL-13 mRNA was detected in all samples with some induction with IL-2 and IL-4, but this may in part reflect differences in starting cDNA as per GAPDH levels. mRNA for IL-10 and TGF-β were present in all cultures and were not discriminatory. mRNA for IL-5Rα was induced in CD4+,CD25+ T cells exposed to IL-4 as indicated by very faint bands. Samples assayed at day 4 show a more definite expression of IL-5Rα mRNA in cells cultured with IL-4 mRNA. See FIG. 4E.

This suggests a different population of T suppressor cells may be induced with IL-2 and with IL-4, the IL-2 inducing cells that might respond to Th1 cytokines and IL-4 ones that might respond to Th2 cytokines such as IL-5.

FIG. 4E

Figure 4E:
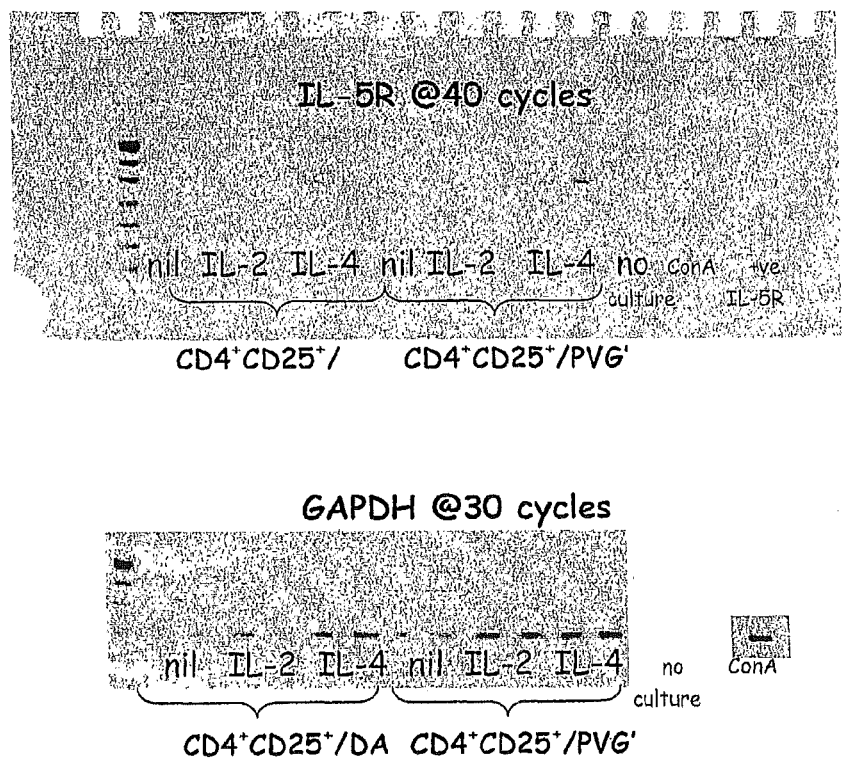
FIG. 4E shows the results of semi-quantitative RT-PCR using primers to the IL-5 receptor alpha chain or to GADPH on mRNA isolated from naïve CD4$^+$,CD25$^+$ T cells incubated in the presence of either self stimulators or PVG stimulators, alone or with either IL-2 or IL-4.

FIG. 4E shows the IL-5-Rα chain is induced in CD4+, CD25+ T cells cultured with IL-4. In this study naïve CD4+, CD25+ T cells from DA rats were cultured with either self DA stimulators or PVG stimulators for 4 days. IL-5Rα mRNA was assayed in cDNA collected from cells. Cells were cultured with nil cytokine, IL-2 or IL-4. IL-5Rα mRNA was only detected in cells cultured with IL-4 with greater levels in those cultured with alloantigen than those cultured with self antigen. Controls were uncultured CD4+,CD25+ T cells, cDNA from ConA activated lymphocytes and a known cDNA which had IL-5Rα.

FIG. 4F

Figure 4F:
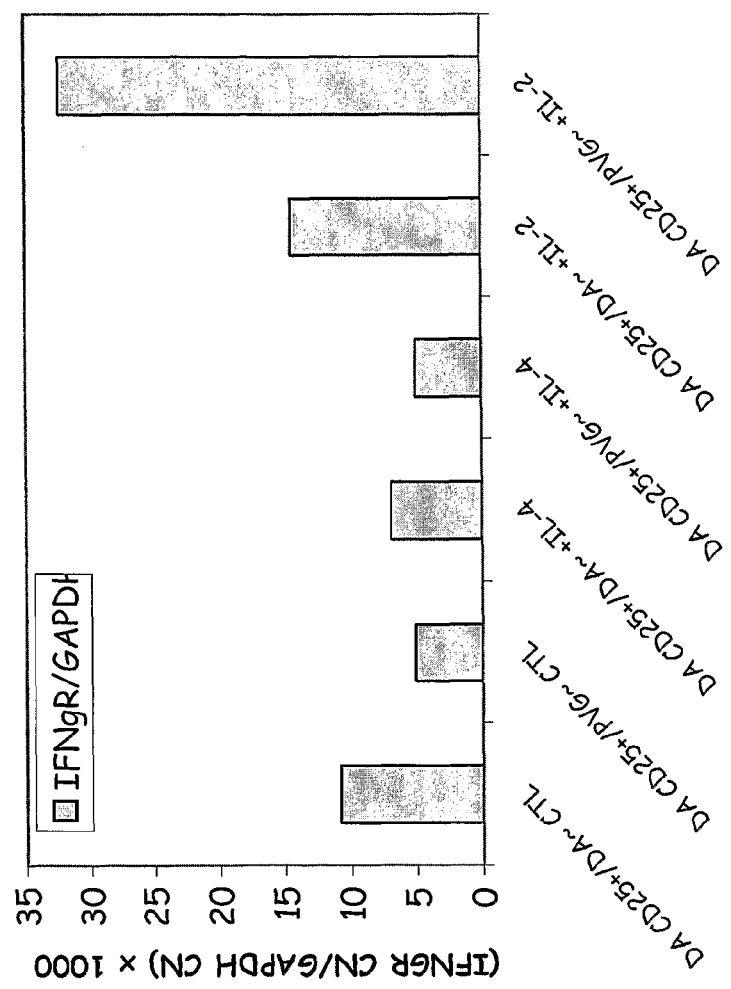
FIG. 4F is a graph showing the results of real-time RT-PCR using primers to the IFN-γ receptor or to GADPH on mRNA isolated from naïve CD4$^+$,CD25$^+$ T cells incubated in the presence of self or alloantigen, and with no cytokine or with either IL-2 or IL-4.

FIG. 4F shows real time RT-PCR for IFN-γ receptor (IFNGR) on CD4+,CD25+ T cells contacted with antigen in the presence of IL-2.

This study clearly demonstrated that there was induction of IFN-γ receptor on CD4+,CD25+ T cells cultured with IL-2 and alloantigeneic PVG stimulators and to a lesser degree with self DA stimulators, and not in cells cultured with no cytokines.

Taken together, these studies in FIGS. 4A, 4B and 4C show that CD4+,CD25+ T cells exposed and activated with Th1 responses (ie IL-2) and alloantigen, developed receptors that would allow them to respond to Th1 cytokines such as IFN-γ and IL-12. On the other hand, CD4+,CD25+ T cells exposed and activated by Th2 cells (ie IL-4) in the presence of alloantigen develop receptors for Th2 cytokines such as IL-5. They also express the Th1 cytokine IFN-γ mRNA. These results are consistent with our observation that activated CD4+,CD25+ T cells from rats with tolerance to PVG proliferate to PVG but not self or third party when either IFN-γ or IL-5 are added to the culture, but not if there is no cytokines.

The inventors propose that under normal circumstances of an immune response, with early activation there would be both IL-2 and IL-4 resulting in activation of both types of CD4+,CD25+ T cells.

The inventors propose to call these two types of activated CD4+,CD25+ T cells Ts1 cells and Ts2 cells. Ts1 cells are CD4+,CD25+ T cells activated by IL-2 that acquire responsiveness to IFN-γ and/or IL-12p70 and Ts2 cells that are CD4+,CD25+ T cells activated by IL-4 that acquire responsiveness to IL-5. Ts refers to suppressor T cells of the CD4+, CD25+ T cell phenotype.

Conclusions

IL-2 and IL-4 have different effects on CD4+,CD25+ T cells in culture, including;
a) Whilst both stimulate proliferation to self and alloantigen, the response to IL-4 peaks and tapers earlier than that with IL-2.
b) Culture with IL-2 leads to development of a CD4+,CD8+ double positive CD25+ T cells. This development of double positive cells is probably de-differentiation of CD4+,CD25+ T cells to re-express CD8.
c) Neither culture with IL-2 or IL-4 induces detectable expression of IL-2 mRNA, but both IL-2 and IL-4 induce mRNA for IL-4, IL-5, IL-12p40, IFN-γ, iNOS. There appears to be no detectable specific induction of IL-10, IL-13 and TGF-β.
d) There is late expression of new cytokine receptors, with IFN-γR appearing when cultured with IL-2 and antigen. IL-5R appears with IL-4. IL-12Rβ2 appears with both stimuli but possibly more with IL-2 than IL-4.
e) The pattern of cytokine mRNA expression with tolerant cells cultured with IL-2 or IL-4 is similar to that with naïve CD4+,CD25+ T cells, consistent with this being polyclonal activation of CD4+,CD25+ T cells, not activation of alloantigen specific CD4+,CD25+ T cells.
f) That IL-2 induces an IFN-γ/IL-12p70 dependent suppressor cell, that we propose to ascribe the name Ts1.
g) That IL-4 induces an IL-5 dependent suppressor cell, that we wish to ascribe the name Ts2.

Example 5

This study examines the effect of naïve CD4+,CD25+ T cells on CD4+,CD25− T cells.

FIG. 5A

Figure 5A:
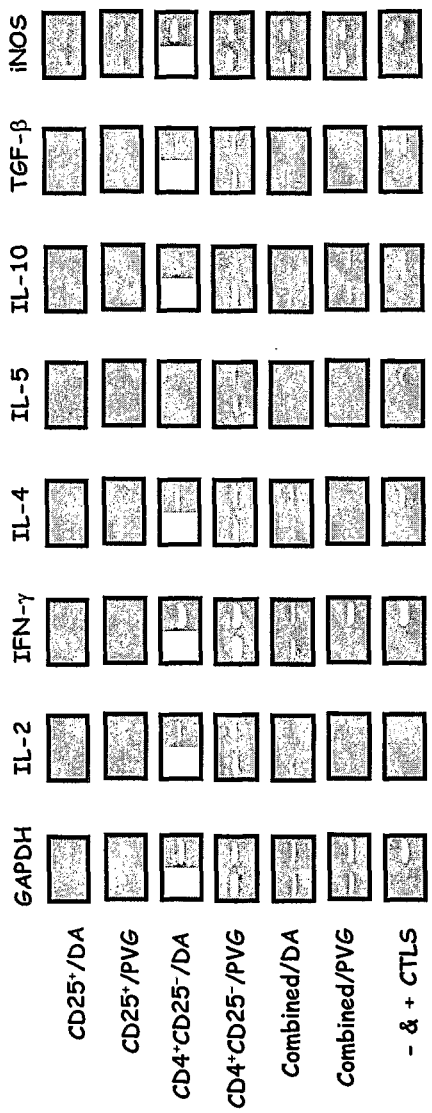
FIG. 5A shows the results of semi-quantitative RT-PCR using primers to cytokine mRNA isolated from CD4$^+$,CD25$^+$ T cells and CD4$^+$CD25$^-$ T cells alone or admixed in a 1:1 ratio. All populations were from naïve DA rats and were incubated in the presence of self or alloantigen.

FIG. 5A shows the result of RT-PCR analysis of expression of GAPDH, IL-2, IFN-γ, IL-4, IL-5, IL-10, TGF-β and iNOS mRNA following contact of CD4+,CD25+ T cells, CD4+, CD25− T cells, and combined CD4+,CD25− T cells and CD4+,CD25− T cells from DA rats, with DA or PVG antigen. In this assay duplicate samples at maximum concentration of cDNA were examined as there is limited mRNA extracted from these cultures. CD4+,CD25+ T cells alone cultured with self (DA) stimulators, have minimal cytokine induction. With PVG stimulators there is no IL-2 mRNA but some IFN-γ, IL-4, IL-10 and TGF-β expression. In contrast the CD4+, CD25− T cells have marked induction of all cytokine mRNA tested when stimulated by PVG, and this profile is similar to that observed when stimulated with DA antigen. With self-stimulators there is no IL-5 mRNA induction, however. It should be noted that the CD4$^+$,CD25$^-$ T cells have a marked proliferative response to self, known as the autologous MLC, and thus marked induction of cytokine mRNA in the CD4$^+$, CD25$^-$ T cells responding to self is consistent with a marked autologous proliferative response.

In the mixing experiment of CD4$^+$,CD25$^-$ T cells and naïve CD4$^+$,CD25$^+$ T cells at a 1:1 ratio there is total suppression of proliferation as described before. In these cultures there is marked reduction in expression of IL-2, IL-4 and IL-5 mRNA in the allogeneic response compared to that with the CD4$^+$, CD25$^-$ T cells. There was a small reduction in IFN-γ, IL-10, TGF-β mRNA and no effect on iNOS mRNA levels compared to those observed with CD4$^+$,CD25$^-$ T cells alone against PVG. CTL are assays with cDNA from ConA stimulated T cells.

These results show that the suppression of MLC by the CD4$^+$,CD25$^+$ T cells is associated with IFN-γ and iNOS induction, suggesting NO production may mediate this effect of suppression. This possibility was examined by adding an iNOS inhibitor L-NIL to MLC.

FIG. 5B

Figure 5B:
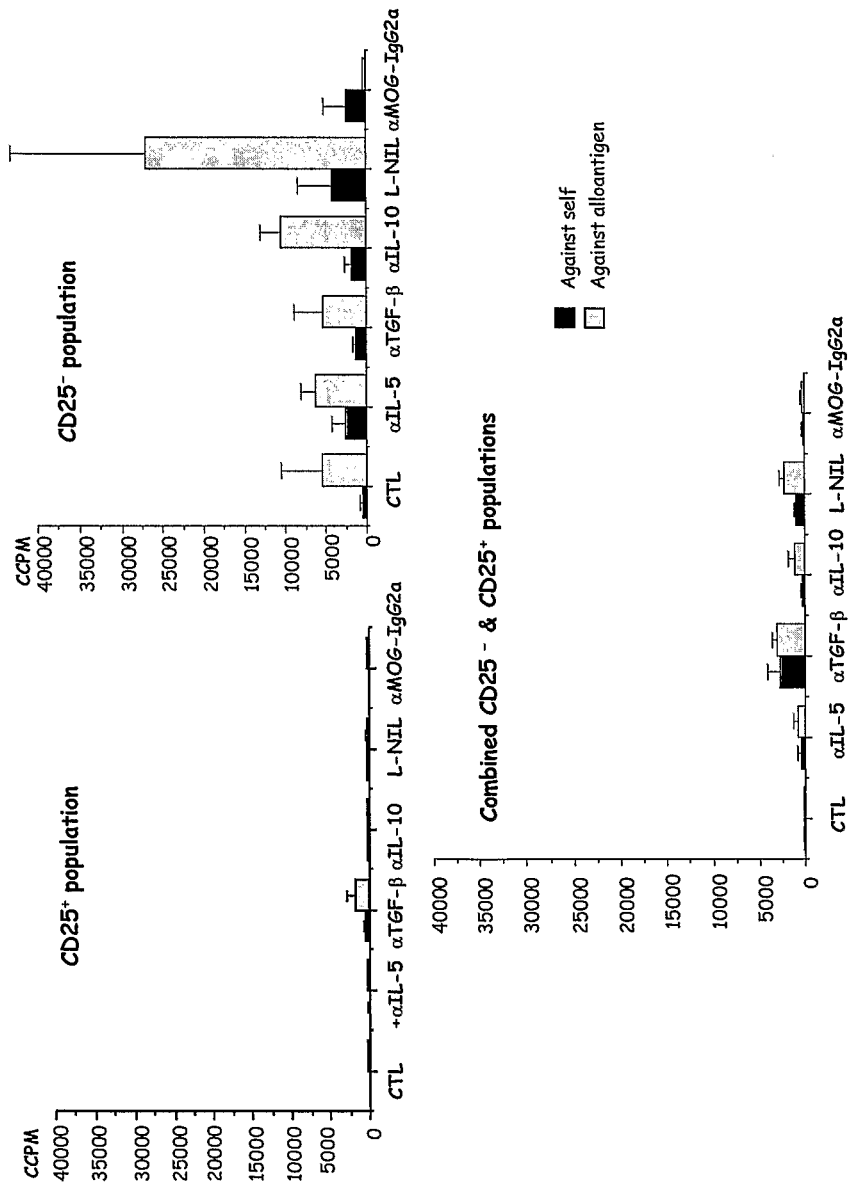

FIG. 5B is graphs showing the effect of blocking IL-5, TGF-β, IL-10 and iNOS on the inhibitory effects of CD4$^+$, CD25$^+$ T cells on CD4$^+$,CD25$^-$ T cells proliferation in MLC.

In this experiment it was examined if iNOS or monoclonal antibodies to IL-5, TGF-β and IL-10 could block the suppression of CD4$^+$,CD25$^+$ T cells on CD4$^+$,CD25$^-$ T cells proliferation when they are cultured in a ratio of 1:1. As can be seen in the bottom panel, the controls (CTN) are totally suppressed and enhanced proliferation occurs to fully allogeneic donor when iNOS, anti-IL-5, anti-TGF-β and anti-IL-10 monoclonal antibody is added but not with the control anti-Mog Ig2a monoclonal antibody. None restored proliferation to that of CD4$^+$,CD25$^-$ T cells alone (see top right panel) and the effect was not non-specific as neither iNOS nor the antibodies had an effect on the proliferation of CD4$^+$,CD25$^-$ T cells alone or on CD4$^+$,CD25$^+$ T cells alone, except for anti-TGF-β which did enhance CD4$^+$,CD25$^+$ T cells proliferation. These results suggest that IL-5, IL-10 and TGF-β have a functional effect in the suppressive effects of CD4$^+$,CD25$^+$ T cells on CD4$^+$,CD25$^-$ T cells in MLC. This suggests that the non-specific suppression of CD4$^+$,CD25$^+$ T cells may also be in part mediated through the effects of IL-5 and IFN-γ.

Conclusions

The suppressive effect of naïve CD4$^+$,CD25$^+$ T cells on naïve CD4$^+$, CD25$^-$ T cells in MLC is associated with:
  a) Naïve CD4$^+$,CD25$^+$ T cells when admixed 1:1 with naïve CD4$^+$,CD25$^-$ T cells totally suppress the MLC proliferation.
  b) A marked reduction in induction of IL-2, IL-4, IL-5 mRNA expression and a smaller reduction in induction of IFN-γ and TGF-β mRNA expression, but no reduction in iNOS induction when compared with the induction in CD4$^+$,CD25$^-$ T cells alone in MLC.
  c) Blocking with anti-IL-5 or anti-TGF-β or anti-IL-10 monoclonal antibodies partially blocks suppression suggesting IL-5, IL-10 and TGF-β have an effect in mediating the suppression by naïve CD4$^+$,CD25$^+$ T cells on CD4$^+$,CD25$^-$ T cells proliferation in MLC.

Example 6

The effect of IL-4 or IL-5 on survival in culture of CD4$^+$ T cells from DA rats with tolerance to PVG allografts was examined. The survival of tolerance mediating cells was assayed by their ability to adoptively transfer specific tolerance to PVG cardiac allografts and to retain the capacity to effect rejection of third party Lewis allografts.

These studies used CD4$^+$ T cells from spleen and lymph nodes of DA rats tolerant to a PVG cardiac allograft that has survived over 75 days. Graft acceptance and tolerance developed after a short course of immunosuppression at the time of transplantation, either 10 days of cyclosporine treatment, or anti-CD4 or anti-CD3 monoclonal antibody therapy, as described (Transplantation, 1997, 64, 1559-1567 and 1993, 55; 459-468). The ability of these cells to transfer tolerance was examined in the irradiated adoptive host that is described above in FIGS. 3A and 3B.

In early studies we had demonstrated that fresh tolerant cells transfer tolerance to specific donor (PVG) but reject third party grafts. Admixing tolerant cells with naïve CD4$^+$ T cells in a ratio of 4:1, ie 20 million tolerant CD4$^+$ T cells with 5 million naïve CD4$^+$ T cells is used to show the tolerant cells can suppress the naïve cells from effecting rejection. Previous studies and controls for these studies showed that the culture of tolerant CD4$^+$ T cells with specific donor stimulators in a mixed lymphocyte culture for 3 days, resulted in their loss of capacity to transfer tolerance. Culture of naïve cells under similar conditions resulted in cells that effected rejection.

When tolerant CD4$^+$ T cells were cultured with specific donor stimulators and with a cytokine rich media of ConA supernatant, then they retained their capacity to transfer tolerance to specific donor but retained the capacity to effect third party graft rejection as described (Transplantation 1993, 55, 374-379). This baseline data was reproduced as controls to the experiments and was as per the previous described results.

FIG. 6A

Figure 6A:
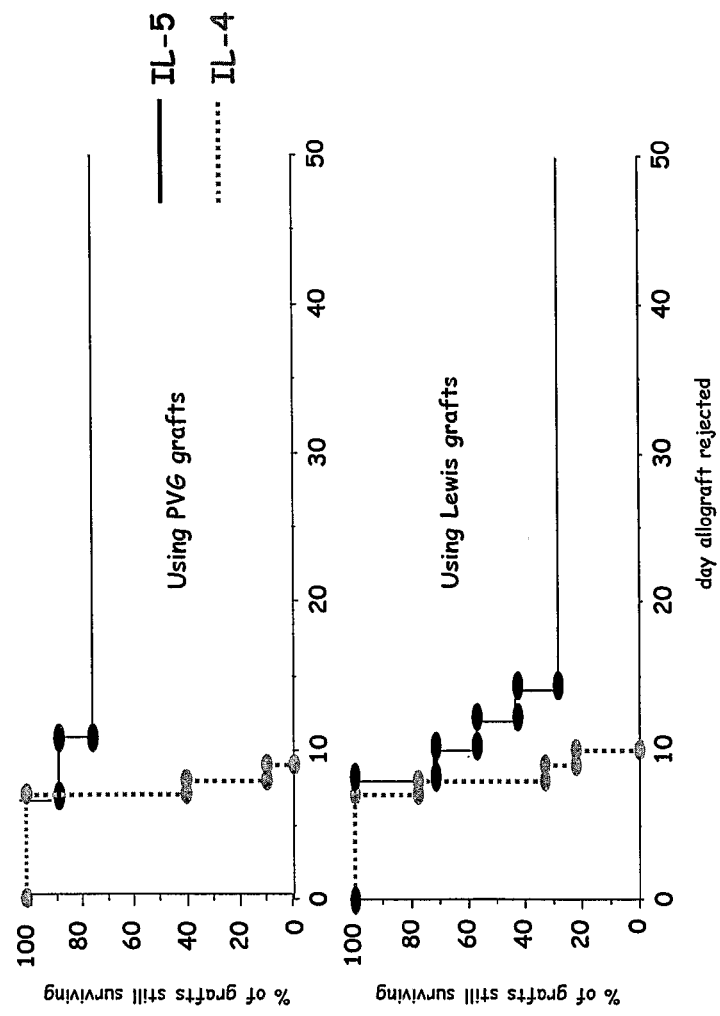
FIG. 6A is graphs showing the survival of heterotopic cardiac allografts transplanted from PVG rats or Lewis rats into irradiated DA rats that were adoptively restore with CD4$^+$ T cells from DA rats tolerant to a PVG heart allografts where the cells had been cultured for 3 days with PVG stimulator cells in media supplemented with either IL-4 (dotted line) or IL-5 (solid line).

FIG. 6A shows the proliferation of CD4$^+$ T cells from DA rats tolerant to a PVG heart allograft after being cultured with either IL-4 or IL-5 alone in MLC with PVG antigen and no ConA supernatant. This experiment demonstrated that IL-5 alone sustained the tolerance transferring specific suppressor CD4$^+$ T cells. The same cells retained the capacity to effect third party graft rejection, demonstrating that the IL-5 alone did not induce tolerance mediating cells. Neither IL-2 (Transplantation 1993, 55, 374-379) nor IL-4 (see data above) alone maintain these suppressor CD4$^+$ T cells in culture with specific antigen, while a Con A supernatant with all these cytokines maintains the specific suppressor function of CD4$^+$ T cells.

Taken together these experiments with culture of CD4$^+$ T cells from rats with allograft tolerance demonstrated that IL-5 alone can substitute for the ConA supernatant. Either IL-2 or IL-4 alone is insufficient to maintain the tolerance maintaining cells.

FIG. 6B

Figure 6B:
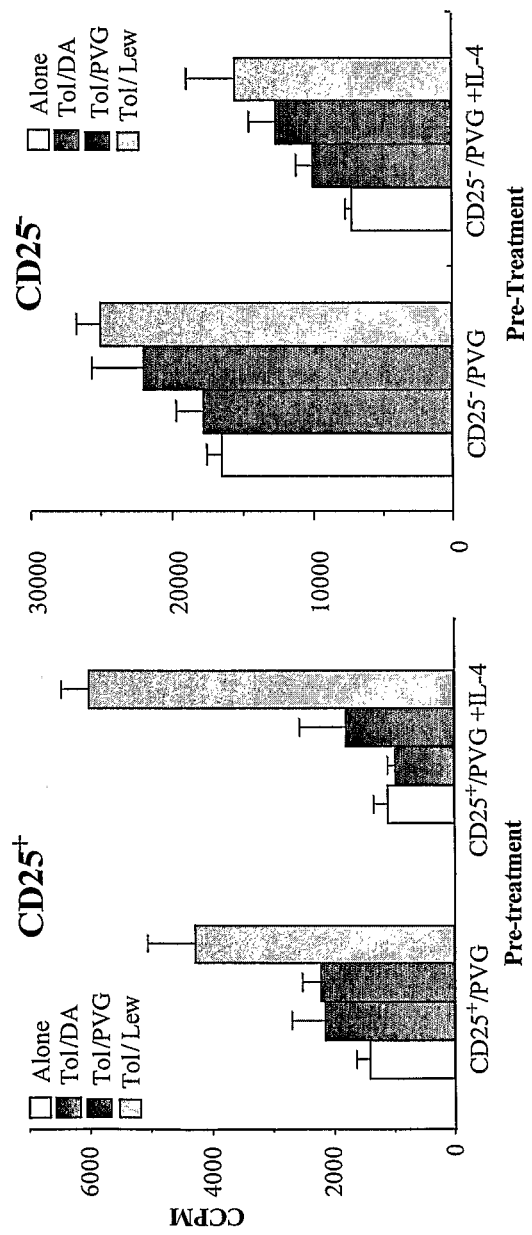
FIG. 6B are graphs showing the proliferation of CD4$^+$, CD25$^+$ T cells and CD4$^+$,CD25$^-$ T cells from DA rats tolerant to PVG allografts following incubating the lymphocytes with PVG antigen in the presence or absence of IL-4 (as indicated), followed by incubating the cells alone (white), or in the presence of self antigen (DA) (dark grey), donor antigen (PVG) (black) or third party antigen (Lewis) (light grey), and in the presence or absence of IL-4.

FIG. 6B illustrates the results of examination of the effect of culture in MLC with IL-4 and specific donor antigen on the capacity of tolerant CD4$^+$,CD25$^+$ T cells and CD4$^+$,CD25$^-$ T cells to proliferate in vitro when exposed to different stimulator cells.

CD4$^+$,CD25$^+$ T cells from DA rats tolerant to a PVG cardiac allograft were cultured against PVG (specific allogeneic) stimulator cells in a primary MLC with or without IL-4 for 3 days. These cells were subsequently washed, rested for 24 hours and then cultured in a secondary MLC alone or against DA (syngeneic), PVG (specific allogeneic) or Lewis (3rd party allogeneic) stimulator cells. Proliferation was assessed at day 2-3 of secondary culture.

The tolerant CD4$^+$,CD25$^+$ T cells have significantly reduced proliferation against specific donor PVG whether or not IL-4 is added to the primary MLC. The CD4$^+$,CD25$^-$ T cells had a similar response to donor and third party stimulators. These data are consistent with the findings in the adoptive transfer assay where IL-4 did not maintain the suppressor effect of unfractionated CD4+ T cells, suggesting the specifically tolerant CD4+,CD25+ T cells die in culture if IL-4 is the only cytokine available. Also that the CD4+,CD25− T cells cultured with IL-4 survive and maintain alloreactivity to specific donor and third party. These results are consistent with the adoptive transfer studies described in FIG. 6A where tolerant cells cultured with IL-4 do not maintain their ability to transfer specific tolerance. This study also demonstrates that the culture of specific CD4+,CD25− T cells from tolerant animals cannot be maintained by IL-4 and IL-4 does not reinduce tolerance. That is activated CD4+,CD25+ T cells from tolerant animals are not maintained or expanded by the IL-4 and alloantigen.

Conclusion

The Th2 cytokine IL-5 but not IL-4, promotes the survival of specific CD4+,CD25+ T cells tolerance mediating suppressor cells in culture and allows them to retain the ability to transfer tolerance.
a) Survival of the alloantigen specific tolerance mediating cells in CD4+ T cells in MLC can be supported by IL-5 or Con A sup. IL-4 supplement alone does not promote survival of the tolerance mediating CD4+ T cells.
b) The failure of tolerant CD4+,CD25+ T cells to proliferate to specific donor in MLC is not restored by pre-culture with specific donor alloantigen and IL-4.

Example 7

This study examined the effect of various cytokines on proliferation of activated CD4+,CD25+ T cells in MLC.

FIG. 7

Figure 7:
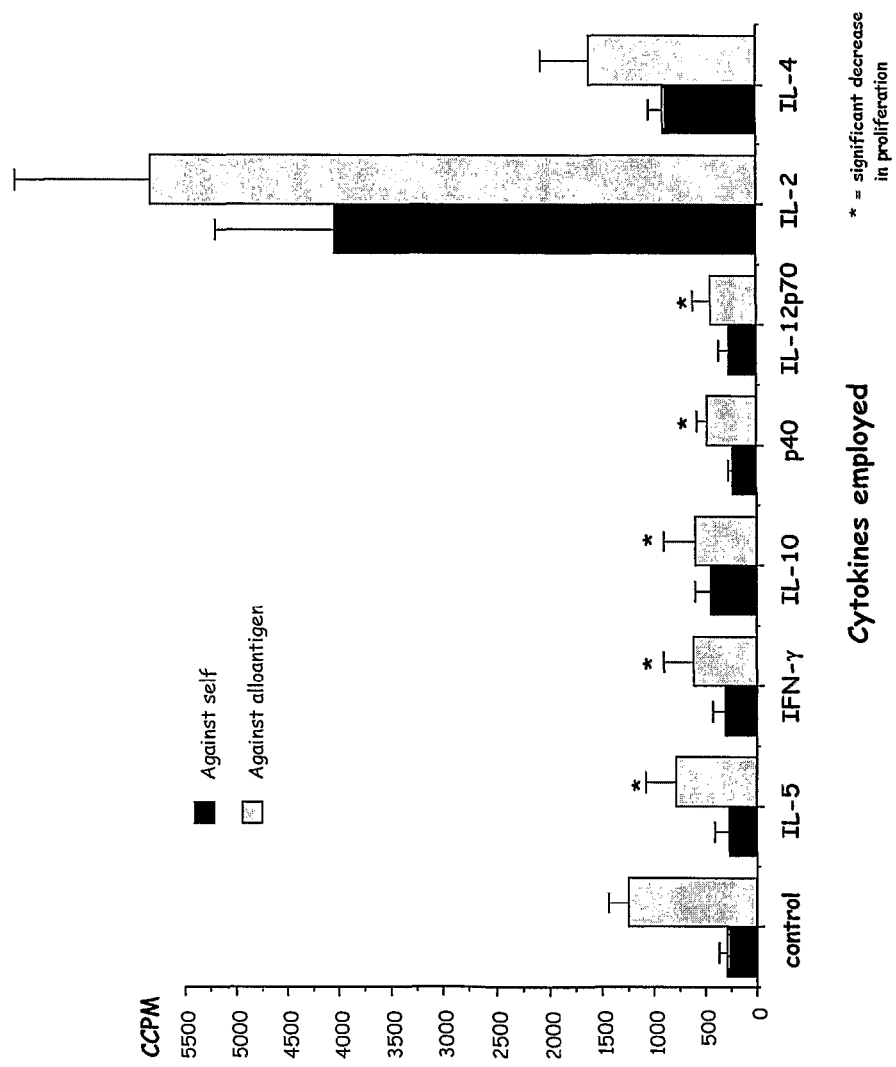
FIG. 7 is a graph showing the proliferation of unfractionated naïve lymphocytes from DA rats tolerant to PVG allografts at day 4 following contact with self-antigen or alloantigen in the presence of cytokines as indicated.

FIG. 7 examines the effect of individual cytokines on proliferation in MLC of unfractionated lymphocytes from DA rats with tolerance to PVG heart allografts.

In this experiment the effects of various cytokines on proliferation of unfractionated lymphocytes from DA rats with tolerance to a PVG allograft were examined MLC. The proposal was that key cytokines would promote survival of the activated CD4+,CD25+ T cells that maintain tolerance and these would inhibit the proliferative response of unfractionated cells in MLC.

This figure shows IL-2 and IL-4 markedly enhance proliferation to self DA and to specific-donor PVG. Both IL-5 and IFN-γ inhibit responses to PVG but not self. Other cytokines had a similar effect, including IL-10, IL-12p40 homodimer, and IL-12p70.

This data suggests the test for the tolerant state may be detected by adding IL-5, IL-12 or IFN-γ. These cytokines may inhibit proliferation of unfractionated tolerant lymphocytes by promoting the survival and function of the donor antigen specific activated CD4+,CD25+ T cells so they suppress the proliferative response in MLC. This effect may be detected by decreased proliferation or by other means that detect active function of the activated CD4+,CD25+ T cells.

Conclusion

Addition of cytokines that promote the survival of activated CD4+,CD25+ T cells from tolerant animals reduces the proliferation of unfractionated peripheral lymphocytes to specific donor antigen in MLC, in particular IL-5, IFN-γ and IL-12.

Example 8

This study examined the ability to treat EAN in rats by administering activated CD4+,CD25+ T cells.

Methods

Methods; EAN was induced in 10-15 week old female Lewis rats by immunization with bovine peripheral nerve myelin in Freund's complete adjuvant, as described (J. Neurol. Sci. 1994, 123: 162-172). The animals were monitored for disease activity daily by weighing and clinical observation and scoring of paralysis using a semi-quantitative score. The score used was; 5+ death or total paralysis requiring euthanasia, 4+ paralysis of all limbs, 3+ Total hind limb paralysis, and weak forearms, 2+ weak hind limbs, 1+ weak tails, 0 normal.

Results

FIG. 8

Figure 8A:
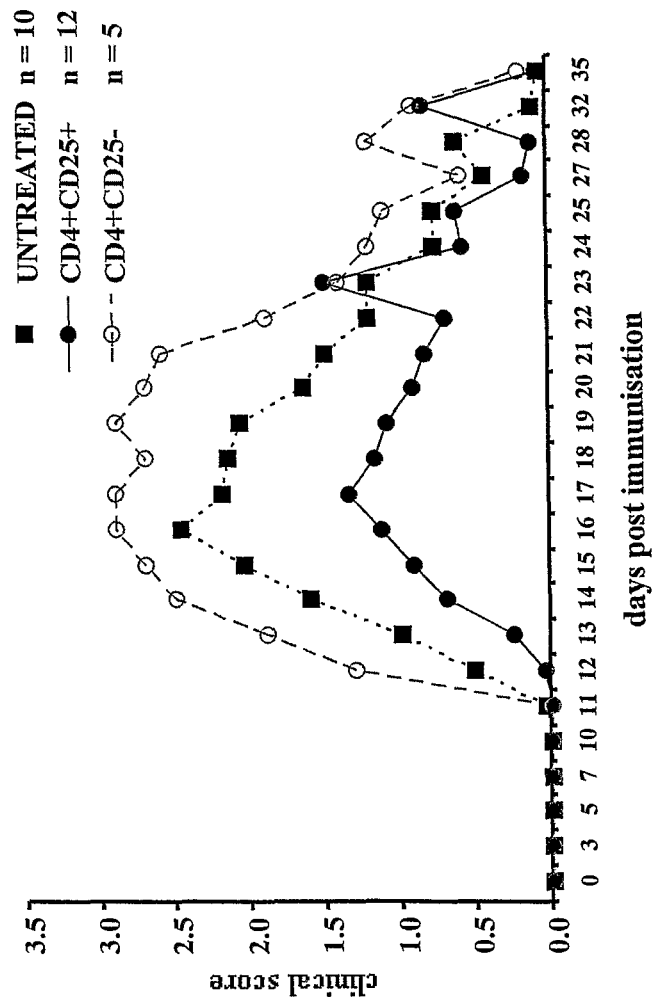
FIG. 8A is a graph showing the clinical time course of Experimental Allergic Neuritis (EAN) in Lewis rats following administration of lymphocytes from tolerant (recovered) Lewis rats. Closed squares are untreated rats, closed circles are rats treated with CD4$^+$,CD25$^+$ T cells from rats tolerant to EAN and open circles are rats treated with CD4$^+$,CD25$^-$ T cells from rats tolerant to EAN.
Figure 8B:
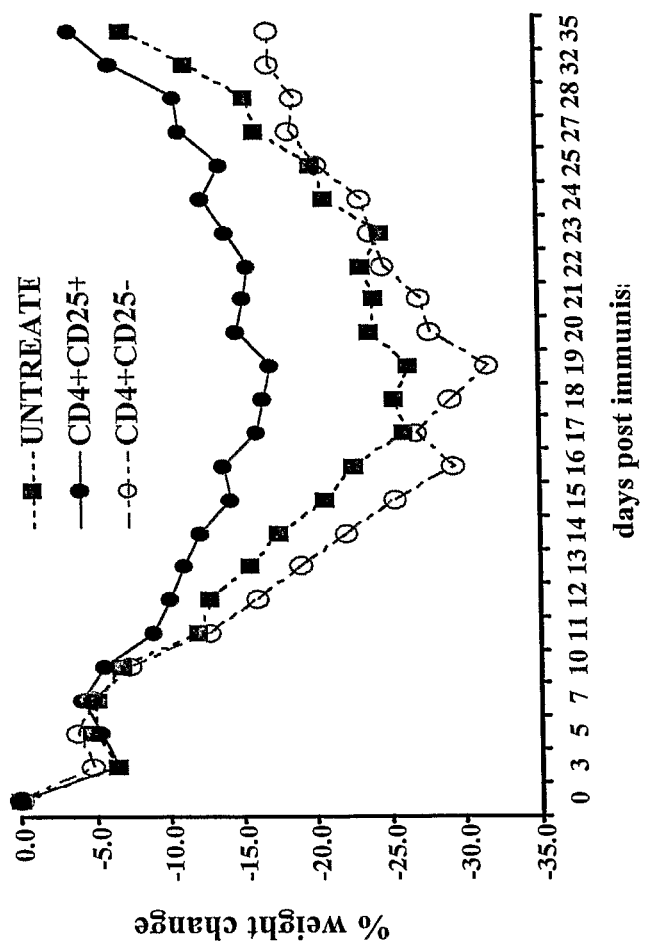
FIG. 8B is a graph showing the weight change over a time course of Experimental Allergic Neuritis (EAN) in Lewis rats following administration of lymphocytes from tolerant (recovered) Lewis rats. Closed squares are untreated rats, closed circles are rats treated with CD4$^+$,CD25$^+$ T cells and open circles are rats treated with CD4$^+$,CD25$^-$ T cells.

In FIGS. 8A and 8B, the effect of adoptive transfer of activated CD4+,CD25+ T cells or CD4+,CD25− T cells on the clinical course of Experimental Allergic Neuritis (EAN) in Lewis rats was examined.

As proof of concept, the effect of CD4+,CD25+ T cells from Lewis rats that had recovered from EAN on the development of EAN in naïve rats was examined by adoptive transfer of these cells to naïve Lewis rats at the time of their immunization with PNM in Freund's complete adjuvant. The effect of these tolerant CD4+,CD25+ T cells was compared to the effect of CD4+,CD25− T cells from these tolerant animals.

In this model rats that recover, appear normal and are resistant to re-induction of EAN by re-immunization with immunogenic antigen. That is they are considered tolerant after their original disease, thus rats that had just recovered from EAN were considered a good source of activated tolerant CD4+,CD25+ T cells. Lewis rats that had recovered from EAN at 30 days post immunization were thus used to prepare CD4+,CD25− T cells and CD25+,CD4+ T cells. All groups of Lewis rats (n=5-12) were immunized with peripheral nerve myelin (PNM) and Freund's adjuvant. One group was given 5 million CD25+,CD4+ T cells ivi and another group was given 5 million CD4+,CD25− T cells ivi. The control group was not given any cells at the time of immunization. Those given activated CD4+,CD25+ T cells from tolerant rats had a much milder clinical course with a maximum disease score just over one, compared to controls whose diseases peaked at 2.5+ around 15-16 days post immunization. Rats given CD4+,CD25− T cells from tolerant animals developed more severe disease peaking at 3+ and with an earlier onset and slower recovery.

In another experiment naïve CD4+,CD25+ T cells were given on day 0 of immunization. These had no effect on the clinical course of EAN confirming this was an effect of activated CD4+,CD25+ T cells from a tolerant animal.

Weight loss was much less in those given activated CD4+,CD25+ T cells from a tolerant animal and slightly greater in those given CD4+,CD25− T cells from a tolerant animal than controls given no cells. (FIG. 8B)

As adult rats have 500-1000 million peripheral lymphocytes, we suggest that 5 million CD4+,CD25+ T cells would not have had a significant impact of the CD25+,CD4+ T cell: CD4+,CD25− T cell ratio in these naïve hosts. This is further supported by the finding that giving 5 million naïve CD4+,CD25+ T cells had no effect on the course of EAN. Thus the effect was most likely due specifically to the specifically activated CD4+,CD25+ T suppressor cell effect, not the well described non-specific effect of naïve CD4+,CD25+ T cells.

This suggests a finite number of activated CD4+,CD25+ T cells may significantly alter the disease course and re-establish tolerance, during an acute disease process.

Conclusions

Specific activated CD4$^+$,CD25$^+$ T cells from animals that have recovered from acute autoimmune diseases can ameliorate the severity of autoimmune disease.

We propose that autologous CD4$^+$,CD25$^+$ T cells may be obtained from diseased animals in remission and further activated to transfer back to maintain or re-establish tolerance.

Example 9

Cell subsets and cultures were as per the mixed lymphocyte cultures. Antigen presenting cells with PNM were prepared by pre-culturing for 1 hours at 37 degrees with PNM and the autologous stimulator cell preparation. These cells were then washed. Culture conditions and measurement of proliferation was as described for MLC.

Results

These studies demonstrate distinct patterns of response of CD4$^+$,CD25$^+$ T cells to an autoantigen before and during exposure to the autoantigen, which in this case was PNM in the EAN model.

First the response of naïve CD4$^+$ T cells, CD4$^+$,CD25$^+$ T cells and CD4$^+$,CD25$^-$ T cells, showed that the CD4$^+$,CD25$^-$ T cells had a much greater response than the CD4$^+$ T cells, and that the response of CD4$^+$,CD25$^-$ T cells could be inhibited by naïve CD4$^+$,CD25$^+$ T cells. Naïve CD4$^+$,CD25$^+$ T cells alone had little or no response to PNM. This was similar to the ability of naïve CD4$^+$,CD25$^+$ T cells to inhibit naïve CD4$^+$,CD25$^-$ T cells in MLC. (FIG. 9A)

Second in animals that are just recovering there is an active suppressor phenotype, where the CD4$^+$,CD25$^+$ T cells do not greatly respond to specific antigen and cannot fully inhibit the response of CD4$^+$,CD25$^-$ T cells to the specific antigen. We would predict that these cells may respond to IL-5, IFN-γ and possibly IL-12. (FIG. 9B)

FIG. 9A.

Figure 9A:
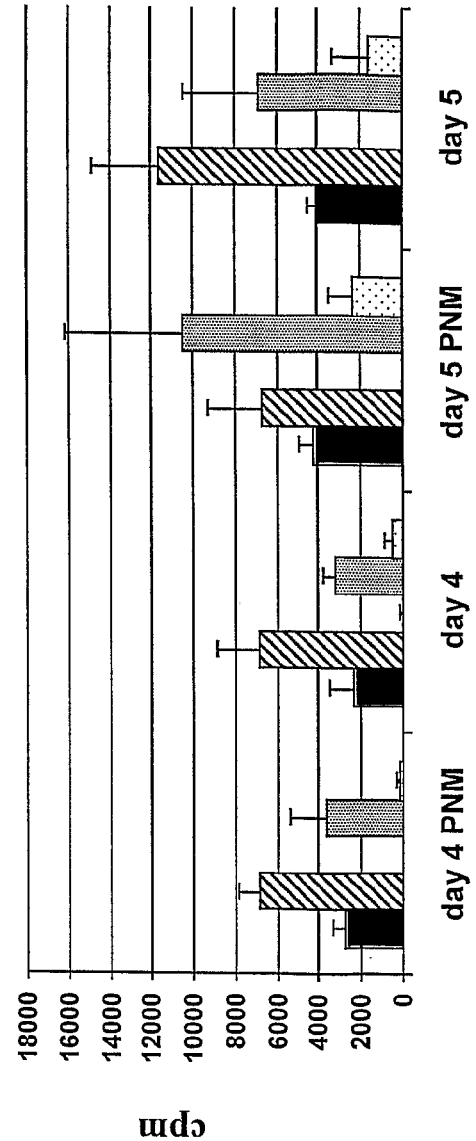
FIG. 9A is a graph showing the proliferation of various combinations of lymphocytes (as indicated) from naïve Lewis rats in response to PNM.
Figure 9B:
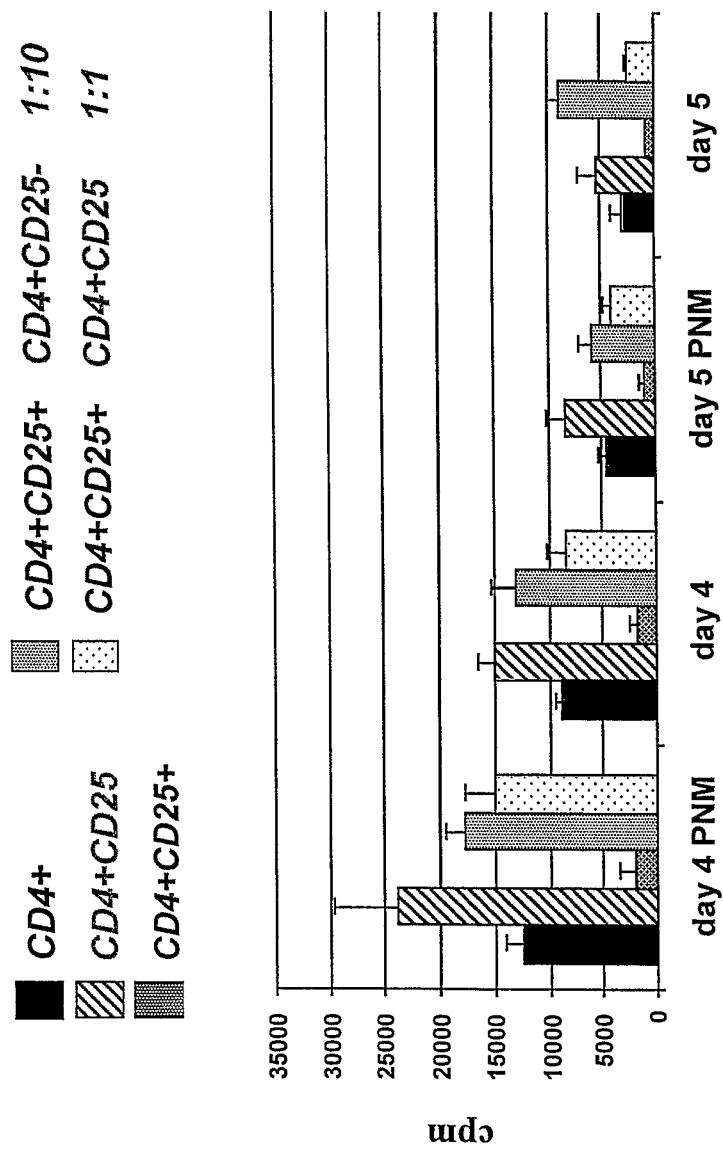
FIG. 9B is a graph showing the proliferation of various combinations of lymphocytes (as indicated) from Lewis rats tolerant to PNM antigen (recovered from the EAN 4 weeks after immunisation) in response to PNM antigen.

Referring to FIG. 9A, proliferation of lymphocytes from naïve Lewis rats when stimulated in culture with self-antigen presenting cells with and without PNM was examined. Proliferation at day 4 vs day 5.

The proliferation of naïve CD4$^+$,CD25$^+$ T cells and CD4$^+$,CD25$^-$ T cells to that of naïve unfractionated CD4$^+$ T cells was examined. This response is similar to that observed with naïve cells response to alloantigens in MLC. At day 4 the response of unfractionated CD4$^+$ T cells was similar to self and self plus PNM. That of CD4$^+$,CD25$^-$ T cells was greater than unfractionated CD4$^+$ T cells, consistent with removal of the non-specific suppression by naïve CD4$^+$,CD25$^+$ T cells. Again there was no difference in the response to self alone and self plus PNM. CD4$^+$,CD25$^+$ T cells had minimal proliferation alone, and when admixed with CD4$^+$,CD25$^-$ T cells in a normal ratio, suppressed the response to that of unfractionated CD4$^+$ T cells. With a ratio of 1:1 naïve CD4$^+$,CD25$^+$ T cells: naïve CD4$^+$,CD25$^-$ T cells there was near total suppression.

The results on day 5 had an essentially similar pattern but there was greater proliferation than on day 4. Again admixing the two populations at 1:1 ratio markedly suppressed the response to both self alone and self with PNM.

FIG. 9B

Referring to FIG. 9B, in this study T cell subsets were prepared from Lewis rats that had recovered from EAN, 30 days after immunization. Again culture stimulated with self antigen presenting cells alone or primed with PNM were set up and proliferation assayed at days 4 and 5. The response of unfractionated CD4$^+$ T cells and CD4$^+$,CD25$^-$ T cells was greater to PNM than to self-antigen presenting cells, consistent with a specific sensitisation. The CD4$^+$,CD25$^+$ T cells alone had a non-specific proliferation above that normally seen with naïve CD4$^+$,CD25$^+$ T cells. This may be due to polyclonal activation of the CD4$^+$,CD25$^+$ T cells.

The major difference was that the suppression with CD25$^+$, CD4$^+$ T cells at 1:1 against PNM was incomplete, whilst that to self was more complete.

Our interpretation of the results of this assay is that there are two responses, that to self-antigens and that to PNM. The data is consistent with partial suppression of the anti-self response but failure to suppress that anti-PNM response. These data are similar to that observed in transplant tolerance in that the activated CD4$^+$,CD25$^+$ T cells which have alloantigen specificity do not suppress the response to the specific antigen, but retain their capacity to non-specifically inhibit a third party response.

Conclusions

That CD4$^+$,CD25$^+$ T cells from naïve animals behave in autoimmune responses like they behave with alloimmune responses.

a) That in naïve animals there is no specific response to autoantigen, in that they are the same as that to self stimulators.
b) That in naïve animals removal of CD4$^+$,CD25$^+$ T cells enhances the response to self stimulators. That is naïve CD4$^+$,CD25$^-$ T cells proliferation is greater than that of unfractionated CD4$^+$ T cells.
c) Further naïve CD4$^+$,CD25$^-$ T cells proliferation can be suppressed by admixing with CD4$^+$,CD25$^+$ T cells, especially at a 1:1 ratio.
d) That in animals recovering from acute episode of autoimmunity, there is an enhanced response to specific antigen compared to self antigens, for CD4$^+$ T cells and CD4$^+$,CD25$^-$ T cells, but no specific response by CD4$^+$, CD25$^+$ T cells to the autoantigen. These CD4$^+$, CD25$^+$ T cells do not fully suppress the CD4$^+$,CD25$^-$ T cells proliferation, and are more effective against the self response than against the specific alloantigen. That is the activated specific CD4$^+$,CD25$^+$ T cells do not suppress in vitro.

Example 10

This example illustrates the ability of CD4$^+$,CD25$^+$ T cells cultured in vitro in the presence of donor antigen and IL-2 or IL-4 to suppress donor heart graft rejection.

Ts1 cells (activated CD4$^+$,CD25$^+$ T cells produced by alloantigen stimulation in the presence of IL-2, expressing IFNGR and IL-12Rβ2) and Ts2 cells (activated CD4$^+$,CD25$^+$ T cells produced by alloantigen stimulation in the presence of IL-4, expressing IL-5Rα and IFN-γ) were produced by 3 day culture of naïve CD4$^+$,CD25$^+$ T cells from DA rats in the presence of antigen presenting cells from PVG rats and >100 units/ml of IL-2 or IL-4 respectively. These cells were then tested for their capacity to prevent PVG or third party cardiac allograft rejection in irradiated DA rats restored with 5×10$^6$ naïve CD4$^+$ T cells. The results of the experiment are shown in Table 2.

As can be seen from Table 2, naïve CD4$^+$,CD25$^+$ T cells in a ratio of 1:10 with naïve CD4$^+$ T cells did not suppress rejection of hearts from PVG donor strains. Similarly, CD4$^+$, CD25$^+$ T cells contacted with PVG antigen in the presence of IL-2 or IL-4 and mixed in a ratio of 1:10 with CD4$^+$ T cells did not suppress rejection of hearts from Lewis donor strains. In contrast, CD4$^+$,CD25$^+$ T cells contacted with PVG antigen and incubated in the presence of IL-2 or IL-4 and mixed in a ratio of 1:10 with naïve CD4$^+$ T cells did suppress rejection of hearts from PVG donor strains. Thus, both Ts1 and Ts2 cells at a ratio of 1:10 (TS1 or TS2 T cells to CD4+ T cells) prevented rejection of PVG but not Lewis allografts, demonstrating specificity of induction of suppression and enhanced suppression as naïve CD4+CD25+ T cells at ratio of 1:10 did not suppress. Naïve CD4+CD25+ T cells at a ratio of 1:1 suppressed both PVG and Lewis rejection. Thus a short culture with specific alloantigen and either IL-2 or IL-4 selected for and expanded specific suppressor CD4+CD25+ T cells leading to a 10-fold increase in suppressor capacity.

Thus, these results demonstrate that IFN-γ can preserve survival of activated CD4+,CD25+ T cells in a CD4+ T cell population from tolerant animals.

Example 12

Figure 11:
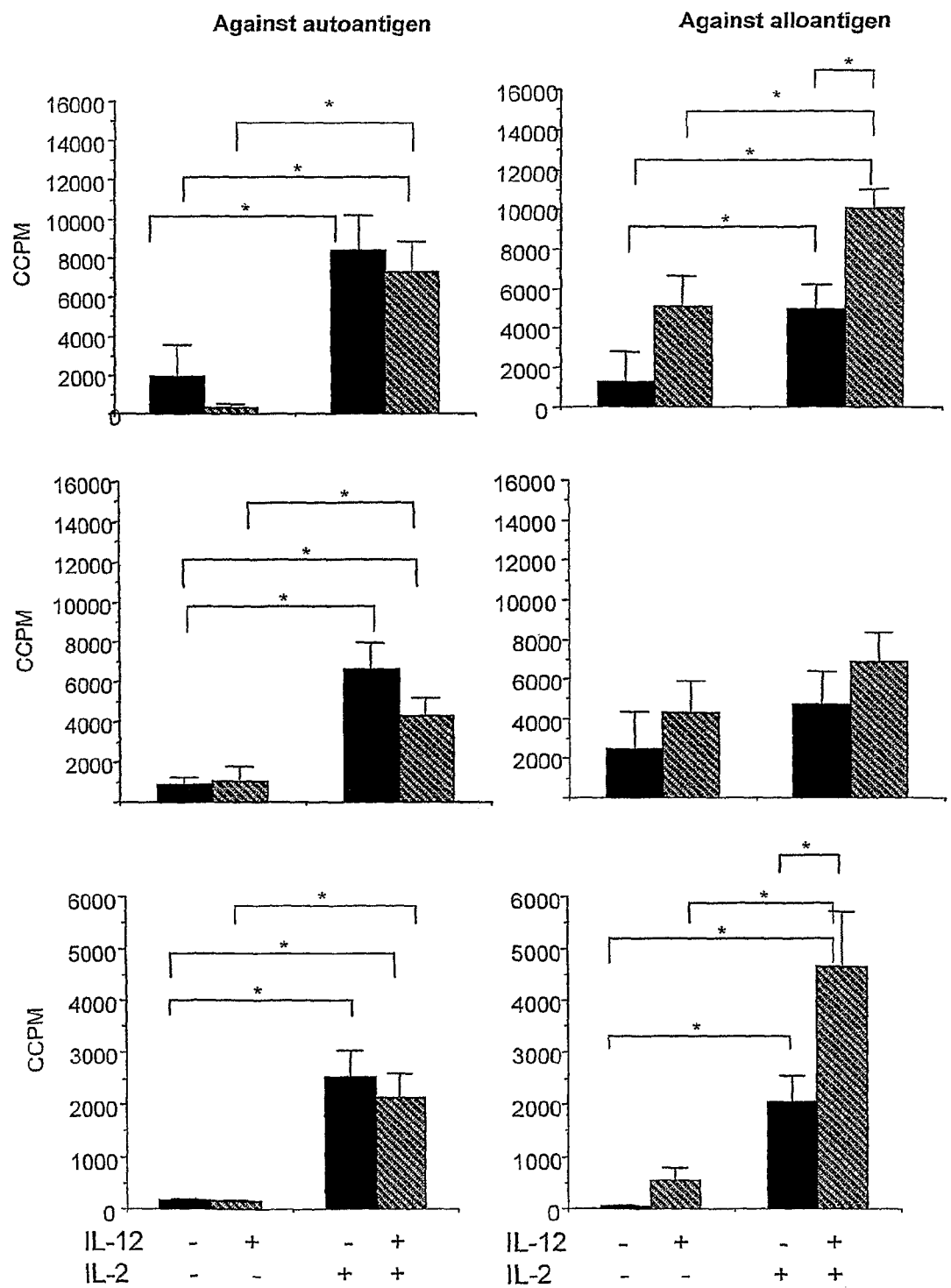
FIG. 11 shows the effect on proliferation of CD4$^+$,CD25$^+$ T cells of incubating CD4$^+$ T cells (top row), CD4$^+$,CD25$^-$ T cells (middle row) or CD4$^+$,CD25$^+$ T cells (bottom row) in the presence of autoantigen from DA rats (left column of graphs) or alloantigen (from PVG rats) (right column of graphs) in the presence of IL-2, IL-12, or IL-2 and IL-12 as indicated at the bottom of the diagram.

FIG. 11 illustrates an experiment that was conducted to compare the proliferation of unfractionated CD4+ T cells, a CD4+CD25− T cell subset and a CD4+CD25+ T cell subset from naïve DA rats after culturing the T cells for 4 days in the

TABLE 2

| Adoptive transfer* animals restored with | | | | Animals with severe rejection† | | | |
|---|---|---|---|---|---|---|---|
| CD4+, CD25+ cells | | Naïve CD4+ | Heart donor | | | Days post-transplant§ | Significance |
| No. | Culture with | cells | rat strain | Number/Total | Median | Day (number of animals) | (p)‡ |
| — | — | $5 \times 10^6$ | PVG | 12/12 | 12 | 10(3), 12(4), 13, 14(2), 18, 20 | — |
| — | — | $5 \times 10^6$ | Lewis | 3/3 | 10 | 9, 10(2) | — |
| $5 \times 10^6$ | — | $5 \times 10^6$ | PVG | 3/9 | >100 | 16(3), >100(6) | p = 0.0006 |
| $0.5 \times 10^6$ | — | $5 \times 10^6$ | PVG | 8/9 | 14 | 8, 13(3), 14(4), >100 | NSD |
| $0.5 \times 10^6$ | IL-2 and PVG cells | $5 \times 10^6$ | PVG | 1/6 | >100 | 12, >100(5) | p = 0.0066 |
| $0.5 \times 10^6$ | IL-2 and PVG cells | $5 \times 10^6$ | Lewis | 5/5 | 11 | 9, 11(4) | NSD |
| $0.5 \times 10^6$ | IL-4 and PVG cells | $5 \times 10^6$ | PVG | 2/6 | >50 | 10, 14, >50(4) | p = 0.0351 |
| $0.5 \times 10^6$ | IL-4 and PVG cells | $5 \times 10^6$ | Lewis | 4/6 | 19(13-24) | 8, 9, 13, 24, >50(2) | NSD |

*In the adoptive transfer assay, the recipient and donor are irradiated and a heart graft performed one day later. The irradiated recipients do not reject their graft but rejection can be restored with naive CD4+ T cells.
†Severe rejection refers to rejection associated with major swelling, loss of contraction and slowing of beat, equivalent to major graft dysfunction. Clinically this severity of rejection would be incompatible with life.
§Number of days post-transplantation at which severe rejection occurred for those animals which underwent rejection. Animals that did not have a severe rejection episode had excellent heart graft function for >50-100 days.
‡Compared to animals reconstituted with $5 \times 10^6$ naïve CD4+ T cells of the same heart donor strain. NSD; not significantly different.

Example 11

These experiments examined whether CD4+,CD25+ T cells from DA rats activated to antigen from PVG rats and cultured in the presence of PVG cells and IFN-γ were capable of suppressing rejection of a PVG cardiac graft in DA rats.

Figure 10:
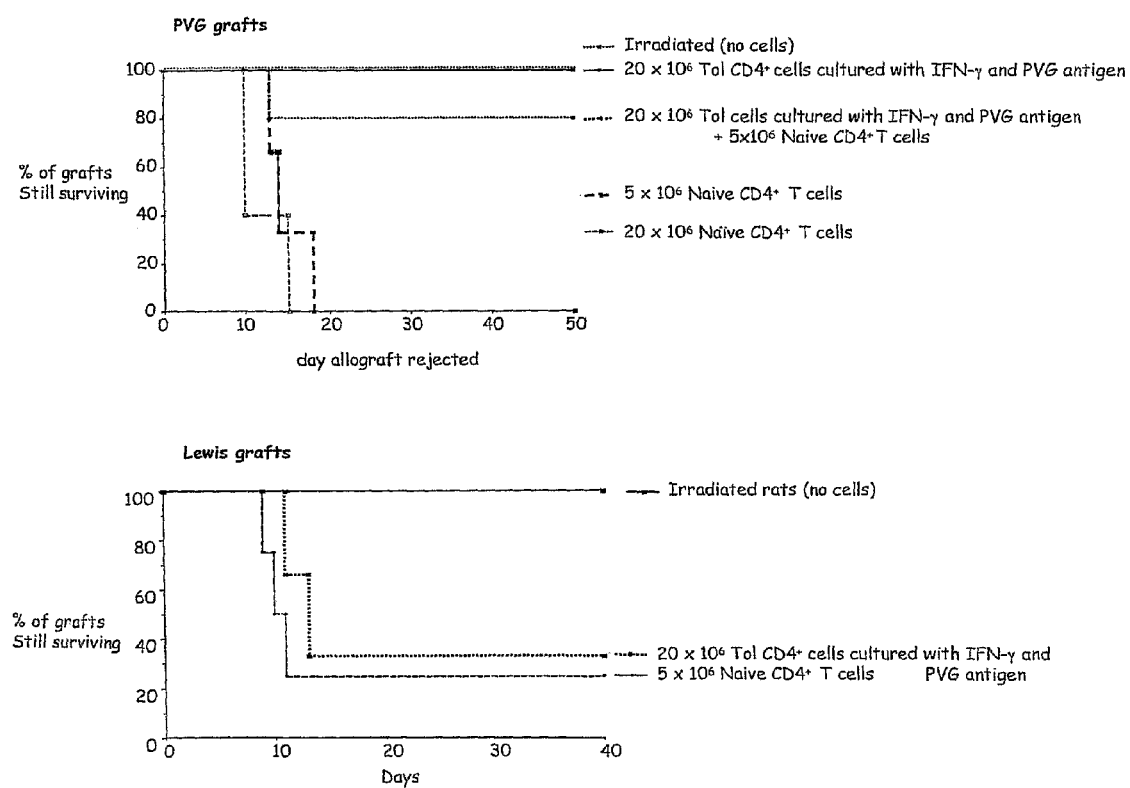
FIG. 10 shows the % survival in PVG cardiac allografts (upper panel) and Lewis (third party) cardiac allografts (lower panel) over 50 days in irradiated DA rats which received $20 \times 10^6$ CD4$^+$ T cells from DA rats tolerant to PVG antigen cultured with IFN-γ in the presence of PVG antigen (full line, upper graph) (dotted line, lower graph); $5 \times 10^6$ Naïve CD4$^+$ T cells (thick dashed line, upper and lower graph); $20 \times 10^6$ Naïve CD4$^+$ T cells (thin dashed line, upper graph); $20 \times 10^6$ CD4$^+$,CD25$^+$ T cells from DA rats tolerant to PVG antigen mixed with $5 \times 10^6$ Naïve CD4$^+$ T cells (dotted line, upper graph); irradiated DA rats (no cells) (solid line, upper and lower graph).

CD4+ T cells from DA rats tolerant to a cardiac allograft from PVG rats were cultured in mixed lymphocyte culture with PVG alloantigen (as described in Example 1) and >100 units/ml of IFN-γ. After three days the T cells were adoptively transferred to irradiated DA rats grafted with either specific donor PVG cardiac allografts (grafts from PVG rats), or third party Lewis allografts (grafts from Lewis rats). Each irradiated rat was then restored with 5×10⁶ naïve CD4+ T cells. The survival of grafts was then monitored over a 50 day period. The results of the experiment are shown in FIG. 10. The upper graph of FIG. 10 shows the survival when T cells were adoptively transferred to irradiated DA rats grafted with PVG cardiac allografts. The lower graph of FIG. 10 shows the survival when T cells were adoptively transferred to irradiated DA rats grafted with third party Lewis cardiac allografts.

As can be seen from FIG. 10, the only grafts which demonstrated significant survival over the 50 day period were grafts in rats which received no cells (see FIG. 10 upper and lower graphs, solid line), or PVG grafts (but not Lewis grafts) in rats which received CD4+ T cells cultured in the presence of PVG antigen and IFN-γ (see FIG. 10, upper graph, dotted line closed circles). The CD4+ T cells cultured with IFN-γ when admixed with 5×10⁶ naïve CD4+ T cells suppressed allograft rejection, indicating that they retained suppressor capacity.

These results indicate that the cultured CD4+ T cells continued to suppress PVG allograft rejection but did not suppress Lewis graft rejection. Naïve cells alone effected rejection, whereas irradiation delayed rejection.

presence of autoantigen (DA antigen) or alloantigen (PVG antigen) in media supplemented with IL-2 or IL-12p70 or both IL-2 and IL-12p70. The effect of the antigen and cytokine combination on cell proliferation is shown in FIG. 11. Proliferation of unfractionated CD4+ T cells is shown in the top row of graphs, proliferation of the CD4+CD25− T cell subset is shown in the middle row of graphs, and proliferation of the CD4+CD25+ T cell subset is shown in the lower row of graphs. The left hand column of graphs show proliferation in response to autoantigen, and the right hand column of graphs show proliferation in response to alloantigen (PVG).

As can be seen from FIG. 11, proliferation was not enhanced by IL-12p70 alone when compared to control nil cytokines. IL-2 induced marked proliferation of all subsets, and addition of IL-12p70 enhanced this proliferation in the CD4+ and the CD4+CD25+ populations but not in the CD4+CD25− T cells.

These results indicate that IL-12p70 enhances proliferation of CD4+,CD25+ T cells that have been activated with antigen and IL-2 (Ts1 cells).

In parallel experiments, culturing of cells with IL-4 and IL-12p70 did not enhance proliferation above that with IL-4 clone.

Example 13

This experiment examined the effect of IL-2 and IL-12p70 on growth of Ts1 cells (CD4+,CD25+ T cells activated by culturing in the presence of antigen and IL-2).

Ts1 cells were prepared by culturing naïve CD4+CD25+ T cells in the presence of IL-2 and alloantigen (PVG antigen) for 3 days. Cells were then washed and place in fresh media with alloantigen and either no supplement, CHO—K supernatant, IL-2, IL-12p70 or IL-12p40>100 units/ml. Cell proliferation was then measured as described above. The results of cell proliferation are shown in FIG. 12.

Figure 12:
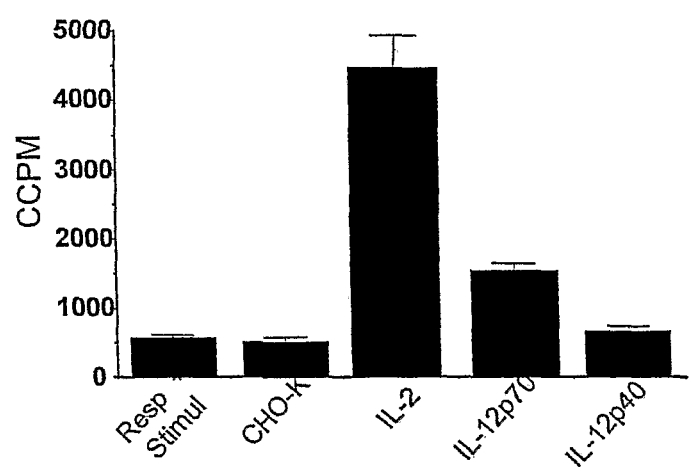
FIG. 12 shows proliferation of CD4$^+$,CD25$^+$ T cells after activation in the presence of IL-2 and PVG antigen for 3 days, followed by incubation in the presence of no supplement (Resp. Stimul), CHO—K supernatant (CHO—K), IL-2 (IL-2), IL-12p70 (IL-12p70) or IL-12p40 (IL-12p40).

As can be seen from FIG. 12, cultures with control CHO—K supernatant or IL-12p40 exhibited proliferation similar to those with no supplement. Culturing in the presence of IL-12p70 induced significant extra proliferation compared to controls, as did culturing in the presence of IL-2. These experiments indicate that Ts1 cells are responsive to IL-12p70.

Example 14

Proliferation of unfractionated CD4$^+$ T cells, a CD4$^+$CD25$^+$ T cell subset and a CD4$^+$CD25$^+$ T cell subset from naïve DA rats was compared after culture for 4 days against auto-antigen (DA antigen) or alloantigen (PVG antigen) when media was supplemented with no cytokine, IL-4 or IL-12p70 or both IL-12 and IL-12p70. Proliferation was not enhanced by IL-12p70 alone when compared to control nil cytokines. IL-4 induced marked proliferation of all subsets, and addition of IL-12p70 did not enhance proliferation of any of the subpopulations. This showed IL-12p70 did not enhance proliferation of Ts2 cells.

Example 15

RT-PCR was used to analyse the expression of IL-2 and IL-12p2 receptor mRNA in CD4$^+$,CD25$^+$ T cells from naïve DA rats following culturing with alloantigen (cells from PVG rats) or autoantigen (cells from DA rats) and IL-2 or IL-4>100 units/ml. The results of the RT-PCR analysis are shown in FIG. 13.

Figure 13:
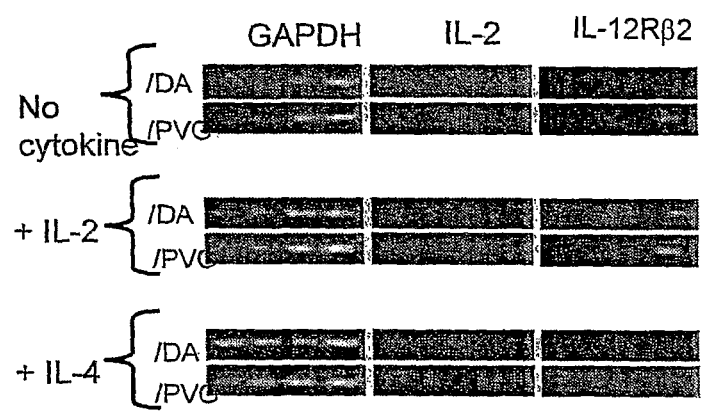
FIG. 13 shows the results of RT-PCR GAPDH, of IL-2 or IL-12Rβ2 mRNA from CD4$^+$,CD25$^+$ T cells following culturing with autoantigen (DA antigen) or alloantigen (PVG antigen) for 4 days in the presence of IL-2 or IL-4.

FIG. 13 illustrates RT-PCR of GAPDH (control), IL-2 or IL-12β2 receptor mRNA following culture will alloantigen (PVG) or autoantigen (DA) for 4 days with no cytokine (upper panels); IL-2, (middle panel); or IL-4 (lower panel). As can be seen from FIG. 13, strong bands were observed for IL-12β2 receptor when cells were cultured with IL-2 and alloantigen. A feint band was observed for IL-12β2 receptor following alloantigen stimulation alone. This result suggests preferential up regulation of the IL-12 receptor on CD4$^+$CD25$^+$ T cells activated by contacting with alloantigen in the presence of IL-2.

Example 16

EAN was induced in 10-15 week old female Lewis rats by immunization with bovine peripheral nerve myelin (PNM) in Freund's complete adjuvant, as described in J. Neurol. Sci. 1994, 123: 162-172. The animals were divided into three groups: (a) those immunised with PNM and Freund's adjuvant only (control); (b) those immunised with PNM and Freund's adjuvant and administered CHO cell supernatant (control); and (c) those immunised with PNM and Freund's adjuvant and administered IL-5 (5000 units/day daily intraperitoneal injection from the day of onset of clinical for 10 days).

All groups of Lewis rats (n=5-12) were immunised with peripheral nerve myelin (PNM) and Freund's adjuvant as described above.

The animals were monitored for disease activity daily by weighing and clinical observation and scoring of paralysis using a semi-quantitative score. The score used was; 4+ paralysis of all limbs, 3+ Total hind limb paralysis, and weak forearms, 2+ weak hind limbs, 1+ weak tails, 0 normal.

Figure 14:
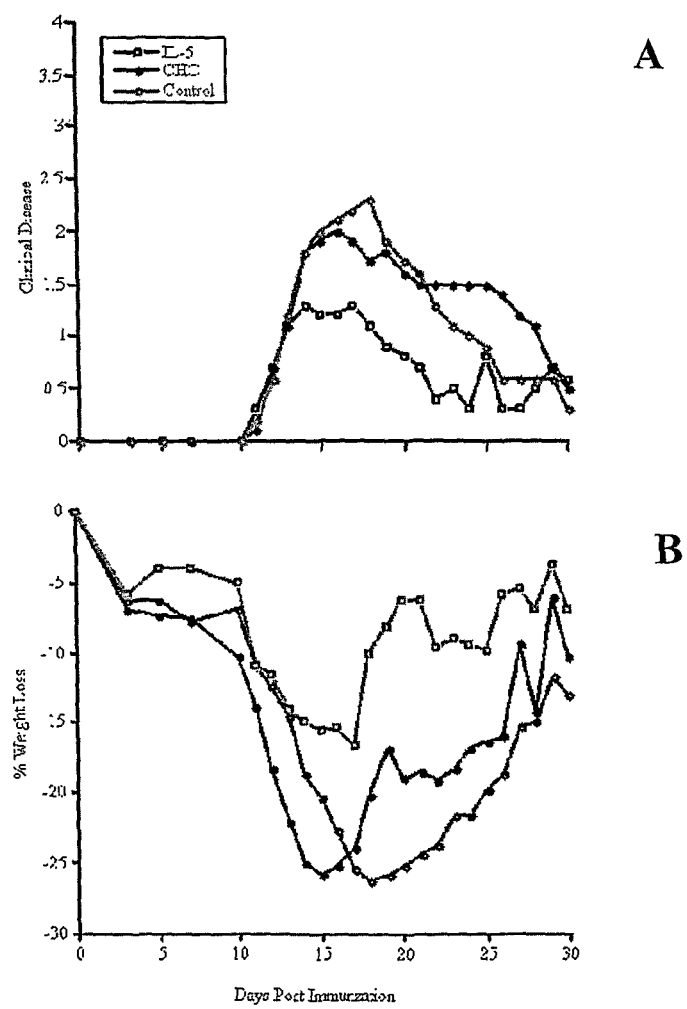
FIG. 14 shows the effect of administration of IL-5 on severity (A) and weight loss (B) in an experiment disease model of EAN. Open squares=Rats administered IL-5; closed circles=rats administered CHO—K supernatant; open circles=no treatment.

Referring to FIG. 14A, the effect of administration of IL-5 on the clinical course of Experimental Allergic Neuritis (EAN) in Lewis rats was examined.

As can be seen from FIG. 14A, those rats administered IL-5 had a milder clinical course with a maximum disease score just over one, compared to controls whose diseases peaked at 2.5+ around 15-16 days post immunization.

FIG. 14B illustrates weight loss over the course of the disease. Weight loss was less in those rats administered IL-5 when compared to the untreated control of following treatment with CHO cell supernatant.

Figure 15:
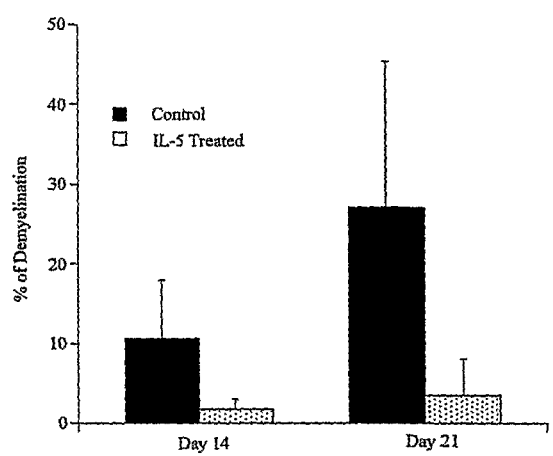
FIG. 15 shows the percent of demyelinated nerve fibres in peripheral nerves from an experimental rat model of EAN 14 and 21 days after immunisation with PNM. Rats treated with IL-5 at immunisation are represented by grey bars, rats that were untreated are represented by black bars.

The percent demyelination was also investigated in rats immunised with PNM with or without IL-5. The effect of treatment with IL-5 on demyelination at day 14 and 21 is shown in FIG. 15. As can be seen from FIG. 15, treatment with IL-5 may reduce the demyelination normally observed in the EAN model.

The above data suggests that administration of IL-5 may be effective in reducing the severity of EAN by inducing tolerance to PNM.

Example 17

Figure 16:
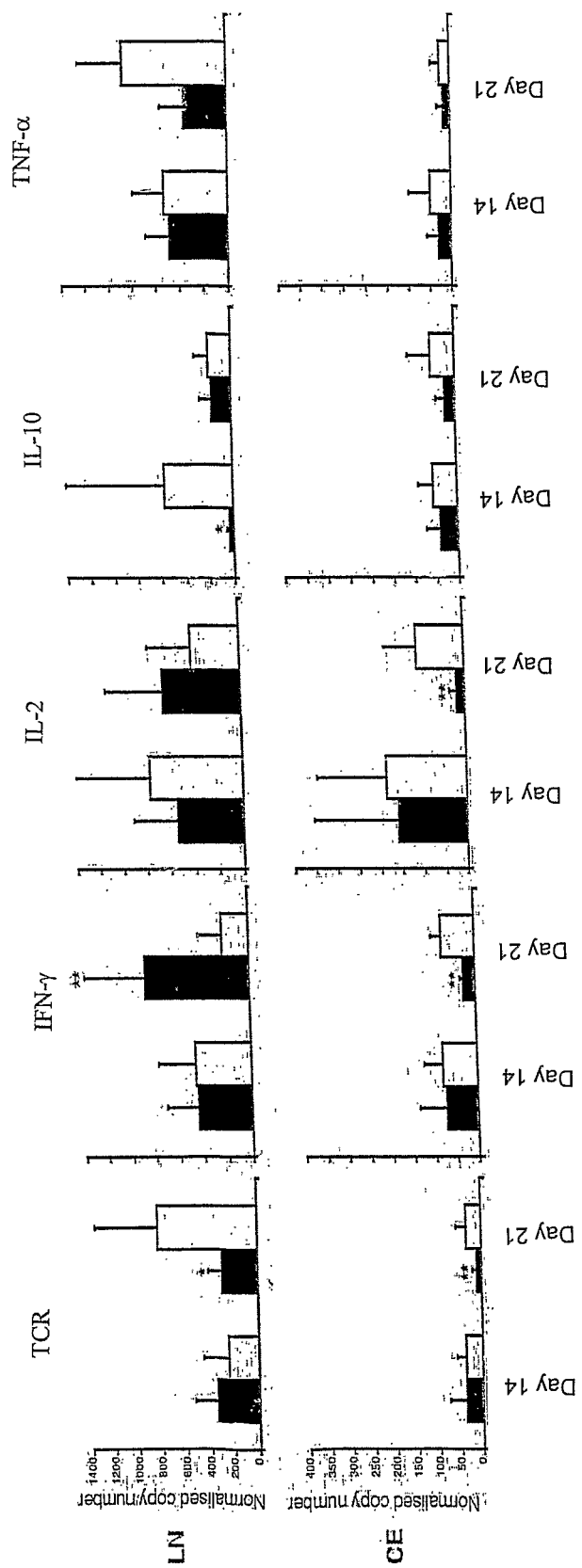
FIG. 16 shows the normalised copy number of mRNA following real time RT-PCR from draining lymph nodes (LN) or cauda equina (CE) of rats at 14 days or 21 days post-immunisation with PNM using primers to TCR, IFN-γ, IL-2, IL-10 or TNF-α (as indicated). Black bars represent IL-5 treated, open bars represent untreated. Significant is indicated as *p<0.05 and **p<0.01.

To determine the expression of cytokines in animals immunised with PNM and treated with IL-5 as described in Example 16, real time PCR analysis of mRNA from draining lymph nodes (LN) and cauda equina (CE) was performed at day 14 and 21 post immunisation with PNM. The results of the real-time PCR is shown in FIG. 16. Open bars represent mRNA levels of control rats that were not treated with IL-5, while closed bars represent mRNA levels of rats treated with IL-5. Cytokines that were measured are as indicated at the top of the diagram.

As can be seen from FIG. 16, in the lymph node draining the site of immunization, there was a marked increase in IFN-γ expression but not IL-2 in IL-5 treated rats (closed bars) at day 21 compared to controls (open bars), whereas IL-10 was reduced at day 14. In the cauda equina, there was marked reduction in IL-2 and IFN-γ, indicating reduced Th1 cell infiltration. TCR-α was less in both the lymph nodes and cauda equina at day 21 but not day 14. TCR-α, IL-10 and TNF-α results are expressed as copy number/100000 GAPDH copies. IL-2 and IFN-γ results are expressed as copy number/100 TCR-α copies. Data was combined of duplicate assays from 5 samples, expressed as mean ±SD. Statistical significant differences *p<0.05, **p<0.005.

Example 18

Expression of IL-5, IL-5 receptor, IL-4 and IL-13 in draining lymph nodes and cauda equine in rats that had been immunised with PNM and were either untreated (CTL) or treated with IL-5 as described in Example 15 were examined using semi-quantitative RT-PCR. The results of semi-quantitative RT-PCR are shown in FIG. 17.

Figure 17:
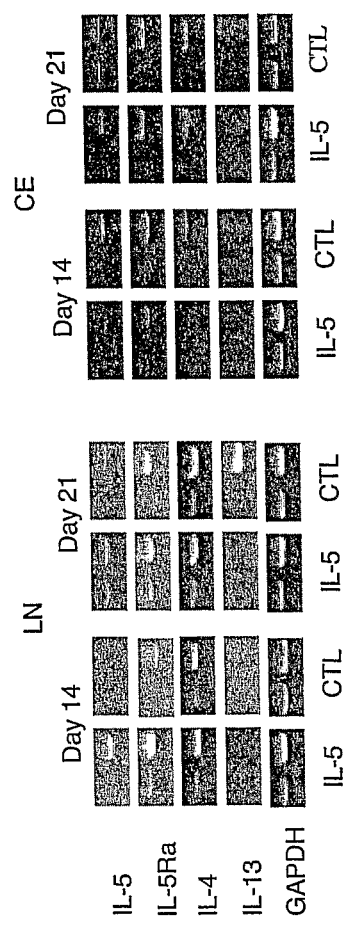
FIG. 17 shows the results of RT-PCR analysis of IL-5, IL-5Rα, IL-4 and IL-13 mRNA expression at day 14 and day 21 in draining lymph nodes (LN) and cauda equine (CE) of rats immunised with DNA and either administered IL-5 (IL-5) or no IL-5 (CTL).

Referring to FIG. 17, semi-quantitative RT-PCR of cytokine mRNA showed IL-5 treated animals have increased IL-5 and IL-5Rα in the lymph node draining the site of immunization. There was similar expression of IL-4 but reduced IL-13 in IL-5 treated compared to control (CTL). In the cauda equina, IL-5 and IL-5Rα was still detected, even though TCR-α copies were reduced (refer to FIG. 3). Each box shown serial cDNA dilutions with neat on right and 1:10 dilution on the left. Control GAPDH expression was similar in all samples. Results from 5 samples per group with one representative sample shown.

Example 19

Figure 18:
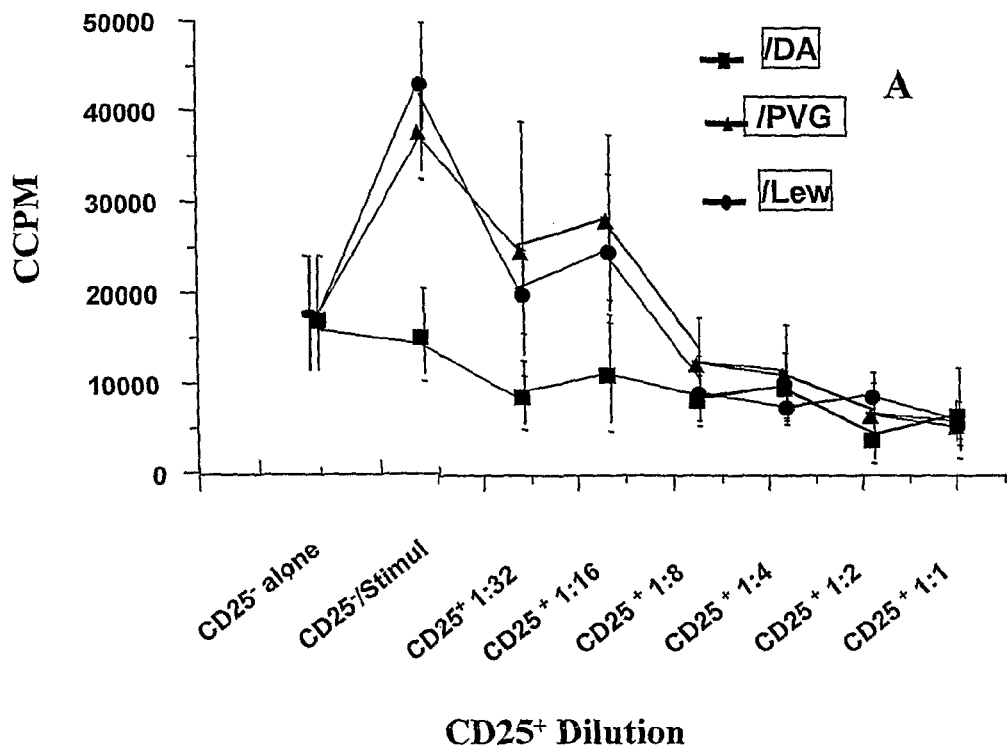
FIG. 18 shows the effect of CD4$^+$,CD25$^+$ T cells on proliferation of naïve CD4$^+$,CD25$^-$ T cells in a limiting dilution assay, A: naïve CD4$^+$,CD25$^-$ T cells were mixed with 1:2 serial dilution of naïve CD4$^+$CD25$^+$ T cells; B: naïve CD4$^+$, CD25$^-$ T cells were mixed with 1:2 serial dilution of CD4$^+$, CD25$^+$ T cells which had been cultured in the presence of PVG antigen and IL-2.
Figure 18:
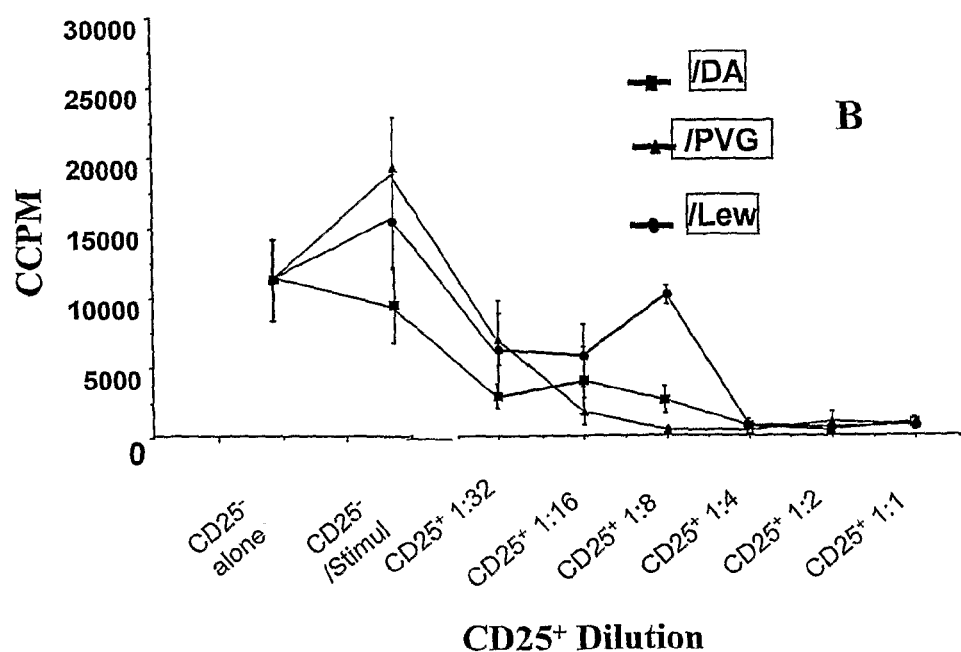

The effect of naïve and activated CD4$^+$CD25$^+$ T cells on proliferation of naïve CD4$^+$CD25$^-$ T cells in MLC was tested in a limiting dilution assay with a 1:2 serial dilutions of CD4$^+$,CD25$^+$ T cells were mixed with a constant number of naïve (10$^5$) CD4$^+$,CD25$^-$ T cells. The results of the limiting dilution study are shown in FIG. 18.

FIG. 18(A) shows the ability of fresh naïve CD4$^+$CD25$^+$ T cells to partially suppress responses to PVG antigen and Lewis antigen, at a ratio of 1:1. The ability of the naïve T cells to suppress response to PVG antigen is significant diminished at a ratio of 1:8 (naïve CD4$^+$,CD25$^+$:CD4$^+$,CD25$^-$ T cells).

FIG. 18(B) shows Ts 1 cells (CD4$^+$,CD25$^+$ T cells activated to antigen (in this case PVG antigen in the presence of IL-2) selectively fully suppress responses to PVG antigen to a ratio of 1:16 but only suppress to Lewis antigen (third party) at a ratio of 1:4 then lose suppression.

Figure 19:
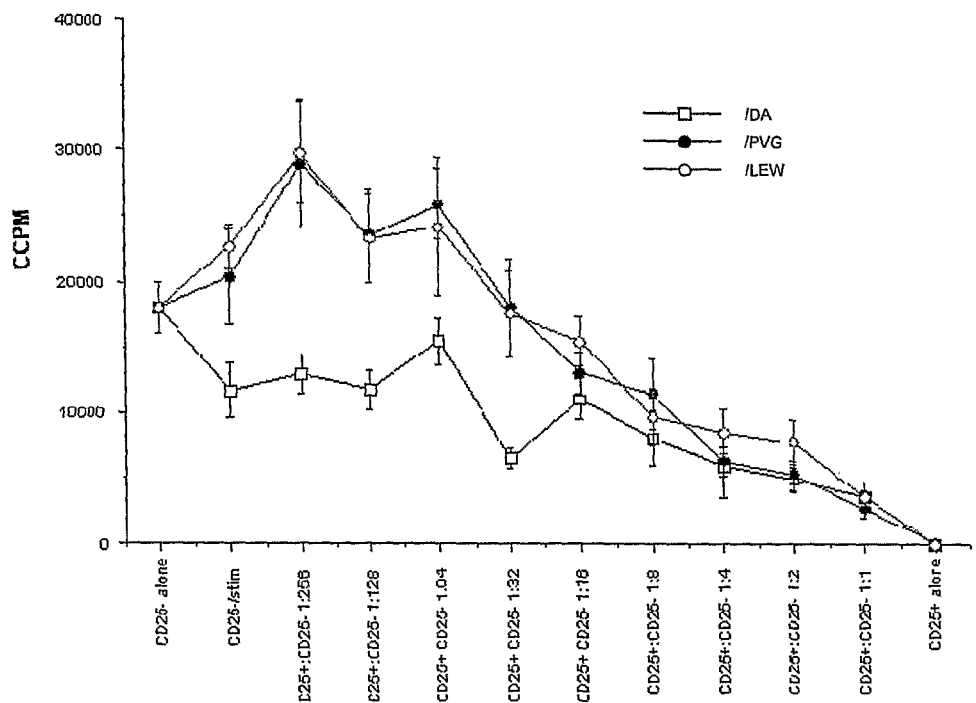
FIG. 19 shows the effect of CD4$^+$,CD25$^+$ T cells on proliferation of naïve CD4$^+$,CD25$^-$ T cells in a limiting dilution assay, A: naïve CD4$^+$,CD25$^-$ T cells were mixed with 1:2 serial dilution of naïve CD4$^+$,CD25$^+$ T cells; B: naïve CD4$^+$, CD25$^-$ T cells were mixed with 1:2 serial dilution of CD4$^+$, CD25$^+$ T cells which had been cultured in the presence of PVG antigen and IL-4.
Figure 19:
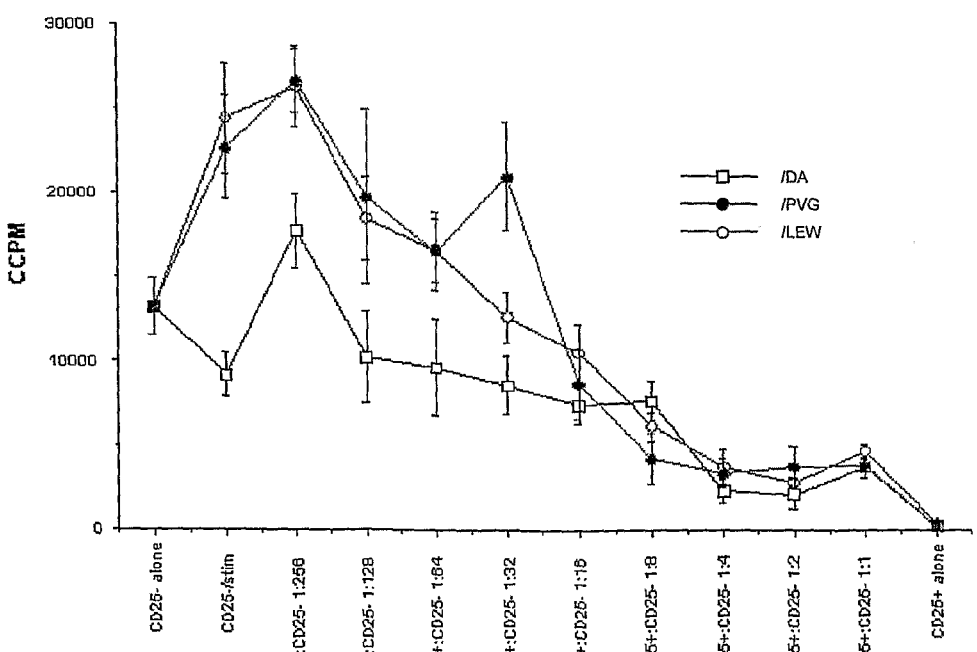

Referring to FIG. 19A, FIG. 19A shows that fresh naïve CD4$^+$CD25$^+$ T cells partially suppress responses to PVG antigen and Lewis antigen, at a ratio of 1:1 but loose significant inhibition at a ratio of 1:8. FIG. 19(B) shows that Ts2 cells (CD4$^+$,CD25$^+$ T cells activated to (in this case PVG antigen) in the presence of IL-4) partially suppress both responses to PVG and Lewis antigen and do so in ratios similar to that observed with fresh naïve cells. In other studies we have shown the MLC mainly induces Th1 responses with induction of IL-2 and IFN-γ. The only Th2 cytokine induced is IL-4 with no IL-5 or IL-10 unless cells are exposed to extra IL-4, when IL-2 and IFN-γ induction is significantly suppressed an IL-4 and IL-5 expression enhanced.

Example 20

This experiment was conducted to determine the affect of incubating CD4$^+$,CD25$^+$ T cells in the presence of IL-23 and IL-13 following activation of naïve CD4$^+$,CD25$^+$ T cells in the presence of IL-2 or IL-4.

Naïve CD4$^+$,CD25$^+$ T cells from naïve DA rats were incubated with stimulator cells from PVG rats in the presence of either IL-2 (group A) or IL-4 (group B) for 3 to 4 days as described above. Following 3 to 4 days, the cells were washed and the culture medium replaced with culture medium containing either 100 units/ml IL-12p70 (positive control), IL-23, IFN-γ, IL-10 or IL-12p70 and IFN-γ for group A, and 100 units/ml IL-13 or IL-13 and IL-5 for group B. Negative control was CHO cell supernatant.

CD4$^+$,CD25$^+$ T cells incubated in the presence of IL-12p70, IL-23 and IL-13 alone exhibited further proliferation. CD4$^+$,CD25$^+$ T cells incubated in the presence of IL-13 and IL-5, or IL-12p70 and IFN-γ also showed enhanced proliferation.

The following examples are prophetic examples intended to illustrate various embodiments of various aspects of the invention.

Prophetic Example 1

This example illustrates the use of CD4$^+$,CD25$^+$ T cells to determine whether a subject is tolerant to a specific antigen.

CD4$^+$,CD25$^+$ T cells may be isolated from lymphocyte cultures obtained from patients in which tolerance to a specific antigen is to be tested. The CD4$^+$,CD25$^+$ T cells may be isolated using the methods described above.

Figure 20:
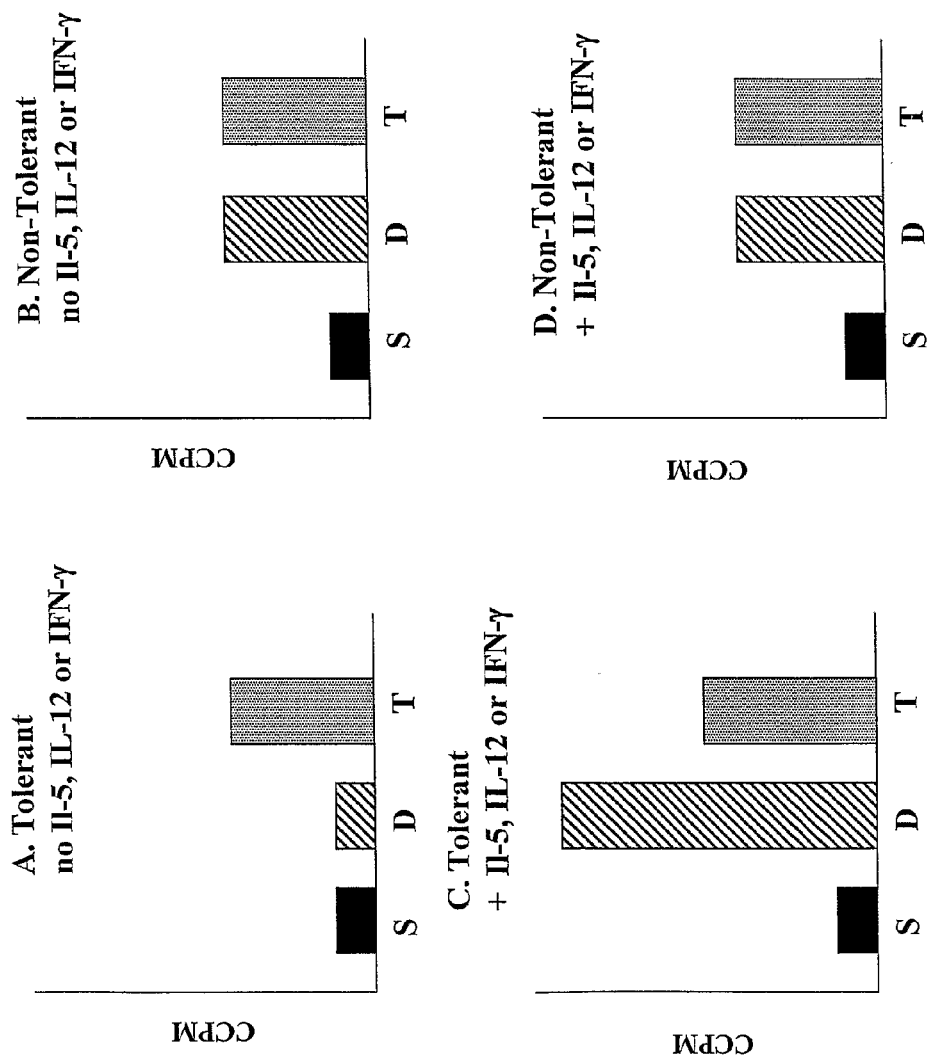
FIG. 20 shows the expected relative cell proliferation of isolated CD4$^+$,CD25$^+$ T cells from a subject tolerant (A and C) or non-tolerant (B and D) to a donor antigen following culturing in the absence (A and B) or presence (C and D) of IL-5, IL-12 or IFN-γ and self antigen (S), donor antigen (D) or third party antigen (T).

In one form, aliquots of approximately 10$^5$ CD4$^+$,CD25$^+$ T cells from a subject are contacted with donor antigen, self antigen or a third party antigen in culture medium that is cytokine free or does not contain IL-2, IL-4, IL-5, IL-12 or IFN-γ for at least 3 days, typically 5 days. Cell proliferation after 3 days is measured as described above. FIGS. 20(A) and (B) illustrates the expected result from a subject that is tolerant (A) or non-tolerant (B) to the donor antigen. As can be seen in FIG. 20, there will be little or no proliferation of CD4$^+$,CD25$^+$ T cells from a subject that is tolerant to the donor antigen (A) in the absence of IL-5, IL-12 or IFN-γ. In this regard, cell proliferation of CD4$^+$,CD25$^+$ T cells in contact with donor antigen would be comparable to proliferation of CD4$^+$,CD25$^+$ T cells in contact with self antigen. In contrast, CD4$^+$,CD25$^+$ T cells from a non-tolerant subject (B) will exhibit similar proliferation as that observed in response to contact with third party antigen.

In another form, aliquots of approximately 10$^5$ CD4$^+$, CD25$^+$ T cells from a subject are contacted with donor antigen, self antigen or a third party antigen, in culture medium such as RPM1 with 10% FCS that is supplemented with 10 mg/ml (HOW MUCH?) IL-5, IFN-γ and/or IL-12p70 for at least 3 days. Cell proliferation after 3 days is measured as described above. FIGS. 20C and D illustrate the expected result from a subject that is tolerant (C) or non-tolerant (D) to the donor antigen. As can be seen in FIG. 20, CD4$^+$,CD25$^+$ T cells from a subject that is tolerant to the donor antigen would proliferate in the presence of IL-5, IL-12 or IFN-γ. In this regard, cell proliferation of CD4$^+$,CD25$^+$ T cells in contact with donor antigen would be greater than proliferation of CD4$^+$,CD25$^+$ T cells in contact with third party antigen. In contrast, CD4$^+$,CD25$^+$ T cells from non-tolerant subjects in contact with donor antigen would show similar proliferation as that observed for cells in contact with third party antigen.

Prophetic Example 2

This example illustrates the use of unfractionated CD4$^+$ T cells to determine whether a subject is tolerant to a specific antigen.

Figure 21:
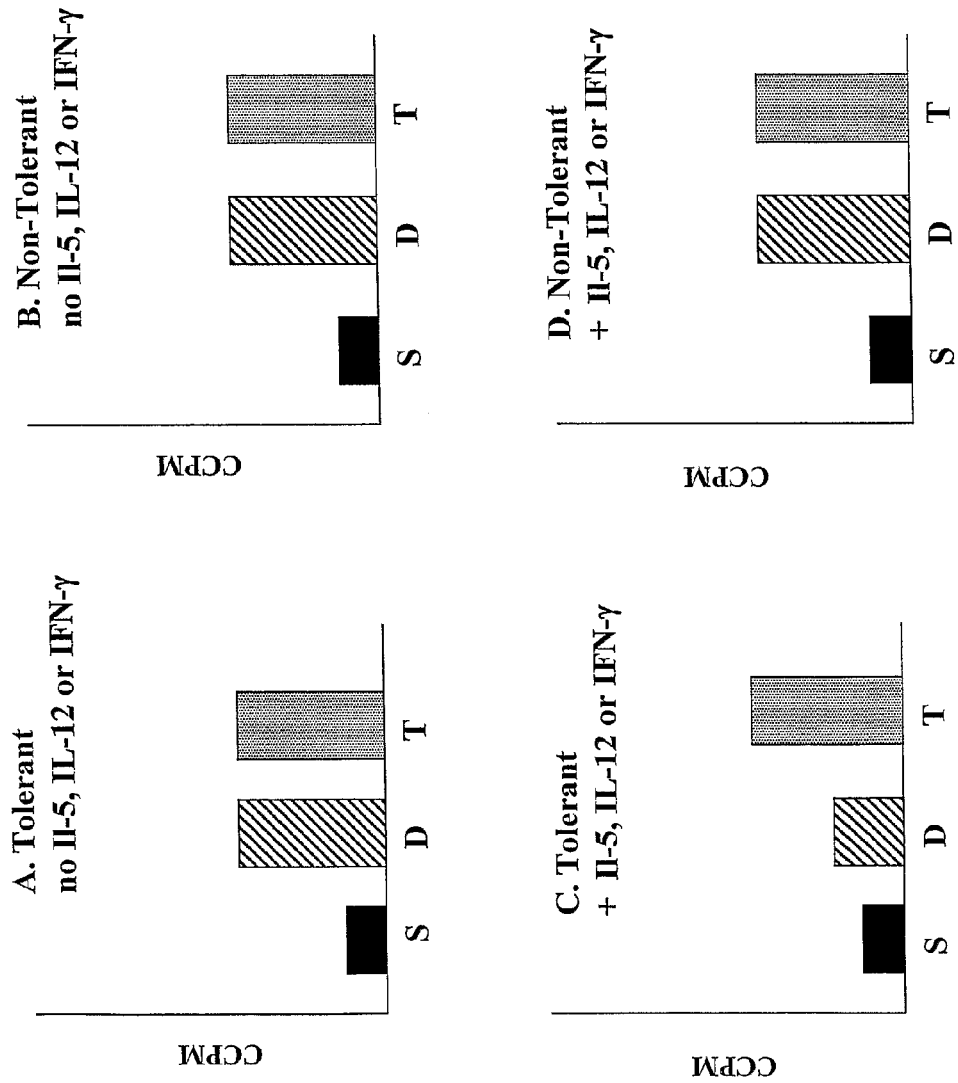
FIG. 21 shows the expected relative cell proliferation of CD4$^+$ T cells from a subject tolerant (A and C) or non-tolerant (B and D) to a donor antigen following culturing of the CD4$^+$ T cells in the absence (A and B) or presence (C and D) of IL-5, IL-12, or IFN-γ and self antigen (S), donor antigen (D) or third party antigen (T)

In one form, aliquots of approximately 10$^5$ CD4$^+$ T cells from a subject are contacted with donor antigen, self antigen or third party antigen in culture medium (such as RPM1 supplemented with 10% FCS) that is cytokine free or is at least not supplemented with IL-2, IL-4, IL-5, IFN-γ or IL-12p70 for at least 4 days. Cell proliferation after 4 days is measured as described above. FIGS. 21(A) and (B) illustrates the expected result from a subject that is tolerant (A) or non-tolerant (B) to the donor antigen. Proliferation in response to donor antigen will be similar to that of the response to the third party antigen due to death of CD4$^+$, CD25$^+$ T cells in the absence of cytokine and therefore inability to suppress CD4$^+$,CD25$^-$ T cells, as well as reduced numbers of CD4$^+$,CD25$^-$ T cells, as indicated in FIG. 1F.

Referring to FIG. 21(B), in a non-tolerant subject, the response to donor antigen will be the same as that to third party antigen as both have normal numbers of CD4$^+$,CD25$^+$ T cells, and suppression by naïve CD4$^+$,CD25$^+$ T cells.

In the presence of IL-5, IL-12, or IFN-γ, activated CD4$^+$, CD25$^+$ T cells from tolerant subjects will survive and suppress the proliferation of CD4$^+$CD25$^-$ T cells in response to donor antigen as illustrated in C. Thus, proliferation of CD4$^+$ T cells from tolerant subjects in response to donor antigen will be reduced and similar to the response to self and less than the response to third party antigen. CD4$^+$ T cells from non-tolerant individuals (see FIG. 21D) will exhibit a similar proliferation to donor antigen as that in response to third party antigen.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of assessing whether a subject comprises CD4+, CD25+high T cells that have been activated to a specific non-self antigen, and is therefore tolerant, or capable of becoming tolerant, to the specific non-self antigen, the method of comprising:

(a) in a first culture, incubating a first portion of a population of T lymphocytes comprising, CD4+, CD25+high T cells obtained from the subject in the presence of (i) one or more cytokines selected from the group consisting of IL-5, IL-12 and IFN-γ, wherein the one of more cytokines are isolated or purified proteins or are contained in supernatant from a CHO—K1 cell transfected with a nucleic acid which expresses the one or more cytokines in the CHO—K1 cell so that the transfected CHO—K1 cell produces the one or more cytokines, and (ii) the specific non-self antigen bound to the surface of an antigen presenting cell, wherein the proliferation of the antigen presenting cell has been impaired, or the specific non-self antigen bound to a synthetic antigen presenting system;

(b) in a second culture, incubating a second portion of a population of T lymphocytes comprising CD4+, CD25+high T cells obtained from the subject in the presence of (i) one or more cytokines selected from the group consisting of IL-5, IL-12 and IFN-γ, wherein the one or more cytokines are isolated or purified proteins or are contained in supernatant from a CHO—K1 cell transfected with a nucleic acid which expresses the one or more cytokines in the CHO—K1 cell so that the transfected CHO—K1 cell produces the one or more cytokines, and (ii) a self antigen bound to the surface of an antigen presenting cell, wherein the proliferation of the antigen presenting cell has been impaired, or a self antigen bound to a synthetic antigen presenting system; and (c) detecting proliferation or survival of CD4+CD25+high T cells in the first culture and the second culture, wherein when the CD4+CD25+high T cell proliferation or survival in the fast culture exceeds the CD4+CD25+high T cell proliferation or survival the second culture, wherein said subject comprises CD4+CD25+high T cells that have been activated to the specific non-self antigen, and is therefore tolerant, or capable of becoming tolerant, to the specific non-self antigen, when the CD4+CD25+high T cell proliferation or survival in the first culture exceeds the CD4+CD25+high T cell proliferation or survival in the second culture.

2. The method of claim 1, wherein the cytokine is IL-5.

3. The method of claim 1, wherein the cytokine is IL-12.

4. The method claim 1, wherein the cytokine is IFN-γ.

5. The method of claim 1, wherein the population of lymphocytes is isolated CD4+lymphocytes.

6. The method of claim 1, wherein the population of lymphocytes is at least 96% CD4+and at least 85% CD4+CD25+high.

7. The method of claim 1, wherein the specific non-self antigen is selected from the group consisting of alloantigen, xenoantigen, allergen and an antigen from an infectious disease.

8. The method of claim 1, wherein the subject is a human.

9. The method of claim 1, wherein the one or more cytokines selected from the group consisting of IL-5, IL-12 and IFN-γ is a purified protein.

10. The method of claim 1, wherein the one or more cytokines selected from the group consisting of IL-5, IL-12 and IFN-γ is contained in the supernatant from a CHO—K1 cell producing the cytokine.

11. The method of claim 6, wherein (c) comprises detecting proliferation of CD4+CD25+high T cells in the first culture and the second culture, and wherein the subject comprises CD4+, CD25+high T cells that have been activated to the specific non-self antigen when the CD4+, CD25+high T cell proliferation in the first culture exceeds the CD4+, CD25+high T cell proliferation in the second culture.

* * * * *

UNITED STATES PATENT AND TRADEMARK OFFICE
CERTIFICATE OF CORRECTION

PATENT NO. : 8,785,140 B2  
APPLICATION NO. : 11/815420  
DATED : July 22, 2014  
INVENTOR(S) : Hall et al.

Page 1 of 1

It is certified that error appears in the above-identified patent and that said Letters Patent is hereby corrected as shown below:

On Title Page:
Item (73), Assignee: Please correct "Syndey, New South Wales (AU)"
to read -- Sydney, New South Wales (AU) --

In the Specification:
Column 65, Line 27: Please correct "IL-12p2" to read -- IL-12β2 --

In the Claims:
Column 69, Claim 1, Line 9: Please correct "method of comprising:"
to read -- method comprising: --

Column 70, Claim 1, Line 2: Please correct "the fast culture"
to read -- the first culture --

Column 70, Claim 1, Line 3: Please correct "survival the second"
to read -- survival in the second --

Signed and Sealed this
Twenty-seventh Day of October, 2015

Michelle K. Lee
*Director of the United States Patent and Trademark Office*